(12) United States Patent
Walensky et al.

(10) Patent No.: US 9,296,805 B2
(45) Date of Patent: Mar. 29, 2016

(54) STABILIZED INSULINOTROPIC PEPTIDES AND METHODS OF USE

(75) Inventors: Loren D. Walensky, Newton, MA (US); Gregory Bird, Pelham, NH (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/809,259

(22) PCT Filed: Jul. 8, 2011

(86) PCT No.: PCT/US2011/043465
§ 371 (c)(1),
(2), (4) Date: Mar. 1, 2013

(87) PCT Pub. No.: WO2012/006598
PCT Pub. Date: Jan. 12, 2012

(65) Prior Publication Data
US 2013/0157942 A1 Jun. 20, 2013

Related U.S. Application Data
(60) Provisional application No. 61/363,097, filed on Jul. 9, 2010.

(51) Int. Cl.
| | |
|---|---|
| *C07K 14/575* | (2006.01) |
| *C07K 14/62* | (2006.01) |
| *A61K 38/22* | (2006.01) |
| *A61K 38/26* | (2006.01) |
| *A61P 3/10* | (2006.01) |
| *C07K 14/605* | (2006.01) |
| *A61K 38/00* | (2006.01) |

(52) U.S. Cl.
CPC .......... *C07K 14/605* (2013.01); *C07K 14/575* (2013.01); *C07K 14/57563* (2013.01); *A61K 38/00* (2013.10)

(58) Field of Classification Search
None
See application file for complete search history.

(56) References Cited

U.S. PATENT DOCUMENTS

| | | | |
|---|---|---|---|
| 4,522,752 A | 6/1985 | Sisto et al. | |
| 5,424,286 A | 6/1995 | Eng | |
| 6,015,881 A | 1/2000 | Kang | |
| 7,084,244 B2 | 8/2006 | Gilon et al. | |
| 7,192,713 B1 | 3/2007 | Verdine et al. | |
| 7,723,469 B2 | 5/2010 | Walensky et al. | |
| 2004/0171809 A1 | 9/2004 | Korsmeyer et al. | |
| 2005/0250680 A1* | 11/2005 | Walensky et al. | 514/9 |
| 2006/0008848 A1 | 1/2006 | Verdine et al. | |
| 2006/0014675 A1 | 1/2006 | Arora et al. | |

FOREIGN PATENT DOCUMENTS
| | | |
|---|---|---|
| WO | WO 9325579 A1 * | 12/1993 |
| WO | WO2005/044839 | 5/2005 |
| WO | WO2007-075534 | 7/2007 |

OTHER PUBLICATIONS

Danial, et al. "Dual role of proapoptotic BAD in insulin secretion and beta cell survival," Nat. Med. 12:144-153 (2008).*
Danial et al., "Dual role of proapoptotic BAD in insulin secretion and beta cell survival," Nat. Med. 12:144-153 (2008).*
Danial et al., "Dual role of proapoptotic BAD in insulin secretion and beta cell survival," Nat. Med. 12:144-153 (2008)—supplemental figures and methdos pp. 1-17.*
Walensky et al., "Activation of apoptosis in vivo by a hydrocarbon-stapled BH3 helix," Science 305:1466-1470 (2004)).*
Albano, J. D. M. et al. "A Sensitive, Precise Radioimmunoassay of Serum Insulin Relying on Charcoal Separation of Bound and Free Hormone Moieties"; Acta Endocrinologica, 1972, pp. 487-509.
Amin et al. "Inhibition of Glucose- and Calcium-Induced Insulin Secretion from βTC3 Cells by Novel Inhibitors of Protein Isoprenylation"; American Laboratory Products Company, The Journal of Pharmacology and Experimental Therapeutics, 2002, vol. 303, pp. 82-88.
Ball et al. "Conformational Constraints: Nonpeptide β-Turn Mimics", Journal of Molecular Recognition, vol. 3, 1990, pp. 55-64.
Belokon et al. "Improved Procedures for the Synthesis of (S)-24N-(Ar-benzylprolyl) amino]benzophenone (BPB) and Ni(II) Complexes of Schiff's Bases Derived from BPB and Amino Acids" Tetrahedron: *Asymmetry* 9, 1998, pp. 4249-4252.
Bernal et al., J. Am. Chem. Soc., 2007, p. 5298.
Bird et al. "Synthesis and Biophysical Characterization of Stabilized α-Helices of BCL-2 Domains", Methods in Enzymology, vol. 446, pp. 369-386.
Böhm et al. "Quantitative Analysis of Protein Far UV Circular Dichroism Spectra by Neural Networks" Protein Engineering, 1992, vol. 5, pp. 191-195.
Bray et al. "Large-Scale Manufacture of Peptide Therapeutics by Chemical Synthesis", Nature Reviews Drug Discovery, Jul. 2003, vol. 2, pp. 587-593.
Charles et al. "Risk Factors of NIDDM in White Population", Diabetes, vol. 40, pp. 796-799.
Chittenden et al. "A Conserved Domain in Bak, Distinct from BH1 and BH2, Mediates Cell Death and Protein Binding Functions", The EMBO Journal, 1995, vol. 14, pp. 5589-5596.

(Continued)

*Primary Examiner* — Julie Ha
*Assistant Examiner* — Kristina M Hellman
(74) *Attorney, Agent, or Firm* — Mintz Levin Cohn Ferris Glovsky and Popeo, P.C.; Peter F. Corless, Esq.; Daniel W. Clarke

(57) ABSTRACT

The present invention provides stably cross-linked insulionotropic polypeptides having superior and unexpected benefits in the treatment of conditions involving abnormal glucose homeostasis, e.g., type 2 diabetes and conditions relating to type 2 diabetes. Such benefits include, but are not limited to, extended polypeptide half-life, enhanced alpha-helicity, improved thermal stability and protease resistance, increased functional activity and pharmacologic properties, improved bioavailability when administered by any route, and improved bioavailability and gastrointestinal absorption when delivered orally, as compared to the corresponding unmodified polypeptides. The invention also provides compositions for administering the polypeptides of the invention, as well as methods for preparing and evaluating the polypeptides of the invention.

21 Claims, 27 Drawing Sheets

(56) References Cited

OTHER PUBLICATIONS

Contillo et al. "Glucagon-like Peptide-1 and Analogs: A Structure/Function Analysis", Proceedings of the 16th American Peptide Symposium; Jun. 26-Jul. 1, 1999, pp. 671-673.
Danial et al. "Dual Role of Proapoptotic BAD in Insulin Secretion and Beta Cell Survival" Nature Medicine, Feb. 2008, vol. 14, pp. 144-153.
Ellenberger et al. "The GCN4 Basic Region Leucine Zipper Binds DNA as a Dimer of Uninterrupted α Helices: Crystal Structure of the Protein-DNA Complex", Dec. 24, 1992, vol. 71, pp. 1223-1237.
Eng et al. "Isolation and Characterization of Exendin-4, an Exendin-3 Analogue, from *Heloderma Suspectum* Venom"; The Journal of Biological Chemistry, Apr. 15, 1992, vol. 267, pp. 7402-7405.
Forood et al. "Stabilization of α-Helical Structures in Short Peptides Via End Capping", PNAS, Feb. 1993, vol. 90, pp. 838-842.
Freidinger, R. M. "Non-Peptide Ligands for Peptide Receptors" Trends Pharmacological Sciences, Jul. 1989, vol. 10, pp. 270-274.
Gavathiotis et al. "BAX Activation is Initiated at a Novel Interaction Site" Nature, Oct. 23, 2008, vol. 455, pp. 1076-1081.
Gavin et al. "Report of the Expert Committee on the Diagnosis and Classification of Diabetes Mellitus", The Expert Committee on Classification of Diabetes Mellitus, Diabetes Care, Jan. 1999, vol. 22, pp. S5-S19.
Gedulin et al. "Pharmacokinetics and Pharmacodynamics of Exenatide Following Alternative Routes of Administration" International Journals of Pharmaceuticals 356, 2008, pp. 231-238.
Green et al. "Stabbed in The Bax" Nature, Oct. 23, 2008, vol. 455, pp. 1047-1049.
Greig et al. "Once Daily Injection of Exendin-4 to Diabetic Mice Achieves Long-Term Beneficial Effects on Blood Glucose Concentrations" Diabetologia, 1999, vol. 42, pp. 45-50.
Grossman, S. "Differentiating Incretin Therapies Based on Structure, Activity, and Metabolism: Focus on Liraglutide" Pharmacotherapy, 2009, vol. 29, pp. 25S-32S.
Gutniak et al. "Antidiabetogenic Effect of Glucagon-Like Peptide-1 (7-36) Amide in Normal Subjects and Patients with Diabetes Mellitus" New England Journal of Medicine, May 14, 1992, pp. 1316-1322.
Herman et al. "Abnormal Insulin Secretion, Not Insulin Resistance, Is the Genetic or Primary Defect of MODY in the RW Pedigree" Diabetes, Jan. 1994, vol. 43, pp. 40-46.
James et al. "Benzodiazepine Peptidomimetics: Potent Inhibitors of Ras Farnesylation in Animal Cells" Science, Jun. 25, 1993, vol. 260, pp. 1937-1942.
Kim et al., "Intorduction of All-Hydrocarbon i, i+3 Staples into a-Helicies via Ring-Closing Olefin Metathesis", Organic Letters, Jul. 2, 2010, vol. 12, No. 13, pp. 3046-3049.
Kussie et al. "Structure of the MDM2 Oncoprotein Bound to the p53 Tumor Suppressor Transactivation Domain" Science, Nov. 8, 1996, vol. 274, pp. 948-953.
Lawless et al. "HIV-1 Membrane Fusion Mechanism: Structural Studies of the Interactions between Biologically-Active Peptides from gp41", Biochemistry, Mar. 22, 1996, vol. 35, pp. 13697-13708.
Liu et al. "Engineering a tRNA and aminoacyl-tRNA synthetase for the site-specific incorporation of unnatural amino acids into proteins in vivo", Proc. Nat. Acad. Sci. USA, Sep. 1997, vol. 94, pp. 10092-10097.
Lupas et al. "Predicting Coiled Coils from Protein Sequences", Science, May 24, 1991, vol. 252, pp. 1162-1164.
Metzger, Boyd E. "Summary and Recommendations of the Third International Workshop-Conference on Gestational Diabetes Mellitus" Diabetes, Dec. 1991, vol. 40, pp. 197-201.
Morgan et al. "Chapter 26, Approaches to the Discovery of Non-Peptide Ligands for Peptide Raptors and Peptidases", Annual Reports in Medicinal Chemistry, 1989, vol. 24, pp. 243-252.
Neumiller, J.J., "Differential chemistry (structure), mechanism of action, and pharmacology of GLP-1 receptor agonists and DPP-4 inhibitors", J. Am. Pharm. Assoc., 2009, vol. 49, suppl. 1, pp. S16-S29.
Penhos et al. "A Rat Pancreas-Small Gut Preparation for the Study of Intestinal Factor(s) and Insulin Release", Diabetes, Nov. 1969, vol. 18, pp. 733-738.
Qiu et al. "Convenient, Large-Scale Asymmetric Synthesis of Enantiomerically Pure *trans*-Cinnamylglycine and -α-Alanine", Tetrahedron 56, 2000, pp. 2577-2582.
Runge et al. "Crystal Structure of the Ligand-bound Glucagon-like Peptide-1 Receptor Extracellular Domain", The Journal of Biological Chemistry, Apr. 25, 2008, vol. 283, pp. 11340-11347.
Schafmeister et al. "An All-Hydrocarbon Cross-Linking System for Enhancing the Helicity and Stability of Peptides" Journal of the American Chemical Society, Jun. 6, 2000, vol. 122, pp. 5891-5892.
Scholtz et al. "Parameters of Helix-Coil Transition Theory for Alanine-Based Peptides of Varying Chain Lengths in Water" Biopolymers, 1991, vol. 31, pp. 1463-1470.
Stewart et al. "The MCI-1 BH3 Helix is an Exclusive MCL-1 Inhibitor and Apoptosis Sensitizer" Nature Chemical Biology, Aug. 2010, vol. 6, pp. 595-601.
Walensky et al. "Activation of Apoptosis In Vivo by a Hydrocarbon-Stapled BH3 Helix" Science, Sep. 3, 2004, vol. 305, pp. 1466-1470.
Walensky et al. "A Stapled BID BH3 Helix Directly Binds and Activates BAX" Molecular Cell 24 Oct. 20, 2006, pp. 199-210.
Weir et al. "Glucagon Secretion from the Perfused Rat Pancreas" Studies With Glucose and Catecholamines, The Journal of Clinical Investigation, Dec. 1974, vol. 54, pp. 1403-1412.
Zimmet et al. "Latent Autoimmune Diabetes Mellitus in Adults (LADA): the Role of Antibodies to Glutamic Acid Decarboxylase in Diagnosis and Prediction of Insulin Dependency" Diabetic Medicine, 1994, pp. 299-303.
Walensky et al., "Hydrocarbon-stapled peptides: principles, practice, and progress." Journal of Medicinal Chemistry, 57: 6275-6288 (2014).

* cited by examiner

FIG. 1A

Exendin-4 [Heloderma suspectum] GI:1916067 (SEQ ID NO: 1)

MKIILWLCVFGLFLATLFPISWQMPVESGLSSEDSASSESFASKIKRHGEGTFTSDLSKQMEEEAVRLFIEWLKNGGPSSGAP
PPSG

Exenatide (SEQ ID NO: 2)

HGEGTFTSDLSKQMEEEAVRLFIEWLKNGGPSSGAPPPS

Gastric Inhibitory Polypeptide Preprotein [Homo sapiens] GI:475843 (SEQ ID NO: 3)

MVATKTFALLLSLFLAVGLGEKKEGHFSALPSLPVGSHAKVSSPQPRGPRYAEGTFISDYSIAMDKIHQQDFVNWLLAQKGK
KNDWKHNITQREARALELASQANRKEEEAVEPQSSPAKNPSDEDLLRDLLIQELLACLLDQTNLCRLRSR

Gastric Inhibitory Peptide (GIP) (SEQ ID NO: 4)

YAEGTFISDYSIAMDKIHQQDFVNWLLAQKGKKNDWKHNITQ

Glucagon-like Peptide 1 Precursor [Homo sapiens] GI:31778 (SEQ ID NO: 5)

MKSIYFVAGLFVMLVQGSWQRSLQDTEEKSRSFSASQADPLSDPDQMNEDKRHSQGTFTSDYSKYLDSRRAQDFVQWLMNTKR
NRNNIAKRHDEFERHAEGTFTSDVSSYLEGQAAKEFIAWLVKGRGRRDFPEEVAIVEELGRRHADGSFSDEMNTILDNLAARD
FINWLIQTKITDR

FIG. 1A (Continued)

Glucagon-like peptide-2 (GLP-2) (SEQ ID NO: 6)

HADGSFSDEMNTILDNLAARDFINWLIQTKITD

Glucagon-like peptide-1 (GLP-1) (SEQ ID NO: 7)

HDEFERHAEGTFTSDVSSYLEGQAAKEFIAWLVKGRGR

GLP-1-(7-37) (SEQ ID NO: 8)

HAEGTFTSDVSSYLEGQAAKEFIAWLVKGRGR

GLP-1-(7-36) (SEQ ID NO: 9)

HAEGTFTSDVSSYLEGQAAKEFIAWLVKGRG

Liraglutide (SEQ ID NO: 10)

HAEGTFTSDVSSYLEGQAAK(E-palm)EFIAWLVRGRG (Arg34Lys26-(N-ε-(γ-Glu(N-α-hexadecanoyl)))-GLP-1[7-37])

FIG. 1A (Continued)

Taspoglutide   (SEQ ID NO: 11)

H2N-His-2-methyl-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-2-methyl-Ala-Arg-CONH2

Albiglutide   (SEQ ID NO: 12)

genetic fusion of albumin and GLP-1

LY2189265

GLP-1 analog linked to a fragment of IgG

FIG. 1B

```
Exenatide    HGEGTFTSDLSKQMEEEAVRLFIEWLKNGGPSSGAPPPS (SEQ ID NO: 2)
GLP-1(7-37)  HAEGTFTSDVSSYLEGQAAKEFIAWLVKGRG        (SEQ ID NO: 8)
Glucagon     HSQGTFTSDYSKYLDSRRAQDFVQWLMNT          (SEQ ID NO: 13)
GLP-2        HADGSFSDEMNTILDNLAARDFINWLIQTKITD      (SEQ ID NO: 6)
GIP          YAEGTFISDYSIAMDKIHQQDFVNWLLAQKGKKNDWKHNITQ (SEQ ID NO: 4)
             1    5    10   15   20   25   30   35
```

Structure of nGLP-1R and Ex4(9-33)

\* \* \* \* \* ^ \* ^ \* \* \* ^ \* ^ \* \* \* \* 
HGEGTFTSDLSKQMEEAVRLFIEWLKNGGPSSGAPPPS      Ex4 (SEQ ID NO:2)

DLSKQMEEAVRLFIEWLKNGGPSS            Ex4 (9-33)(SEQ ID NO:14)

^
            Staple location (CPK)

\* Critical residue from Ala scan (Ball & Stick)

Runge, S et al. 2008 *J Biol Cheml*, 283:11340-11347.

GLP-1 (7-37)
HAEGTFTSDVSSYLEGQAAKEFIAWLVKGRGR (SEQ ID NO: 8)

Interacting Face i,i+3 i,i+4 i,i+7

FIG. 5A
A
i,i+3 and i,i+3
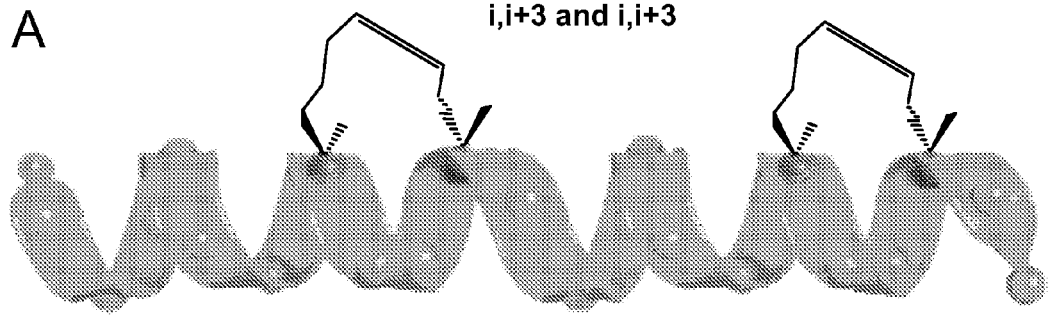
B
i,i+4 and i,i+4
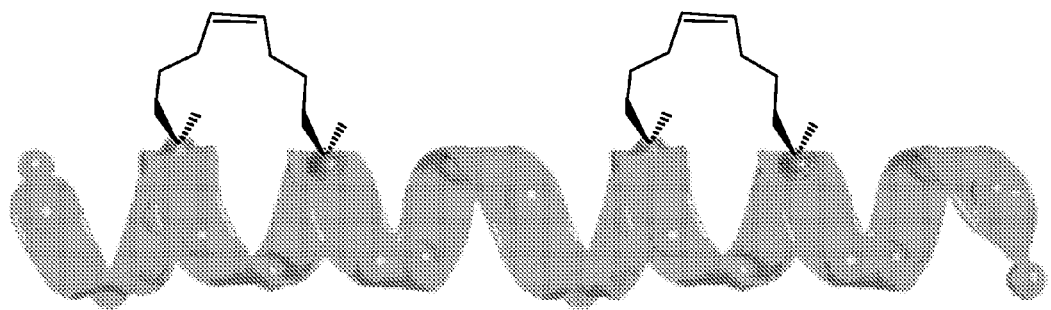
C
i,i+7 and i,i+7
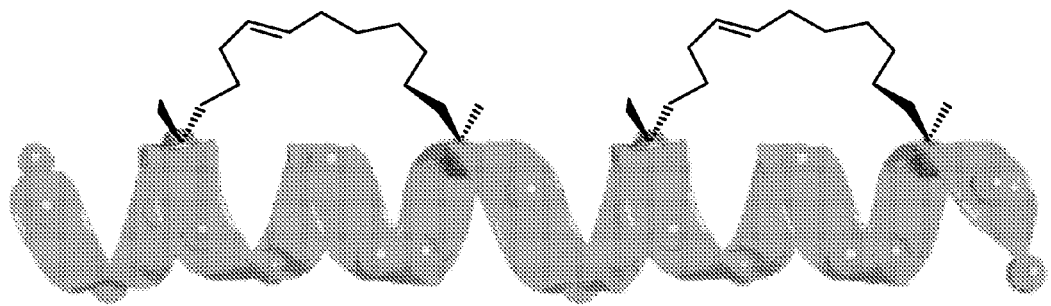
D
i,i+3 and i,i+4
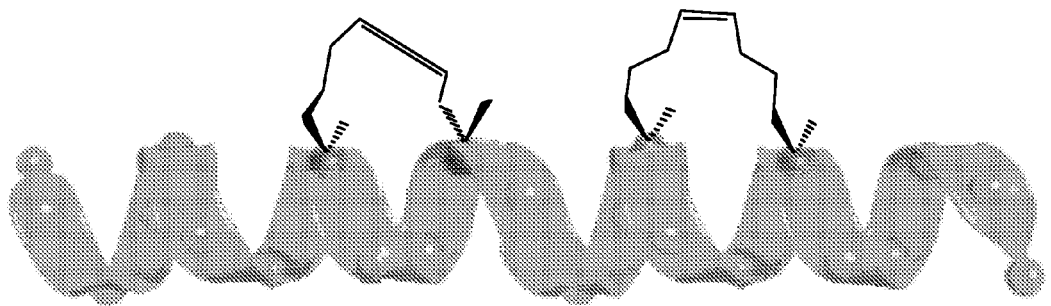

FIG. 5A (Continued)
E
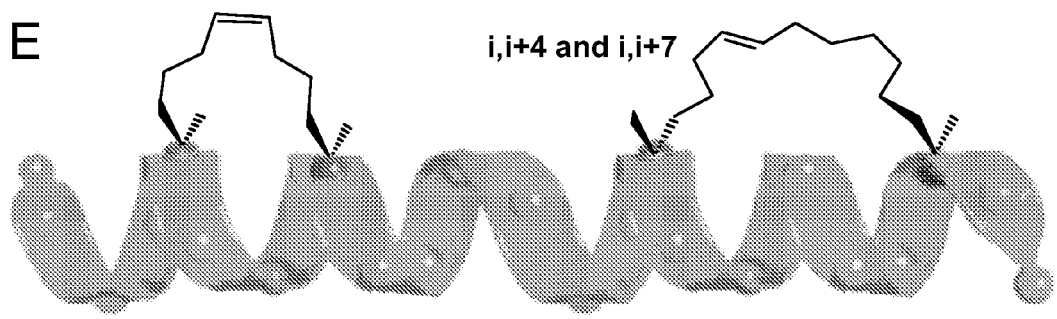
i,i+4 and i,i+7
F
i,i+4 and i,i+4 and i,i+4
G
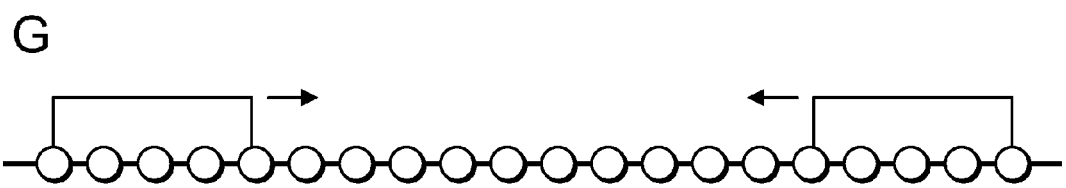
H
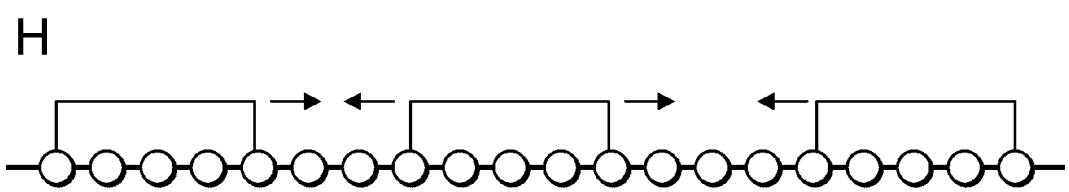

(R)-2-Fmoc-2-methyl-pent-4-enoic acid (S)-2-Fmoc-2-methyl-oct-7-enoic acid

FIG. 7A

SAH-Ex Peptides

| Sequence | SEQ ID |
|---|---|
| HGEGTFTSDLSKQBEEEAVRLFIEWLKNGGPSSGAPPPS | (SEQ ID NO: 2) |
| HGEGTFTSDLSKQBEEEAVRLFIXWLKX̲I̲NGGPSSGAPPPS | (SEQ ID NO: 15) |
| HGEGTFTSDLSKQBEEEAVRLFIXWLKX̲I̲NGGPSSGAPPPS | (SEQ ID NO: 16) |
| HGEGTFTSDLSKQBEEEAVRLFIXWLKX̲I̲NGGPSSGAPPPS | (SEQ ID NO: 17) |
| HGEGTFTSDLSKQBEEEAVRX̲F̲IEWLKX̲I̲NGGPSSGAPPPS | (SEQ ID NO: 18) |
| HGEGTFTSDLSKQBEEEAVRX̲F̲IXWLKX̲I̲NGGPSSGAPPPS | (SEQ ID NO: 19) |
| HGEGTFTSDX̲S̲KQBEEEAVRX̲F̲IEWLKNGGPSSGAPPPS | (SEQ ID NO: 20) |
| HGEGTFTSDX̲S̲KQX̲I̲EEAVRLFIEWLKNGGPSSGAPPPS | (SEQ ID NO: 21) |
| HGEGX̲F̲TX̲D̲LSKQBEEEAVRLFIEWLKNGGPSSGAPPPS | (SEQ ID NO: 22) |
| HGEGX̲F̲TSDLSKQX̲I̲EEAVRLFIEWLKNGGPSSGAPPPS | (SEQ ID NO: 23) |
| HGEGTFTSDX̲S̲KQBEEEAVRX̲F̲IXWLKX̲I̲NGGPSSGAPPPS | (SEQ ID NO: 24) |
| HGEGTFTSDX̲S̲KQBEEEAVRX̲F̲IXWLKX̲I̲NGGPSSGAPPPS | (SEQ ID NO: 25) |
| HGEGTFTSDX̲S̲KQBEEEAVRX̲F̲IXWLKX̲I̲NGGPSSGAPPPS | (SEQ ID NO: 26) |
| HGEGTFTSDX̲S̲KQBEEEAVRX̲F̲IXWLKX̲I̲NGGPSSGAPPPS | (SEQ ID NO: 27) |
| HGEGTFTSDX̲S̲KQBEEEAVRX̲F̲IXWLKX̲I̲NGGPSSGAPPPS | (SEQ ID NO: 28) |
| HGEGTFTSDX̲S̲KQBEEEAVRX̲F̲IXWLKX̲I̲NGGPSSGAPPPS | (SEQ ID NO: 29) |
| HGEGTFTSDX̲S̲KQBEEEAVRX̲F̲IXWLKX̲I̲NGGPSSGAPPPS | (SEQ ID NO: 30) |
| HGEGX̲F̲TX̲D̲LSKQBEEEAVRX̲F̲IXWLKX̲I̲NGGPSSGAPPPS | (SEQ ID NO: 31) |
| HGEGX̲F̲TX̲D̲LSKQBEEEAVRX̲F̲IXWLKX̲I̲NGGPSSGAPPPS | (SEQ ID NO: 32) |
| HGEGX̲F̲TX̲D̲LSKQBEEEAVRX̲F̲IXWLKX̲I̲NGGPSSGAPPPS | (SEQ ID NO: 33) |
| HGEGX̲F̲TX̲D̲LSKQBEEEAVRX̲F̲IXWLKX̲I̲NGGPSSGAPPPS | (SEQ ID NO: 34) |
| HGEGX̲F̲TSDLSX̲Q̲X̲I̲EEAVRLFIXWLKX̲I̲NGGPSSGAPPPS | (SEQ ID NO: 35) |
| HGEGX̲F̲TSDLSX̲Q̲X̲I̲EEAVRLFIXWLKX̲I̲NGGPSSGAPPPS | (SEQ ID NO: 36) |
| HGEGX̲F̲TSDLSX̲Q̲X̲I̲EEAVRLFIXWLKX̲I̲NGGPSSGAPPPS | (SEQ ID NO: 37) |
| HGEGX̲F̲TSDLSX̲Q̲X̲I̲EEAVRLFIXWLKX̲I̲NGGPSSGAPPPS | (SEQ ID NO: 38) |

FIG. 7A (Continued)

SAH-GLP1(7-37)

```
HAEGTFTSDVSSYLEGQAAKEFIXWLVXGRGR    (SEQ ID NO:39)
HAEGTFTSDVSSYLEGQAAKEFIXWLXKGRGR    (SEQ ID NO:40)
HAEGTFTSDVSSYLEGQAAKXFIAWLVXGRGR    (SEQ ID NO:41)
HAEGTFTSDVSSYLEGQAAKXFIXWLVKGRGR    (SEQ ID NO:42)
HAEGTFTSDXSSYLEGXAAKEFIAWLVKGRGR    (SEQ ID NO:43)
HAEGTFTSDXSSYXEGQAAKEFIAWLVKGRGR    (SEQ ID NO:44)
HAEGXFTXDVSSYLEGQAAKEFIAWLVKGRGR    (SEQ ID NO:45)
HAEGXFTSDVSXYLEGQAAKEFIAWLVKGRGR    (SEQ ID NO:46)
HAEGTFTSDXSSYLEGXAAKEFIXWLVXGRGR    (SEQ ID NO:47)
HAEGTFTSDXSSYLEGXAAKEFIXWLXKGRGR    (SEQ ID NO:48)
HAEGTFTSDXSSYLEGXAAKXFIAWLVXGRGR    (SEQ ID NO:49)
HAEGTFTSDXSSYLEGXAAKXFIXWLVKGRGR    (SEQ ID NO:50)
HAEGTFTSDXSSYXEGQAAKEFIXWLVXGRGR    (SEQ ID NO:51)
HAEGTFTSDXSSYXEGQAAKEFIXWLXKGRGR    (SEQ ID NO:52)
HAEGTFTSDXSSYXEGQAAKXFIAWLVXGRGR    (SEQ ID NO:53)
HAEGTFTSDXSSYXEGQAAKXFIXWLVKGRGR    (SEQ ID NO:54)
HAEGXFTXDVSSYLEGQAAKEFIXWLVXGRGR    (SEQ ID NO:55)
HAEGXFTXDVSSYLEGQAAKEFIXWLXKGRGR    (SEQ ID NO:56)
HAEGXFTXDVSSYLEGQAAKXFIAWLVXGRGR    (SEQ ID NO:57)
HAEGXFTXDVSSYLEGQAAKXFIXWLVKGRGR    (SEQ ID NO:58)
HAEGXFTSDVSXYLEGQAAKEFIXWLVXGRGR    (SEQ ID NO:59)
HAEGXFTSDVSXYLEGQAAKEFIXWLXKGRGR    (SEQ ID NO:60)
HAEGXFTSDVSXYLEGQAAKXFIAWLVXGRGR    (SEQ ID NO:61)
HAEGXFTSDVSXYLEGQAAKXFIXWLVKGRGR    (SEQ ID NO:62)
HXEGTFTSXVSSYLEGQAAKEFIAWLVKGRGR    (SEQ ID NO:63)
HAXGTFTSDXSSYLEGQAAKEFIAWLVKGRGR    (SEQ ID NO:64)
HAEXTFTSDVXSYLEGQAAKEFIAWLVKGRGR    (SEQ ID NO:65)
HAEGTFTSDVSXYLEXQAAKEFIAWLVKGRGR    (SEQ ID NO:66)
HAEGTFTSDVSSYLEGQAAXEFIAWLXKGRGR    (SEQ ID NO:67)
```

Ex (SEQ ID NO: 2)         HGEGTFTSDLSKQBEEEAVRLFIEWLKNGGPSSGAPPPS

SAH-Ex(A) (SEQ ID NO:20)  HGEGTFTSDXSKQXEEEAVRLFIEWLKNGGPSSGAPPPS
                                     A

SAH-Ex(B) (SEQ ID NO:15)  HGEGTFTSDLSKQBEEEAVRLFIXWLKXGGPSSGAPPPS
                                                         B

SAH-Ex(A,B) (SEQ ID NO:27) HGEGTFTSDXSKQXEEEAVRLFIXWLKXGGPSSGAPPPS
                                     A              B

FIG. 9  Chymotrypsin, pH 7
| Compound | Half-Life, min. | Fold Enhancement |
|---|---|---|
| Ex | 38 | 1 |
| SAH-Fx(A) | 94 | 2 |
| SAH-Fx(B) | 128 | 3 |
| SAH-Fx(A,B) | 295 | 8 |
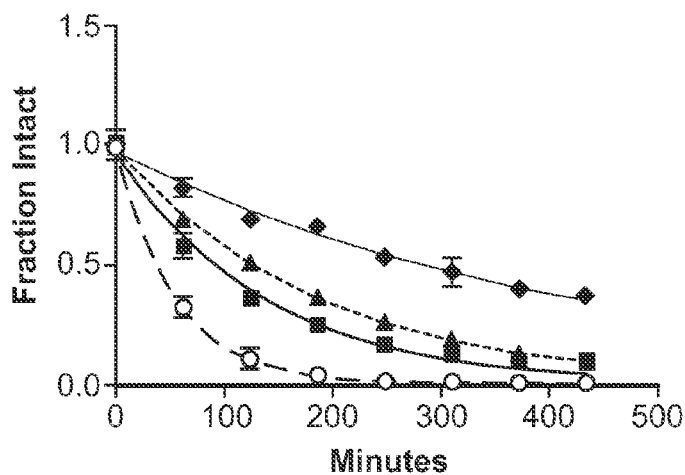
FIG. 10  Pepsin, pH 2
| Compound | Half-Life, min. | Fold Enhancement |
|---|---|---|
| Ex | 13 | 1 |
| SAH-Fx(A) | 8 | 1 |
| SAH-Fx(B) | 81 | 6 |
| SAH-Fx(A,B) | 172 | 13 |
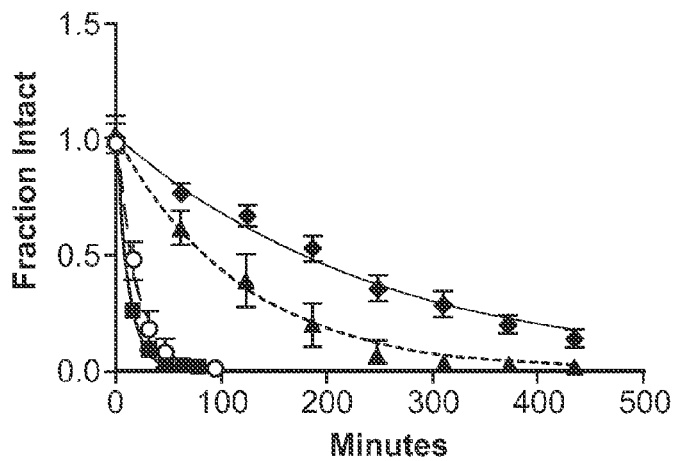

30 min, 125 μg (4 mg/kg)

FIG. 13C

Chymotrypsin Cleavage Sites (actual)

| Compound | Sequence |
|---|---|
| T649v(626-662) | BTWBEWDREINNYTSLIHSLIEESQNQQEKNEQELLE (SEQ ID NO:63) |
| SAH-gp41(626-662)(A) | BTWBEWDREINNYTSLIHSLIEESQNQQEKNEQELLE (SEQ ID NO:64) |
| SAH-gp41(626-662)(B) | BTWBEWDREINNYTSLIHSLIEESQNQXEKNXQELLE (SEQ ID NO:65) |
| SAH-gp41(626-662)(A,B) | BTWXEWDXEINNYTSLIHSLIEESQNQXEKNXQELLE (SEQ ID NO:66) |
| UAH-gp41(626-662)(A,B) | BTWXEWDXEINNYTSLIHSLIEESQNQXEKNXQELLE (SEQ ID NO:67) |

FIG. 13D
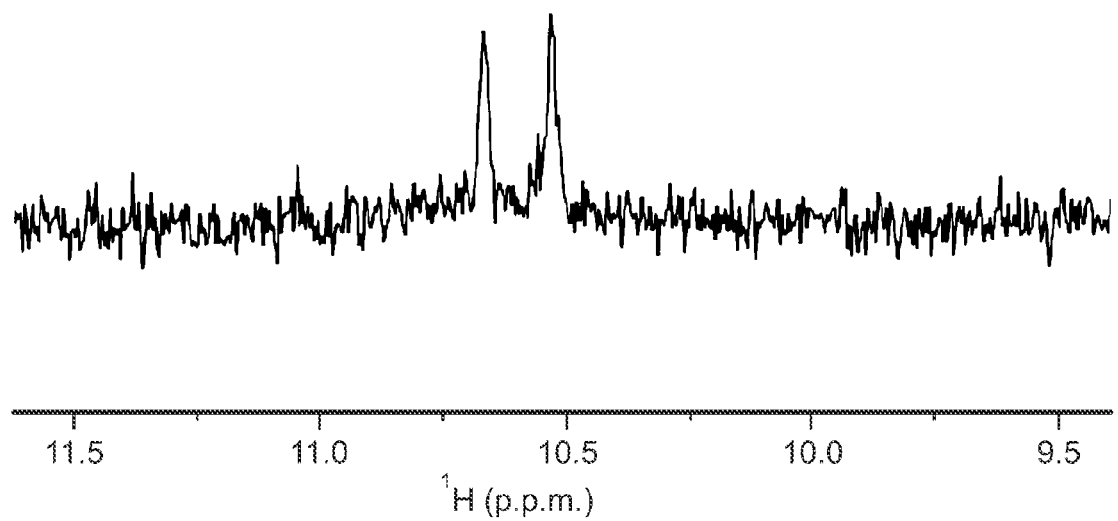
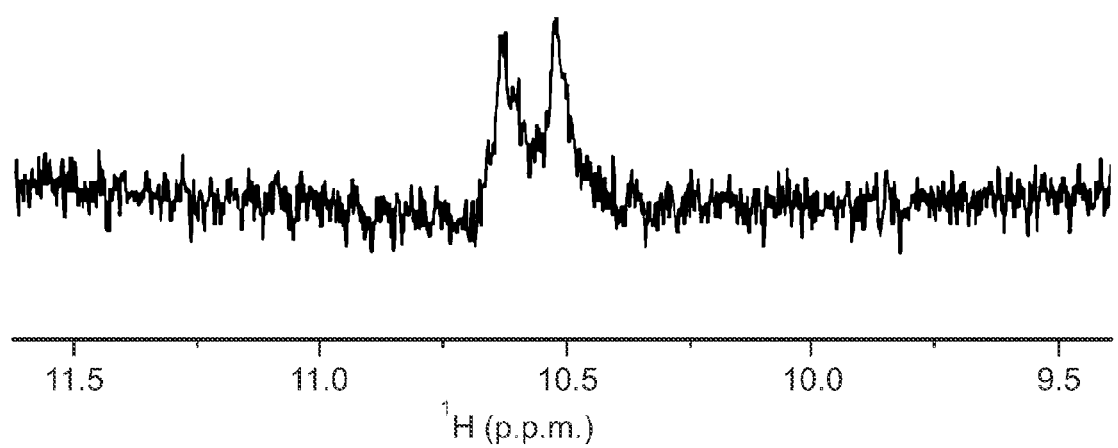

FIG. 14A

| Name | Sequence | Seq ID | Fold-Enhancement of GSIS Over Vehicle |
|---|---|---|---|
| Ex4(9-39) | HGEGTFTSDLSKQBEEEAVRLFIEWLKNGGPSSGAPPPS | (SEQ ID NO:2) | 11.5 |
| SAH-Ex4(9-39)(A) | HGEGTFTSDXSKQXEEEAVRLFIEWLKNGGPSSGAPPPS | (SEQ ID NO:20) | 9.2 |
| SAH-Ex4(9-39)(B) | HGEGTFTSDLSKQBEEEAVRLFIXWLKXGGPSSGAPPPS | (SEQ ID NO:15) | 10.9 |
| SAH-Ex4(9-39)(A,B) | HGEGTFTSDXSKQXEEEAVRLFIXWLKXGGPSSGAPPPS | (SEQ ID NO:27) | 7.7 |
| SAH-Ex4(9-39)(C) | HGEGXFTXDLSKQBEEEAVRLFIEWLKNGGPSSGAPPPS | (SEQ ID NO:21) | 0.8 |
| SAH-Ex4(9-39)(D) | HGEGXFTSDLSXQBEEEAVRLFIEWLKNGGPSSGAPPPS | (SEQ ID NO:22) | 1.3 |
| SAH-Ex4(9-39)(E) | HGEGTFTSDXSKQBEEXAVRLFIEWLKNGGPSSGAPPPS | (SEQ ID NO:19) | 9.2 |
| SAH-Ex4(9-39)(F) | HGEGTFTSDLSKQBEEEAVRXFIXWLKNGGPSSGAPPPS | (SEQ ID NO:18) | 3.3 |
| SAH-Ex4(9-39)(G) | HGEGTFTSDLSKQBEEEAVRXFIEWLKXXGGPSSGAPPPS | (SEQ ID NO:17) | 4.5 |
| SAH-Ex4(9-39)(H) | HGEGTFTSDLSKQBEEEAVRLFIXWLXNGGPSSGAPPPS | (SEQ ID NO:16) | ND |

FIG. 14B

| Name | Sequence | Seq ID | Fold-Enhancement of GSIS Over Vehicle |
|---|---|---|---|
| GLP1(7-38) | HAEGTFTSDVSSYLEGQAAKEFIAWLVKGRGR | (SEQ ID NO:39) | 7.7 |
| SAH-GLP1(7-38)(A) | HX̲EGTFTSX̲VSSYLEGQAAKEFIAWLVKGRGR | (SEQ ID NO:63) | ND |
| SAH-GLP1(7-38)(B) | HAX̲GTFTSDX̲SSYLEGQAAKEFIAWLVKGRGR | (SEQ ID NO:64) | ND |
| SAH-GLP1(7-38)(C) | HAEX̲TFTSDVX̲SYLEGQAAKEFIAWLVKGRGR | (SEQ ID NO:65) | ND |
| SAH-GLP1(7-38)(D) | HAEGX̲FTX̲DVSSYLEGQAAKEFIAWLVKGRGR | (SEQ ID NO:45) | 1.0 |
| SAH-GLP1(7-38)(E) | HAEGX̲FTSX̲VSSYLEGQAAKEFIAWLVKGRGR | (SEQ ID NO:46) | 0.7 |
| SAH-GLP1(7-38)(F) | HAEGTFTSDX̲SSYX̲EGQAAKEFIAWLVKGRGR | (SEQ ID NO:44) | ND |
| SAH-GLP1(7-38)(G) | HAEGTFTSDX̲SSYLEGX̲AAKEFIAWLVKGRGR | (SEQ ID NO:48) | 6.8 |
| SAH-GLP1(7-38)(H) | HAEGTFTSDVSSX̲LEX̲QAAKEFIAWLVKGRGR | (SEQ ID NO:66) | 4.7 |
| SAH-GLP1(7-38)(I) | HAEGTFTSDVSSYLEGQAAX̲EFIAWLX̲GRGR | (SEQ ID NO:67) | ND |
| SAH-GLP1(7-38)(J) | HAEGTFTSDVSSYLEGQAAKX̲FIX̲WLVKGRGR | (SEQ ID NO:42) | 4.2 |
| SAH-GLP1(7-38)(K) | HAEGTFTSDVSSYLEGQAAKX̲FIAWLX̲GRGR | (SEQ ID NO:41) | 3.3 |
| SAH-GLP1(7-38)(L) | HAEGTFTSDVSSYLEGQAAKEFIX̲WLX̲KGRGR | (SEQ ID NO:40) | 3.0 |
| SAH-GLP1(7-38)(M) | HAEGTFTSDVSSYLEGQAAKEFIX̲WLVX̲GRGR | (SEQ ID NO:39) | 1.1 |

SEQUENCE LISTING

<160> NUMBER OF SEQ ID NOS: 75

<210> SEQ ID NO 1
<211> LENGTH: 87
<212> TYPE: PRT
<213> ORGANISM: Heloderma suspectum

<400> SEQUENCE: 1

Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu Glu
    50                  55                  60

Ala Val Arg Leu Phe Ile Glu Trp Leu Lys Asn Gly Gly Pro Ser Ser
65                  70                  75                  80

Gly Ala Pro Pro Pro Ser Gly
                85

<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 153
<212> TYPE: PRT
<213> ORGANISM: Homo sapiens

<400> SEQUENCE: 3

Met Val Ala Thr Lys Thr Phe Ala Leu Leu Leu Ser Leu Phe Leu Leu
1               5                   10                  15

Ala Val Gly Leu Gly Glu Lys Lys Glu Gly His Phe Ser Ala Leu Pro
            20                  25                  30

Ser Leu Pro Val Gly Ser His Ala Lys Val Ser Ser Pro Gln Pro Arg
        35                  40                  45

Gly Pro Arg Tyr Ala Glu Gly Thr Phe Ile Ser Asp Tyr Ser Ile Ala
    50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
            85                  90                  95

Arg Ala Leu Glu Leu Ala Ser Gln Ala Asn Arg Lys Glu Glu Glu Ala
            100                 105                 110

Val Glu Pro Gln Ser Ser Pro Ala Lys Asn Pro Ser Asp Glu Asp Leu
        115                 120                 125

```
Leu Arg Asp Leu Leu Ile Gln Glu Leu Leu Ala Cys Leu Leu Asp Gln
            130                 135                 140

Thr Asn Leu Cys Arg Leu Arg Ser Arg
145                 150
```

<210> SEQ ID NO 4
<211> LENGTH: 42
<212> TYPE: PRT
<213> ORGANISM: Homo sapiens

<400> SEQUENCE: 4

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
                20                  25                  30

Lys Asn Asp Trp Lys His Asn Ile Thr Gln
                35                  40
```

<210> SEQ ID NO 5
<211> LENGTH: 179
<212> TYPE: PRT
<213> ORGANISM: Homo sapiens

<400> SEQUENCE: 5

```
Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
                20                  25                  30

Phe Ser Ala Ser Gln Ala Asp Pro Leu Ser Asp Pro Asp Gln Met Asn
                35                  40                  45

Glu Asp Lys Arg His Ser Gln Gly Thr Phe Thr Ser Asp Tyr Ser Lys
                50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
                100                 105                 110

Gly Gln Ala Ala Lys Glu Phe Ile Ala Trp Leu Val Lys Gly Arg Gly
                115                 120                 125

Arg Arg Asp Phe Pro Glu Glu Val Ala Ile Val Glu Glu Leu Gly Arg
            130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg
```

<210> SEQ ID NO 6
<211> LENGTH: 33
<212> TYPE: PRT
<213> ORGANISM: Homo sapiens

<400> SEQUENCE: 6

```
His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
```

```
                        20                  25                  30

Asp

<210> SEQ ID NO 7
<211> LENGTH: 38
<212> TYPE: PRT
<213> ORGANISM: Homo sapiens

<400> SEQUENCE: 7

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly Arg
        35

<210> SEQ ID NO 8
<211> LENGTH: 31
<212> TYPE: PRT
<213> ORGANISM: Homo sapiens

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 9
<211> LENGTH: 30
<212> TYPE: PRT
<213> ORGANISM: Homo sapiens

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Glu-palm

<400> SEQUENCE: 10

His Ala Glu Gly Thr Phe Thr Ser Asp Val Ser Ser Tyr Leu Glu Gly
1               5                   10                  15

Gln Ala Ala Lys Glu Glu Phe Ile Ala Trp Leu Val Arg Gly Arg Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: 2-methyl Ala
<220> FEATURE:
<221> NAME/KEY: MOD_RES
<222> LOCATION: (29)..(29)
<223> OTHER INFORMATION: 2-methyl Ala

<400> SEQUENCE: 11

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Ala Arg
            20                  25                  30

<210> SEQ ID NO 12

<400> SEQUENCE: 12

000

<210> SEQ ID NO 13
<211> LENGTH: 29
<212> TYPE: PRT
<213> ORGANISM: Homo sapiens

<400> SEQUENCE: 13

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 14
<211> LENGTH: 25
<212> TYPE: PRT
<213> ORGANISM: Heloderma suspectum

<400> SEQUENCE: 14

Asp Leu Ser Lys Gln Met Glu Glu Glu Ala Val Arg Leu Phe Ile Glu
1               5                   10                  15

Trp Leu Lys Asn Gly Gly Pro Ser Ser
            20                  25

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 15

His Gly Glu Gly Thr Phe Thr Ser Asp Leu Ser Lys Gln Xaa Glu Glu
```

```
1               5                   10                  15
Glu Ala Val Arg Leu Phe Ile Xaa Trp Leu Lys Xaa Gly Gly Pro Ser
            20                  25                  30

Ser Gly Ala Pro Pro Ser
            35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 16

His Gly Glu Gly Thr Phe Thr Ser Asp Leu Ser Lys Gln Xaa Glu Glu
1               5                   10                  15

Glu Ala Val Arg Leu Phe Ile Xaa Trp Leu Xaa Asn Gly Gly Pro Ser
            20                  25                  30

Ser Gly Ala Pro Pro Ser
            35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 17

His Gly Glu Gly Thr Phe Thr Ser Asp Leu Ser Lys Gln Xaa Glu Glu
1               5                   10                  15

Glu Ala Val Arg Xaa Phe Ile Glu Trp Leu Lys Xaa Gly Gly Pro Ser
            20                  25                  30

Ser Gly Ala Pro Pro Ser
            35
```

```
<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 18

His Gly Glu Gly Thr Phe Thr Ser Asp Leu Ser Lys Gln Xaa Glu Glu
1               5                   10                  15

Glu Ala Val Arg Xaa Phe Ile Xaa Trp Leu Lys Asn Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (17)..(17)
<223> OTHER INFORMATION: Any non-natural amino acid

<400> SEQUENCE: 19

His Gly Glu Gly Thr Phe Thr Ser Asp Xaa Ser Lys Gln Xaa Glu Glu
1               5                   10                  15

Xaa Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid

<400> SEQUENCE: 20

His Gly Glu Gly Thr Phe Thr Ser Asp Xaa Ser Lys Gln Xaa Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine

<400> SEQUENCE: 21

His Gly Glu Gly Xaa Phe Thr Xaa Asp Leu Ser Lys Gln Xaa Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
```

```
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine

<400> SEQUENCE: 22

His Gly Glu Gly Xaa Phe Thr Ser Asp Leu Ser Xaa Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 23

His Gly Glu Gly Thr Phe Thr Ser Asp Xaa Ser Lys Gln Xaa Glu Glu
1               5                   10                  15

Xaa Ala Val Arg Leu Phe Ile Xaa Trp Leu Lys Xaa Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
```

```
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 24

His Gly Glu Gly Thr Phe Thr Ser Asp Xaa Ser Lys Gln Xaa Glu Glu
1               5                   10                  15

Xaa Ala Val Arg Leu Phe Ile Xaa Trp Leu Xaa Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 25

His Gly Glu Gly Thr Phe Thr Ser Asp Xaa Ser Lys Gln Xaa Glu Glu
1               5                   10                  15

Xaa Ala Val Arg Xaa Phe Ile Glu Trp Leu Lys Xaa Gly Gly Pro Ser
            20                  25                  30
```

```
                    20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 26

His Gly Glu Gly Thr Phe Thr Ser Asp Xaa Ser Lys Gln Xaa Glu Glu
1               5                   10                  15

Xaa Ala Val Arg Xaa Phe Ile Xaa Trp Leu Lys Asn Gly Gly Pro Ser
                20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
```

<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 27

His Gly Glu Gly Thr Phe Thr Ser Asp Xaa Ser Lys Gln Xaa Glu Glu
1               5                   10                  15

Glu Ala Val Arg Leu Phe Ile Xaa Trp Leu Lys Xaa Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 28

His Gly Glu Gly Thr Phe Thr Ser Asp Xaa Ser Lys Gln Xaa Glu Glu
1               5                   10                  15

Glu Ala Val Arg Leu Phe Ile Xaa Trp Leu Xaa Asn Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:

-continued

```
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 29

His Gly Glu Gly Thr Phe Thr Ser Asp Xaa Ser Lys Gln Xaa Glu Glu
1               5                   10                  15

Glu Ala Val Arg Xaa Phe Ile Glu Trp Leu Lys Xaa Gly Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 30

His Gly Glu Gly Thr Phe Thr Ser Asp Xaa Ser Lys Gln Xaa Glu Glu
1               5                   10                  15

Glu Ala Val Arg Xaa Phe Ile Xaa Trp Leu Lys Asn Gly Gly Pro Ser
            20                  25                  30

Ser Gly Ala Pro Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 31

His Gly Glu Gly Xaa Phe Thr Xaa Asp Leu Ser Lys Gln Xaa Glu Glu
1               5                   10                  15

Glu Ala Val Arg Leu Phe Ile Xaa Trp Leu Lys Xaa Gly Gly Pro Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 32
```

```
His Gly Glu Gly Xaa Phe Thr Xaa Asp Leu Ser Lys Gln Xaa Glu Glu
1               5                   10                  15

Glu Ala Val Arg Leu Phe Ile Xaa Trp Leu Xaa Asn Gly Gly Pro Ser
            20                  25                  30

Ser Gly Ala Pro Pro Pro Ser
        35
```

<210> SEQ ID NO 33
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 33

```
His Gly Glu Gly Xaa Phe Thr Xaa Asp Leu Ser Lys Gln Xaa Glu Glu
1               5                   10                  15

Glu Ala Val Arg Xaa Phe Ile Glu Trp Leu Lys Xaa Gly Gly Pro Ser
            20                  25                  30

Ser Gly Ala Pro Pro Pro Ser
        35
```

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES

```
<222> LOCATION: (14)..(14)
<223> OTHER INFORMATION: Norleucine
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 34

His Gly Glu Gly Xaa Phe Thr Xaa Asp Leu Ser Lys Gln Xaa Glu Glu
1               5                   10                  15

Glu Ala Val Arg Xaa Phe Ile Xaa Trp Leu Lys Asn Gly Gly Pro Ser
            20                  25                  30

Ser Gly Ala Pro Pro Pro Ser
            35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 35

His Gly Glu Gly Xaa Phe Thr Ser Asp Leu Ser Xaa Gln Xaa Glu Glu
1               5                   10                  15

Glu Ala Val Arg Leu Phe Ile Xaa Trp Leu Lys Xaa Gly Gly Pro Ser
            20                  25                  30

Ser Gly Ala Pro Pro Pro Ser
            35

<210> SEQ ID NO 36
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 36

His Gly Glu Gly Xaa Phe Thr Ser Asp Leu Ser Xaa Gln Xaa Glu Glu
1               5                   10                  15

Glu Ala Val Arg Leu Phe Ile Xaa Trp Leu Xaa Asn Gly Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid
```

-continued

<400> SEQUENCE: 37

His Gly Glu Gly Xaa Phe Thr Ser Asp Leu Ser Xaa Gln Xaa Glu Glu
1               5                   10                  15

Glu Ala Val Arg Xaa Phe Ile Glu Trp Leu Lys Xaa Gly Gly Pro Ser
            20                  25                  30

Ser Gly Ala Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (14)..(14)
<223> OTHER INFORMATION: Norleucine
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 38

His Gly Glu Gly Xaa Phe Thr Ser Asp Leu Ser Xaa Gln Xaa Glu Glu
1               5                   10                  15

Glu Ala Val Arg Xaa Phe Ile Xaa Trp Leu Lys Asn Gly Gly Pro Ser
            20                  25                  30

Ser Gly Ala Pro Pro Ser
        35

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)

<223> OTHER INFORMATION: Any non-natural amino acid

<400> SEQUENCE: 39

His Ala Glu Gly Thr Phe Thr Ser Asp Val Ser Ser Tyr Leu Glu Gly
1               5                   10                  15

Gln Ala Ala Lys Glu Phe Ile Xaa Trp Leu Val Xaa Gly Arg Gly Arg
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 40

His Ala Glu Gly Thr Phe Thr Ser Asp Val Ser Ser Tyr Leu Glu Gly
1               5                   10                  15

Gln Ala Ala Lys Glu Phe Ile Xaa Trp Leu Xaa Lys Gly Arg Gly Arg
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 41

His Ala Glu Gly Thr Phe Thr Ser Asp Val Ser Ser Tyr Leu Glu Gly
1               5                   10                  15

Gln Ala Ala Lys Xaa Phe Ile Ala Trp Leu Val Xaa Gly Arg Gly Arg
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)

<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 42

His Ala Glu Gly Thr Phe Thr Ser Asp Val Ser Ser Tyr Leu Glu Gly
1               5                   10                  15

Gln Ala Ala Lys Xaa Phe Ile Xaa Trp Leu Val Lys Gly Arg Gly Arg
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any non-natural amino acid

<400> SEQUENCE: 43

His Ala Glu Gly Thr Phe Thr Ser Asp Xaa Ser Ser Tyr Leu Glu Gly
1               5                   10                  15

Xaa Ala Ala Lys Glu Phe Ile Ala Trp Leu Val Lys Gly Arg Gly Arg
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid

<400> SEQUENCE: 44

His Ala Glu Gly Thr Phe Thr Ser Asp Xaa Ser Ser Tyr Xaa Glu Gly
1               5                   10                  15

Gln Ala Ala Lys Glu Phe Ile Ala Trp Leu Val Lys Gly Arg Gly Arg
            20                  25                  30

<210> SEQ ID NO 45
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid

<400> SEQUENCE: 45

His Ala Glu Gly Xaa Phe Thr Xaa Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid

<400> SEQUENCE: 46

His Ala Glu Gly Xaa Phe Thr Ser Asp Val Ser Xaa Tyr Leu Glu Gly
1               5                   10                  15

Gln Ala Ala Lys Glu Phe Ile Ala Trp Leu Val Lys Gly Arg Gly Arg
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
```

```
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 47

His Ala Glu Gly Thr Phe Thr Ser Asp Xaa Ser Ser Tyr Leu Glu Gly
1               5                   10                  15

Xaa Ala Ala Lys Glu Phe Ile Xaa Trp Leu Val Xaa Gly Arg Gly Arg
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 48

His Ala Glu Gly Thr Phe Thr Ser Asp Xaa Ser Ser Tyr Leu Glu Gly
1               5                   10                  15

Xaa Ala Ala Lys Glu Phe Ile Xaa Trp Leu Xaa Lys Gly Arg Gly Arg
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any non-natural amino acid
<220> FEATURE:
```

```
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 49

His Ala Glu Gly Thr Phe Thr Ser Asp Xaa Ser Ser Tyr Leu Glu Gly
1               5                   10                  15

Xaa Ala Ala Lys Xaa Phe Ile Ala Trp Leu Val Xaa Gly Arg Gly Arg
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (17)..(17)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 50

His Ala Glu Gly Thr Phe Thr Ser Asp Xaa Ser Ser Tyr Leu Glu Gly
1               5                   10                  15

Xaa Ala Ala Lys Xaa Phe Ile Xaa Trp Leu Val Lys Gly Arg Gly Arg
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
```

<222> LOCATION: (14)..(14)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 51

His Ala Glu Gly Thr Phe Thr Ser Asp Xaa Ser Ser Tyr Xaa Glu Gly
1               5                   10                  15

Gln Ala Ala Lys Glu Phe Ile Xaa Trp Leu Val Xaa Gly Arg Gly Arg
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 52

His Ala Glu Gly Thr Phe Thr Ser Asp Xaa Ser Ser Tyr Xaa Glu Gly
1               5                   10                  15

Gln Ala Ala Lys Glu Phe Ile Xaa Trp Leu Xaa Lys Gly Arg Gly Arg
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)

```
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 53

His Ala Glu Gly Thr Phe Thr Ser Asp Xaa Ser Ser Tyr Xaa Glu Gly
1               5                   10                  15

Gln Ala Ala Lys Xaa Phe Ile Ala Trp Leu Val Xaa Gly Arg Gly Arg
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any non-natural amino acid
<220> FEATURE:
<221> NAME/KEY: misc_feature
<222> LOCATION: (10)..(14)
<223> OTHER INFORMATION: Crosslink between residues
<220> FEATURE:
<221> NAME/KEY: MOD_RES
<222> LOCATION: (14)..(14)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 54

His Ala Glu Gly Thr Phe Thr Ser Asp Xaa Ser Ser Tyr Xaa Glu Gly
1               5                   10                  15

Gln Ala Ala Lys Xaa Phe Ile Xaa Trp Leu Val Lys Gly Arg Gly Arg
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
```

```
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 55

His Ala Glu Gly Xaa Phe Thr Xaa Asp Val Ser Ser Tyr Leu Glu Gly
1               5                   10                  15

Gln Ala Ala Lys Glu Phe Ile Xaa Trp Leu Val Xaa Gly Arg Gly Arg
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 56

His Ala Glu Gly Xaa Phe Thr Xaa Asp Val Ser Ser Tyr Leu Glu Gly
1               5                   10                  15

Gln Ala Ala Lys Glu Phe Ile Xaa Trp Leu Xaa Lys Gly Arg Gly Arg
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 57

His Ala Glu Gly Xaa Phe Thr Xaa Asp Val Ser Ser Tyr Leu Glu Gly
1               5                   10                  15

Gln Ala Ala Lys Xaa Phe Ile Ala Trp Leu Val Xaa Gly Arg Gly Arg
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 58

His Ala Glu Gly Xaa Phe Thr Xaa Asp Val Ser Ser Tyr Leu Glu Gly
1               5                   10                  15

Gln Ala Ala Lys Xaa Phe Ile Xaa Trp Leu Val Lys Gly Arg Gly Arg
            20                  25                  30

<210> SEQ ID NO 59
<211> LENGTH: 32
<212> TYPE: PRT
<213> ORGANISM: Artificial Sequence
<220> FEATURE:
```

-continued

```
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 59

His Ala Glu Gly Xaa Phe Thr Ser Asp Val Ser Xaa Tyr Leu Glu Gly
1               5                   10                  15

Gln Ala Ala Lys Glu Phe Ile Xaa Trp Leu Val Xaa Gly Arg Gly Arg
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (24)..(24)
<223> OTHER INFORMATION: Any non-natural amino acid
<220> FEATURE:
<221> NAME/KEY: misc_feature
<222> LOCATION: (24)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 60

His Ala Glu Gly Xaa Phe Thr Ser Asp Val Ser Xaa Tyr Leu Glu Gly
1               5                   10                  15

Gln Ala Ala Lys Glu Phe Ile Xaa Trp Leu Xaa Lys Gly Arg Gly Arg
            20                  25                  30

<210> SEQ ID NO 61
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (28)..(28)
<223> OTHER INFORMATION: Any non-natural amino acid

<400> SEQUENCE: 61

His Ala Glu Gly Xaa Phe Thr Ser Asp Val Ser Xaa Tyr Leu Glu Gly
1               5                   10                  15

Gln Ala Ala Lys Xaa Phe Ile Ala Trp Leu Val Xaa Gly Arg Gly Arg
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: MOD_RES
<222> LOCATION: (21)..(21)
<223> OTHER INFORMATION: Any non-natural amino acid
<220> FEATURE:
<221> NAME/KEY: misc_feature
<222> LOCATION: (21)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any non-natural amino acid

<400> SEQUENCE: 62

His Ala Glu Gly Xaa Phe Thr Ser Asp Val Ser Xaa Tyr Leu Glu Gly
1               5                   10                  15

Gln Ala Ala Lys Xaa Phe Ile Xaa Trp Leu Val Lys Gly Arg Gly Arg
            20                  25                  30
```

```
<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any non-natural amino acid
<220> FEATURE:
<221> NAME/KEY: misc_feature
<222> LOCATION: (2)..(9)
<223> OTHER INFORMATION: Crosslink between residues
<220> FEATURE:
<221> NAME/KEY: MOD_RES
<222> LOCATION: (9)..(9)
<223> OTHER INFORMATION: Any non-natural amino acid

<400> SEQUENCE: 63

His Xaa Glu Gly Thr Phe Thr Ser Xaa Val Ser Ser Tyr Leu Glu Gly
1               5                   10                  15

Gln Ala Ala Lys Glu Phe Ile Ala Trp Leu Val Lys Gly Arg Gly Arg
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any non-natural amino acid
<220> FEATURE:
<221> NAME/KEY: misc_feature
<222> LOCATION: (3)..(10)
<223> OTHER INFORMATION: Crosslink between residues
<220> FEATURE:
<221> NAME/KEY: MOD_RES
<222> LOCATION: (10)..(10)
<223> OTHER INFORMATION: Any non-natural amino acid

<400> SEQUENCE: 64

His Ala Xaa Gly Thr Phe Thr Ser Asp Xaa Ser Ser Tyr Leu Glu Gly
1               5                   10                  15

Gln Ala Ala Lys Glu Phe Ile Ala Trp Leu Val Lys Gly Arg Gly Arg
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (11)..(11)
<223> OTHER INFORMATION: Any non-natural amino acid
```

```
<400> SEQUENCE: 65

His Ala Glu Xaa Thr Phe Thr Ser Asp Val Xaa Ser Tyr Leu Glu Gly
1               5                   10                  15

Gln Ala Ala Lys Glu Phe Ile Ala Trp Leu Val Lys Gly Arg Gly Arg
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any non-natural amino acid
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: Any non-natural amino acid

<400> SEQUENCE: 66

His Ala Glu Gly Thr Phe Thr Ser Asp Val Ser Xaa Tyr Leu Glu Xaa
1               5                   10                  15

Gln Ala Ala Lys Glu Phe Ile Ala Trp Leu Val Lys Gly Arg Gly Arg
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Any non-natural amino acid
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any non-natural amino acid

<400> SEQUENCE: 67

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Xaa Lys Gly Arg Gly Arg
            20                  25                  30

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Gly Glu Gly Thr Phe Thr Ser Asp Leu Ser Lys Gln Met Glu Glu
1               5                   10                  15
```

-continued

Glu Ala Val Arg Leu Phe Ile Glu Trp Leu Lys Asn
            20                  25

<210> SEQ ID NO 69
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Norleucine

<400> SEQUENCE: 69

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (4)..(4)
<223> OTHER INFORMATION: Norleucine

<400> SEQUENCE: 70

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)

<223> OTHER INFORMATION: Any non-natural amino acid

<400> SEQUENCE: 71

Xaa Thr Trp Xaa Glu Trp Asp Xaa Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (28)..(28)
<223> OTHER INFORMATION: Any non-natural amino acid
<220> FEATURE:
<221> NAME/KEY: misc_feature
<222> LOCATION: (28)..(32)
<223> OTHER INFORMATION: Crosslink between residues
<220> FEATURE:
<221> NAME/KEY: MOD_RES
<222> LOCATION: (32)..(32)
<223> OTHER INFORMATION: Any non-natural amino acid

<400> SEQUENCE: 72

Xaa Thr Trp Xaa Glu Trp Asp Arg Glu Ile Asn Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES

```
<222> LOCATION: (28)..(28)
<223> OTHER INFORMATION: Any non-natural amino acid
<220> FEATURE:
<221> NAME/KEY: misc_feature
<222> LOCATION: (28)..(32)
<223> OTHER INFORMATION: Crosslink between residues
<220> FEATURE:
<221> NAME/KEY: MOD_RES
<222> LOCATION: (32)..(32)
<223> OTHER INFORMATION: Any non-natural amino acid

<400> SEQUENCE: 73

Xaa Thr Trp Xaa Glu Trp Asp Xaa Glu Ile Asn Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (4)..(4)
<223> OTHER INFORMATION: Any non-natural amino acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any non-natural amino acid
<220> FEATURE:
<221> NAME/KEY: MOD_RES
<222> LOCATION: (28)..(28)
<223> OTHER INFORMATION: Any non-natural amino acid
<220> FEATURE:
<221> NAME/KEY: misc_feature
<222> LOCATION: (28)..(32)
<223> OTHER INFORMATION: Crosslink between residues
<220> FEATURE:
<221> NAME/KEY: MOD_RES
<222> LOCATION: (32)..(32)
<223> OTHER INFORMATION: Any non-natural amino acid

<400> SEQUENCE: 74

Xaa Thr Trp Xaa Glu Trp Asp Xaa Glu Ile Asn Asn Tyr Thr Ser Leu
1               5                   10                  15

Ile His Ser Leu Ile Glu Glu Ser Gln Asn Gln Xaa Glu Lys Asn Xaa
            20                  25                  30

Gln Glu Leu Leu Glu
        35

<210> SEQ ID NO 75
<211> LENGTH: 32
<212> TYPE: PRT
<213> ORGANISM: Homo sapiens
```

```
<400> SEQUENCE: 75

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30
```

… # STABILIZED INSULINOTROPIC PEPTIDES AND METHODS OF USE

REFERENCE TO RELATED APPLICATIONS AND INCORPORATION BY REFERENCE

Cross-Reference to Related Applications

This application is a 35 U.S.C. §371 U.S. national entry of International Application PCT/US2011/043465 (WO 2012/006598) having an International filing date of Jul. 8, 2011 which claims priority to U.S. Provisional Application Ser. No. 61/363,097, filed Jul. 9, 2010. This application is also related to PCT International Application No. PCT/US2009/000438, filed Jan. 23, 2009 and entitled "Compositions and Methods for the Treatment of Viral Infections," and PCT International Application No. PCT/US2010/039223, filed Jun. 18, 2010 and entitled "Structured Viral Peptide Compositions and Method of Use," which in turn claims priority from U.S. Provisional Patent Application Ser. No. 61/218,209, filed on Jun. 18, 2009. Each of the aforementioned applications are herein incorporated by reference in their entireties.

Any and all references cited in the text of this patent application, including any U.S. or foreign patents or published patent applications, International patent applications, as well as, any non-patent literature references, including any manufacturer's instructions, are hereby expressly incorporated herein by reference.

BACKGROUND

Diabetes refers to a disease process resulting in abnormal glucose homeostasis that is derived from multiple causative factors and characterized by elevated levels of glucose in the blood (i.e., hyperglycemia). Persistent or uncontrolled hyperglycemia is associated with increased and premature morbidity and mortality. Often abnormal glucose homeostasis is also associated both directly and indirectly with alterations of the lipid, lipoprotein and apolipoprotein metabolism and other metabolic and hemodynamic diseases. Therefore patients with type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Problems with compliance of various known antidiabetic agents also exist due to a lack of overwhelming patient acceptance of injection as the main mode of delivery.

With type 2 diabetes, increasing the plasma level of insulin by administration of sulfonylureas (e.g. tolbutamide and glipizide) or meglitinide, which stimulate the pancreatic beta-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of type 2 diabetes.

Despite these known therapies, there is no generally applicable and consistently effective means of maintaining an essentially normal fluctuation in glucose levels in type 2 diabetes. Additional methods of treating the disease, including alternative therapeutic interventions (e.g., incretin-based therapies, such as GLP-1-receptor agonists and DPP-4 inhibitors) and improved modes of pharmacologic administration (e.g., sublingual, intranasal, intratracheal, inhalation, and oral administration) to improve drug utility and compliance, are still under investigation.

The incretin system—a recognized possible point of intervention for diabetic therapies—includes glucagon-like peptide (GLP-1) and glucose-dependent insulinotropic polypeptide (GIP) ("incretins"), which together play an important role in the regulation of insulin secretion by the pancreas and glucose production by the liver. In addition, the incretins are recognized as playing an important role in maintaining pancreatic β-cell mass and differentiation, preventing β-cell apoptosis, decreased glucagon secretion, deceleration of gastric emptying, and promotion of early satiety leading to weight loss.

Normal glucose levels in the blood are, in part, regulated by a balance of the actions of insulin (causes a reduction in blood glucose) and glucagon (signals liver to produce glucose). The balanced action between these two hormones is maintained in a normal individual through pancreatic β-cell production of insulin and glucagon in response to plasma glucose levels. The incretins provide an additional layer of regulation on glucose levels which is triggered at the time of food ingestion. GLP-1 and GIP are released from cells of the intestine upon food intake, which stimulate insulin secretion via GLP-1-receptors and GIP receptors on precreatic cells, and in the case of GLP-1, also which inhibits glucagon secretion from the pancreas, thereby decreasing glucose production by the liver and lowering blood glucose levels overall.

In type 2 diabetes, however, incretin system is greatly diminished. Specifically, the insulinotropic and glucagon-reducing effects of GLP-1 and GIP are impaired in individuals with type 2 diabetes. This recognition led to the recent development of incretin-based therapies, including GLP-1-receptor agonists, such as liraglutide and others, and incretin mimetics, such as exenatide, which interact with the GLP-1 receptor and other receptors of the incretin system to promote insulin release and block glucagon secretion, thereby lowering the overall plasma glucose level. See Gutniak, M., et al. N. Engl. J. Bled. 1992; 326:1316-1322; Grossman, S., "Differentiating incretin therapies based on structure, activity, and metabolism: Focus on Liraglutide," Pharmacotherapy, 2009; 29(12):25S-32S.

One incretin-based therapy under development includes the GLP-1-receptor agonist and GLP-1 analog, glucagon-like insulinotropic peptide (GLIP), which is a fragment of GLP-1. Gutniak et al., 1992. In normal subjects, the infusion of GLIP significantly lowered the meal-related increases in blood glucose concentration, and the plasma concentrations of insulin and glucagon. In patients with NIDDM, the treatment reduced the requirement for insulin by 8 fold. In patients with IDDM, the GLIP treatment lowered the insulin required by one half. This glucose-dependent activity is a very desirable characteristic for a therapeutic agent that can be used to treat type 2 diabetes while avoiding complications of hypoglycemic side effects.

A more recently developed incretin-based therapy for treating type 2 diabetes is exenatide, which was approved by the Federal Food and Drug Administration (FDA) as a subcutaneous injection (under the skin) of the abdomen, thigh, or arm, 30 to 60 minutes before the first and last meal of the day. Exenatide—a synthetic version of exendin-4, a hormone found in the saliva of the Gila monster that was first isolated by Dr. John Eng in 1992 (Eng, J. et al., J. Biol. Chem. 267: 742-7405 (1992)) and described in U.S. Pat. No. 5,424,286 to Eng displays human glucagon-like peptide-1 (GLP-1) activities, functioning as a regulator of glucose metabolism and as an insulinotropic agent (i.e., increases insulin release) through its agonistic action at the GLP-1-receptor.

According to the FDA package insert, exenatide enhances glucose-dependent insulin secretion by the pancreatic β-cells, suppresses inappropriately elevated glucagon secretion, and slows gastric emptying, although the mechanism of action is still under study. Exenatide is a 39-amino-acid peptide and an insulin secretagogue with glucoregulatory effects which binds and activates the pancreatic GLP-1 receptor (GLP-1R) with similar affinity and potency as GLP-1 and thereby promotes insulin secretion and blocks glucagon secretion in a glucose-dependent manner. The effects of exenatide also reportedly include slowing of gastric emptying to modulate nutrient absorption, reduction of food intake and body weight and increased pancreatic β-cell mass and function. In addition, it is inherently a poor substrate for degradation by dipeptidyl peptidase-IV (DPP-IV)—the normal degradative enzyme responsible for removal of the incretins (GLP-1 and GIP). Exenatide was approved by the FDA on Apr. 28, 2005 for patients whose diabetes was not well-controlled on other oral antibiabetic agents (e.g. metformin, sulfonylureas, thiazolidinediones).

Exenatide raises insulin levels quickly (within about ten minutes of administration) with the insulin levels subsiding substantially over the next hour or two. A dose taken after meals has a much smaller effect on blood sugar than one taken beforehand. The effects on blood sugar diminish after 6-8 hours. The medicine is available in two doses: 5 mcg and 10 mcg. Treatment often begins with the 5 mcg dosage, which is increased if adverse effects are not significant.

Two important limitations on the use of exenatide and other incretin-based polypeptide antidiabetic therapeutics potentially include (1) relatively short half-lives upon administration (e.g., exenatide's 2.5 hour half life when delivered by the approved intravenous route) due to proteolytic degradation and (2) lack of effective, but less invasive (and thereby more patient compliant), alternative administration routes (e.g., orally, sublingually, or intranasally) that provide for sufficient bioavailability (Gedulin et al., "Pharmacokinetics and pharmacodynamics of exenatide following alternative routes of administration," Int'l J Pharmaceuticals, 356 (2008) 231-238).

Accordingly, the development of optimized incretin-based or other insulinotropic polypeptide therapeutics, such as, optimized exenatide, that are imparted with superior stability, protease resistance, and pharmacologic properties, as well as the development of such therapeutics that can be delivered successfully (i.e., achieving improved bioavailability, gastrointestinal absorption and pharmacologic properties) by alternative, more patient compliant delivery routes (e.g., orally deliverable form of exenatide) would be significant advances in the art.

SUMMARY OF THE INVENTION

The present invention is based, in part, on the surprising discovery that stably crosslinking a polypeptide having an insulinotropic activity, including incretin hormones (e.g., glucagon-like peptide-1), incretin analogs (e.g., liraglutide) or incretin mimetics (e.g., exenatide), provide superior and unexpected benefits in the treatment of conditions involving abnormal glucose homeostasis, e.g., type 2 diabetes and conditions relating to type 2 diabetes. Such benefits include, but are not limited to, extended half-life, enhanced alpha-helicity, improved thermal stability and protease resistance, increased functional activity and pharmacologic properties, improved bioavailability when administered by any route, and improved bioavailability and gastrointestinal absorption when delivered orally, as compared to uncrosslinked counterparts. Thus, the invention provides a new and advantageous approach to the administration of insulinotropic polypeptides that provides benefits not previously obtained or available. Accordingly, the present invention enables improved half-life (and thus, bioavailability, effectiveness, etc.) of insulinotropic polypeptides delivered by injection-based routes. Additionally, the instant invention makes it feasible to deliver effective amounts (i.e., which are bioavailable upon delivery) of insulinotropic polypeptide agents (e.g., GIP, GLP-1, GLP-2, exenatide, liraglutide, taspoglutide, or albiglutide) via non-injection-based routes, including oral, intranasal, and sublingual routes, thereby improving the chances of better patient compliance and ease of use.

Accordingly, in one aspect, the invention provides structurally-fortified insulinotropic polypeptide agents, including incretin hormones (e.g., glucagon-like peptide-1), analogs (e.g., liraglutide) or mimetics (e.g., exenatide) for use in treating or preventing type 2 diabetes and conditions associated with type 2 diabetes, wherein said agents possess extended half-life, enhanced alpha-helicity, improved thermal stability and protease resistance, increased functional activity and pharmacologic properties, and improved bioavailability when administered by any route.

In another aspect, the present invention provides methods and compositions for structurally-fortifying insulinotropic polypeptide agents, including incretin hormones, analogs and mimetics (e.g., exenatide) to impart an extended half-life, enhanced alpha-helicity, improved thermal stability and protease resistance, increased functional activity and pharmacologic properties, and improved bioavailability when administered by any route.

In yet another aspect, the present invention provides therapeutic methods for treating or preventing type 2 diabetes or conditions associated with type 2 diabetes by administering a therapeutically effective amount of a insulinotropic polypeptide agent of the invention via any route (e.g., as injectable or oral agent). The insulinotropic polypeptide agents of the invention can include or be based on full-length incretin hormones, analogs or mimetics, or any suitable functional fragment or variant thereof which retains biological activity.

In yet another embodiment, the invention provides structurally constrained polypeptides having amino acids 1-39 of the exenatide. In certain embodiments, the amino acids 1 to 39 of the exenatide peptide can be contiguous amino acids in the primary sequence of the peptide. In certain embodiments, the amino acids are adjacent to each other e.g., the amino acids are present on the same face of the helix, in at least one native state of the peptide sequence in the context of the full length polypeptide. For example, the adjacent amino acids can be present in a single stacked column of amino acids in a helix, or in adjacent stacks of amino acids in a single face of the structured helix. In an embodiment, the structurally constrained polypeptides include at least one modification from the group consisting of: hydrocarbon staple, amino acid mutation, and non-natural amino acid incorporation. In certain embodiments, the structurally constrained polypeptides include 2, 3, 4, 5 or more modifications. In certain embodiments, the constrained polypeptides comprise various hydrocarbon staples including, but not limited to, pairing selected from the group consisting of an S5-S5 pairing (ie. i, i+4), an S5-R8 pairing (i.e. i, i+7), an S8-R5 pairing (i.e. i, i+7), an R3-S6 pairing (ie. i, i+3), an R6-S3 pairing (ie. i, i+3), an R3-S5 pairing (ie. i, i+3), an R5-S3 pairing (ie. i, i+3), or combinations of pairings within the polypeptide sequence.

In another embodiment, amino acids 1 to 39 of exenatide comprises at least 3 contiguous amino acids, or at least two amino acids on a single face of a helix, or at least two interacting face amino acids; or a conservative substitution thereof. A single face of a helix comprises one, two, three, or four adjacent stacked columns of amino acids wherein the stacked columns of amino acids are defined by positions a, d, and g; positions b and e; or positions c and f; in an alpha helix having 7 amino acids per two turns wherein the amino acids are consecutively and serially assigned positions a-g (see, e.g., FIG. 3); and positions a and d; positions b and e; or positions c and f in a $3^{10}$ helix having 2 amino acids per two turns wherein the amino acids are consecutively and serially assigned positions a-f; or homologues thereof.

The invention in other embodiments provides exenatide and other bioactive insulinotropic polypeptides for use in the invention. The structurally constrained exenatide peptides of the invention can include amino acids 1-39 of SEQ ID NO: 1 comprising a hydrocarbon staple between positions 24 and 28 (i.e., SAH-Ex(B) of FIG. 7B) and optionally a hydrocarbon staple between positions 10 and 14 (i.e., SAH-Ex(A) of FIG. 7B) and at least 3 contiguous amino acids, or at least two amino acids on a single face of a helix, or at least two interacting face amino acids of GLP-1 (see FIG. 2A) or homologues thereof. The structurally constrained peptides of the invention can include the exenatide or GLP-1 sequence only, or the exenatide or GLP-1 sequence flanked on the C-terminus, or the N-terminus, or both. The peptides provided by the invention can further include non-amino acid modifications in addition to modifications to structurally constrain the peptides. For example, peptides can include functional groups for targeting of the peptides in vivo, or to alter the pharmacokinetic and/or pharmacodynamic properties of the peptide. Such modifications are known in the art.

Amino acid positions that constitute a stacked column of amino acids can be defined by positions corresponding to positions on a peptide sequence helical wheel of SEQ ID NO: 1 (see FIG. 3). The sequence of the structurally constrained peptide can be aligned with the sequences of other homologous insulinotropic peptides, including GIPP, GIP, GLP-1 precursor, GLP-1, GLP-2, liraglutide, taspoglutide, and albiglutide Methods for performing sequence alignments are well known to those of skill in the art. Further, corresponding amino acids in helices can be determined using any of a number of publicly available coil detection programs. In reference to the sequence provided in SEQ ID NO: 1, the stacked columns of amino acids can include those depicted in FIG. 3.

The invention also provides polypeptides having at least 3 interacting face amino acids or a conservative substitution of an interacting face amino acid, from the exenatide polypeptide sequence of SEQ ID NO: 1, or homologues thereof. The interacting face of the polypeptide is a single face of the peptide wherein the interacting face amino acids are selected from positions corresponding to amino acids from SEQ ID NO:1 such as H1, D9, F22, I23, and L26, or other critical residues known to be important for biological activity such as G4, F6, T7, G30, P31, P36, P37, P38, as defined by structural determination (PDB ID 3C5T) and/or alanine scanning of SEQ ID NO: 1. The structurally constrained peptides provided by the invention can include additional amino acid sequences, either other sequences from exenatide or other insulinotropic polypeptides. The additional amino acid sequences may or may not be structurally constrained. The invention provides for the use of exenatide or homologous sequences having at least 3 contiguous amino acids of an exenatide or homologous peptide, or at least two amino acids on a single face of a helix of an exenatide or homologous peptide, or at least two interacting face amino acids of an exenatide or homologous peptide; or a conservative substitution thereof. A single face of a helix of the exenatide or homologous peptide includes one, two, three, or four adjacent stacked columns of amino acids wherein the stacked column of amino acids is defined by positions a, d, and g; positions b and e; or positions c and f; in an alpha helix, wherein position a is an amino acid in the helix, and the amino acids are consecutively and serially assigned letters a through g in an alpha helix; or homologues thereof.

For example, an alpha-helix and a stacked column of amino acids of a peptide is defined as positions 1, 4, 5, 8, 11, 12, 15, 18, 19, 22, 25, 26, 29, 32, and 33; or positions 2, 5, 6, 9, 12, 13, 16, 19, 20, 23, 26, 27, 30, 33, and 34; or positions 3, 6, 7, 10, 13, 14, 17, 20, 21, 24, 27, 28, 31, and 34; or positions 4, 7, 8, 11, 14, 15, 18, 21, 22, 25, 28, 29, 32, and 35; or positions 5, 8, 9, 12, 15, 16, 19, 22, 23, 26, 29, 30, and 33; or positions 6, 9, 10, 13, 16, 17, 20, 23, 24, 27, 30, 31, and 34; or 7, 10, 11, 14, 17, 18, 21, 24, 25, 28, 31, 32, and 35 of SEQ ID NO: 1 or homologues thereof. As provided herein, a single face of a peptide having an alpha-helical structure can include one, two, three, or four adjacent stacked columns of amino acids.

The invention further provides peptides having the interacting face amino acids of the exenatide or homologous peptide. The interacting face is an example of one face on the helical peptides provided by the instant invention. Amino acids of an interacting face include amino acids corresponding to positions such as H1, G2, T5, S8, D9, K12, E15, E16, V19, R20, F22, I23, L26, K27 of SEQ ID NO:1 or may be further limited to amino acids corresponding to positions H1, D9, F22, I23, and L26 on SEQ ID NO: 1.

In further embodiments, the invention provides any of the structurally constrained peptides of the invention in a pharmaceutically acceptable carrier. The invention further provides a peptide of the invention in a pharmaceutical carrier in a unit dosage form. The invention provides structurally constrained peptides of the invention functionally linked to a carrier. In certain embodiments, the carrier includes a protein or lipid to alter the pharmacokinetics and/or pharmacokinetic properties of the structurally constrained peptide. In certain embodiments, the structurally constrained peptide of the composition is functionally linked to a carrier protein in a specified orientation as established by a site-directed linkage.

In still further embodiments, the invention provides methods for the prevention, amelioration, or treatment of type 1 or type 2 diabetes, for example in a subject, by administration of a structurally constrained peptide of the invention to the subject in a therapeutically effective amount. The method can further include one or more of identifying a subject as being in need of prevention, amelioration, or treatment of diabetes, or monitoring the subject for the prevention, amelioration, or treatment of diabetes. In certain embodiments, the invention provides methods of prevention, amelioration, and treatment of diabetes wherein the method includes at least one of promoting euglycemia by enhancing insulin release.

The invention provides for the preparation of a medicament including a structurally constrained peptide of the invention delivered by injection, inhalation, or orally to promote euglycemia. The medicaments can be for the prevention and/or treatment of diabetes.

In certain embodiments, the invention provides kits including at least one of a structurally constrained peptide of the invention and instructions for use.

In one aspect, the invention provides a structurally-fortified insulinotropic polypeptide comprising an alpha helix and one or more molecular tethers, wherein each molecular tether covalently couples a single pair of residues residing on the alpha helix of said polypeptide, thereby structurally fortifying the insulinotropic polypeptide.

In another aspect, the present invention provides a pharmaceutical composition comprising a structurally-fortified insulinotropic polypeptide of the invention and one or more pharmaceutically acceptable excipients.

In still a further aspect, the invention provides a method for treating or preventing diabetes comprising administering a therapeutically effective amount of a structurally-fortified insulinotropic polypeptide of the invention or a composition comprising a structurally-fortified insulinotropic polypeptide of the invention.

In an embodiment, the structurally-fortified insulinotropic polypeptide of the invention can be exenatide, GIPP, GIP, GLP-1 precursor, GLP-1, GLP-2, GLP-1 (7-37), GLP-1-(7-36), liraglutide, taspoglutide, albiglutide or LY2189265.

In another embodiment, the structurally-fortified insulinotropic polypeptide of the invention can be exenatide.

In yet another embodiment, the number of molecular tethers per polypeptide can be between 1-2, 2-3, 2-4, 2-5, 2-6, 2-7, 2-8, 2-9 or 2-10.

In still another embodiment, the at least one residue pair resides within the N-terminal half of the polypeptide.

The at least one residue pair can reside within the C-terminal half of the polypeptide.

The at least one residue pair can reside at any position along the polypeptide.

In yet another embodiment, the polypeptide comprises at least one coupled residue pair within the C-terminal half of the polypeptide and another coupled residue within the N-terminal half of the polypeptide.

In still another embodiment, the polypeptide corresponds to an exenatide having any one of SEQ ID NOs: 2 or 15-38.

In still a further embodiment, the polypeptide corresponds to an GLP-1 having any one of SEQ ID NOs: 39-62.

In another embodiment, the polypeptide has a first molecular tether located at position (i, i+3), or (i, i+4) or (i, i+7) relative to the residue positions of the alpha helix of the polypeptide. The polypeptide may have a second molecular tether located at position (i, i+3), or (i, i+4) or (i, i+7) relative to the residue positions of the alpha helix of the polypeptide, with the proviso that the first and second molecular tethers are not located at identical positions.

In certain embodiments, where at least two molecular tethers are employed, the at least two molecular tethers may be configured in a "stitched" arrangement. Molecular tethers which are "stitched" refers to where sequentially-arranged linkages are made from a common origin. That is, the use of "stitched" cross-links is where double linkages are made from a common origin (e.g., X1, X5, and X9, where X5 is the anchor point for both staples). Thus, the invention encompasses the incorporation of one or more crosslinks within a polypeptide sequence to either further stabilize the sequence or facilitate the structural stabilization, proteolytic resistance, thermal stability, acid stability, pharmacologic properties, and biological activity enhancement of longer polypeptide stretches. FIG. 5B shows an embodiment of polypeptides having multiple cross-links or molecular tethers which are in a "stitched" configuration.

Accordingly, in an embodiment, the tethered polypeptides of the invention may comprise a pair of molecular tethers in a stitched configuration whereby the end of the first molecular tether and the beginning of the second molecular tether originate at a common residue in the polypeptide.

In still another embodiment, the fortified polypeptide possesses a half-life that is at least 2-fold, or 3-fold, or even 8-fold greater than the half-life of a non-fortified counterpart polypeptide.

In yet another embodiment, the fortified polypeptide possesses a resistance to chymotrypsin in vitro that is at least 2-fold greater, or 3-fold greater, or event 8-fold greater than the resistance to chymotrypsin in vitro of a non-fortified counterpart polypeptide.

In still another embodiment, the fortified polypeptide possesses a resistance to chymotrypsin in vitro that is at least 6-fold greater, or 13-fold greater than the resistance to chymotrypsin in vitro of a non-fortified counterpart polypeptide.

In a still further embodiment, the fortified polypeptide possesses a resistance to a serum protease in vivo that is at least 2-fold, or 5-fold or 10-fold greater than the resistance to the serum protease in vivo of a non-fortified counterpart polypeptide.

In certain embodiments, the method of treating diabetes of the invention involves administering the polypeptides of the invention via an oral delivery route.

In certain other embodiments, the method of treating diabetes of the invention involves administering the polypeptides of the invention via an injection-based delivery route.

Other embodiments of the invention will be understood base on the disclosure provided infra.

BRIEF DESCRIPTION OF THE DRAWINGS

The following Detailed Description, given by way of example, but not intended to limit the invention to specific embodiments described, may be understood in conjunction with the accompanying drawings, in which:

FIG. 1 (A) provides the polypeptide sequences of the insulinotropic polypeptide agents, exendin-4, exenatide, Gastric Inhibitory Polypeptide Preprotein (GIPP), Gastric Inhibitory Peptide (GIP), Glucagon-like Peptide-1 Precursor (GLP-1P), Glucagon-like Peptide-1 (GLP-1), Glucagon-like Peptide-2 (GLP-2), fragments of GLP-1, liraglutide, taspoglutide, albiglutide and LY2189265, which are exemplary insulinotropic polypeptides that can be used as templates in various embodiments of the invention for structural fortification by hydrocarbon stapling. (B) provides a sequence alignment of the human glucagon peptide subfamily, highlighting critical amino acid residues that interact with GLP-1 receptor and conserved residues. The residues of exendin-4(9-39) that interact with GLP-1R are shown in bold (i.e., 15E, 19V, 20K, 22F, 23I, 26L, 27K, 32S). Conserved residues are outlined with a box (i.e., residue positions 4, 6, 21, 24, 25). Positions where only four residues are conserved are shaded gray (i.e., positions 1, 5, 8, 9, 11). (Runge S et al. 2008 J Biol Chem 283:11340-11347).

FIG. 5A shows how multiple staples of similar or different compositions can be inserted along the length of the peptide alpha-helix to generated doubly, triply, or multiply stapled peptides. Staples can be located at (i, i+3), (i, i+4), and (i, i+7) positions along the length of the peptide helix to generate a library of multiply stapled peptides (i.e. "staple scan") to identify optimal positioning for the desired biophysical and biological properties. (A-F) Examples of multiply stapled peptides using various combinations of i, i+3, i, i+4, and i, i+7 crosslinks. (G, H) The optimal staple positions for achieving the desired biophysical, biological, and pharmacologic properties can be identified by staple scanning, which involves the sequential evaluation of discrete staple positions in combination along the length of the peptide sequence template. (G) A double i, i+4 staple scan starting at the N- and C-termini; (H) A triple i, i+4 staple scan that includes variable positioning of a third staple located at the middle of the peptide sequence and between the N- and C-terminal staples.

FIG. 9 demonstrates the enhancement of protease resistance by single- and double-stapling of the template exenatide peptide (SAH-Ex). Specifically, singly and doubly stapled SAH-Ex peptides are more resistant to chymotrypsin (pH 7) compared to the unmodified exenatide template peptide. In this example, the singly stapled peptides exhibit 2-3 fold enhancement in chymotrypsin resistance compared to the template peptide, whereas the doubly stapled peptide displays 8-fold enhancement compared to the template peptide and 2.7-4 fold enhancement compared to the corresponding singly stapled peptides.

FIG. 10 demonstrates that singly and doubly stapled SAH-Ex peptides are more resistant to pepsin (pH 2) compared to the unmodified exenatide template peptide. In this example, SAH-Ex(B) exhibits 6 fold enhancement in pepsin resistance compared to the template peptide, whereas the doubly stapled peptide displays 13 fold enhancement compared to the template peptide and 2-13 fold enhancement compared to the corresponding singly stapled peptides.

DETAILED DESCRIPTION

Figure 2A:
FIG. 2 (A) shows the structure of the GLP-1 receptor in complex with the alpha-helical region of exenatide (PDB ID 3C5T), and highlights those amino acids, including residues of the interacting face shown in ball and stick mode, which were determined by alanine scan to be especially important for functional activity (Runge, S. et al., 2008, J. Biol. Chem., 283: 11340-11347). An example of substitution sites for non-natural amino acid insertion on the non-interacting face of the core exenatide alpha-helix are also shown in space-fill mode to demonstrate the design of a doubly stapled exenatide peptide. The figure further provides the amino acid sequences of exendin-4 and residues 9-33 of exendin-4 shown with highlights of the above-mentioned critical amino acids as determined by alanine scan of the interacting face of exenatide (indicated in bold, underline and marked with a "a") and the amino acid residues marking the attachment points of the hydrocarbon staples (outlined with a box, underlined and marked with a "^"). (B) provides the amino acid sequence of GLP-1 (7-37) and indicates critical amino acid residues for functional activity (underlined). (Contillo et al. Proceedings of the 16$^{th}$ American Peptide Symposium Jun. 26-Jul. 1, 1999, Minneapolis, Minn., U.S.A.).

The instant invention relates to the unexpected finding that stably crosslinking a polypeptide having an insulinotropic activity, including incretin hormones (e.g., glucagon-like peptide-1), incretin analogs (e.g., liraglutide) or incretin mimetics (e.g., exenatide), provides superior and unexpected benefits in the treatment of conditions involving abnormal glucose homeostasis, e.g., type 2 diabetes and conditions relating to type 2 diabetes. Such benefits include, but are not limited to, extended half-life, enhanced alpha-helicity, improved thermal stability and protease resistance, increased functional activity and pharmacologic properties, improved bioavailability when administered by any route, and improved bioavailability and gastrointestinal absorption when delivered orally, as compared to uncrosslinked counterparts. Thus, the invention provides a new and advantageous approach to the administration of insulinotropic polypeptides that provides benefits not previously obtained or available. Accordingly, the present invention enables improved half-life (and thus, bioavailability, effectiveness, etc.) of insulinotropic polypeptides delivered by injection-based routes. Additionally, the instant invention makes it feasible to deliver effective amounts (i.e., which are bioavailable upon delivery) of insulinotropic polypeptide agents (e.g., GIP, GLP-1, GLP-2, exenatide, liraglutide, taspoglutide, or albiglutide) via non-injection-based routes, including oral, intranasal, and sublingual routes, thereby improving the chances of better patient compliance and ease of use.

Accordingly, the present invention is directed to compositions, kits and methods utilizing and/or making the structurally constrained insulinotropic polypeptides, including structurally constrained incretin hormones (e.g., glucagon-like peptide-1), incretin analogs (e.g., liraglutide) or incretin mimetics (e.g., exenatide) for use in treating and/or preventing conditions involving abnormal glucose homeostasis, e.g., type 2 diabetes and conditions relating to type 2 diabetes.

The invention is based, at least in part, on the results provided herein demonstrating that hydrocarbon-stapled, alpha-helical exenatide peptides and functional variants thereof display alpha-helical structural reinforcement, neutral and acid protease resistance, thermal stability, and enhanced pharmacologic properties, including oral absorption, remedying the classical shortcomings of lengthy peptide therapeutics. As a result, the peptides have superior pharmacologic properties in vivo compared to their unmodified counterparts, reducing the frequency and quantity of a structurally constrained peptide that needs to be administered as compared to an unmodified polypeptide sequence. In various embodiments, the polypeptides of the invention comprise one or more alpha helix domain(s) that are stabilized with at least one molecular tether, e.g., hydrocarbon staple, but may include two, three or more such hydrocarbon staples. The inclusion of multiple hydrocarbon staples is particularly suited for alpha helical peptides that are 20 or more amino acids in length. The inclusion of more than one (e.g., 2, 3, 4, 5, depending on the length of the peptide) hydrocarbon staples provides for exceptional structural, neutral and acid protease resistance, and thermal stability of the modified polypeptides, yielding bioactive peptides with strikingly enhanced pharmacologic properties in vivo.

As demonstrated herein, the stapled insulinotropic polypeptides of the invention (e.g., stapled exenatide) demonstrate stabilized alpha-helicity, proteolytic and thermal stability, and more desirable pharmacokinetic and bioavailability properties than a comparable non-structurally constrained polypeptides. Importantly, as further demonstrated herein, the stapled polypeptides of the invention can withstand protease action during oral delivery and gastrointestinal tract exposure, which is not possible for certain FDA-approved intravenous insulinotropic agents (e.g., exenatide or liraglutide).

DEFINITIONS

It is understood that this invention is not limited to the particular materials and methods described herein. It is also to be understood that the terminology used herein is for the purpose of describing particular aspects and is not intended to limit the scope of the present invention which will be limited only by the appended claims.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that such cited references are prior art.

As used herein, the singular forms "a", "an", and "the" include plural reference unless the context clearly dictates otherwise. For example, a reference to "a host cell" includes a plurality of such host cells known to those skilled in the art.

An "agent" is understood herein to include a therapeutically active compound or a potentially therapeutic active compound. An agent can be a previously known or unknown compound. As used herein, an agent is typically a non-cell based compound, however, an agent can include a biological therapeutic agent, e.g., polypeptide (e.g., insulinotropic polypeptide) or nucleic acid therapeutic, cytokine, antibody, etc. An agent can include the single or multiply stapled insulinotropic polypeptide (e.g., exenatide), and any functional homologs, fragments, analogs, derivatives or mimetics thereof.

As used herein, the term "functional fragment" refers to a polypeptide fragment of any insulinotropic polypeptide of the invention, including incretin hormones (e.g., glucagon-like peptide-1), incretin analogs (e.g., liraglutide) or incretin mimetics (e.g., exenatide), which retains at least about 10%, or greater than about 20% or 30%, or 40%, or 50%, or 60%, or 70%, or 80%, or 90%, or at least about 99% or more of the biologic or pharmacologic activity or properties of its corresponding native insulinotropic polypeptide, e.g., exenatide or GLP-1. The fragment can be of any contiguous region of amino acids of the polypeptide on which it is based. The fragment may also be in the form of a chimeric sequence of two or more different contiguous regions of amino acids of the polypeptide on which it is based which are joined together to form the fragment. In the context of the present invention, an example of a fragment of a naturally-occurring insulinotropic polypeptide (e.g., GLP-1) is residues 1-20 of GLP-1 (which can be denoted GLP-1$_{1-20}$ or by any similarly used nomenclature that would be apparent to the skilled artisan.

As used herein, the term "analog" or "analogue" refers to a compound X (e.g., a polypeptide, peptide or amino acid) which retains chemical structures of X necessary for functional activity of X yet which also contains certain chemical structures which differ from X. In the context of the present invention, an example of an analogue of a naturally-occurring insulinotropic polypeptide is a GLP-1 polypeptide which includes one or more non-naturally-occurring amino acids, e.g., those amino acid changes involved in the hydrocarbon staples of the invention. The analogs of the invention preferably retain at least about 10%, or greater than about 20% or 30%, or 40%, or 50%, or 60%, or 70%, or 80%, or 90%, or at least about 99% or more of the biologic or pharmacologic activity or properties of its corresponding native insulinotropic polypeptide, e.g., exenatide or GLP-1.

As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) Science 260:1937-1942), peptides in which all L-amino acids are substituted with the corresponding D-amino acids and "retro-inverso" peptides (see U.S. Pat. No. 4,522,752 by Sisto). Mimetics, in the context of the invention, may also include natural or synthetic polypeptides that bear little or no sequence homology and can be of very different overlength to a counterpart polypeptide against which it is compared, whereby the mimetic has at least about 10%, or greater than about 20% or 30%, or 40%, or 50%, or 60%, or 70%, or 80%, or 90%, or at least about 99% or more of the biologic or pharmacologic activity or properties of a counterpart polypeptide against which it is compared. For example, exenatide is a mimetic of GLP-1, having little overall sequence (53% identity) and an extended C-terminal region, but shares biological activity of GLP-1 at the GLP-1-receptor.

As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages).

As used herein, the term "functional exenatide variant," "exanatide-like peptide," "exanatide homologue," or "functional variant thereof" (of exenatide) is meant to refer to any peptide having a similar or homologous sequence to exenatide and having at least 50%, or 60%, or 70%, or 80%, or 90%, or 95%, or even 99% or more of the activity of the exenatide peptide of SEQ ID NO: 1, as measured by any suitable means for assaying exenatide activity.

As used herein, the term "insulinotropic polypeptide" or "insulinotropic agent" refers to a polypeptide or small molecule or other compound which have an insulinotropic activity. As used herein, a polypeptide having an "insulinotropic activity" is defined as one which stimulates or affects, either directly or indirectly, the production (e.g., expression, release, secretion, formation, etc.) and/or activity and/or amount of insulin. For example, an insulinotropic polypeptide can refer to one which causes, either directly or indirectly, a release of insulin from β-cells of the pancreas and/or causes, either directly or indirectly, an increase in the level of insulin in the plasma. Insulinotropic polypeptides can include any naturally occurring or synthetic polypeptide, and can further including any functional fragment, derivative, variant, homologue, or mimetic thereof. Insulinotropic polypeptides can include components of the incretin system (e.g., GLP-1, GIP) and any analogs, functional fragments, derivatives or mimetics thereof. The insulinotropic activity can be glucose-dependent or glucose-independent. The insulinotropic polypeptides of the invention may have additional or other activities as well and the term is not meant to be limiting in any manner as to other such activities. For example, an insulinotropic polypeptide of the invention, e.g., exenatide or GLP-1, can also block or minimize, either directly or indirectly, the production of glucagon. The term, "insulinotropic activity," is not meant to be tied to any specific mechanism of action. For example, DPP-IV is a regulatory degredative enzyme of the incretin system which functions as the normal degradative enzyme of GLP-1 and GIP. A mutant DPP-IV could be insulinotropic if its degradative activity is block or reduced such that the effective amount of GLP-1 and GIP—both which stimulate insulin production—is increased. Thus, such a mutant DPP-IV would be insulinotropic because it indirectly results in an increase in the amount of insulin.

It will be also appreciated that the insulinotropic agents or polypeptides (i.e., having an insulinotropic activity) can be regarded as agents or polypeptides having a "glucoregulatory" or "glycemic control" activity. Thus, the present invention also contemplates polypeptides having a glucoregulatory or glycemic control activity. As used herein, the term "glucoregulatory" or "glycemic control activity" refers to an activity that directly or indirectly is involved in, is responsive to or controls the metabolism of glucose in the body. Thus, the present invention is not limited to polypeptides having an insulinotropic activity, but instead may extend to any polypeptide that is glucoregulatory or has a glycemic control activity, which may include, for example, any polypeptide that affects, either directly or indirectly, the production (e.g., expression, release, secretion, formation, etc.) and/or activity and/or amount of glucose, insulin, or glucagon and the like.

As used herein "amelioration" or "treatment" is understood as meaning to lessen or decrease at least one sign, symptom, indication, or effect of a specific disease or condition, e.g., type 2 diabetes or related condition thereof. For example, amelioration or treatment of type-2 diabetes can be to stabilize blood glucose levels, Amelioration and treatment can require the administration of more than one dose of an agent, either alone or in conjunction with other therapeutic agents and interventions. Amelioration or treatment do not require that the disease or condition be cured.

As used herein, the term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and non-naturally occurring amino acids including beta-amino acids, prepared by organic synthesis or other metabolic routes and that can be applied for specialized uses such as increasing chemical diversity, functionality, binding capacity, structural mimesis, and stability.

As used herein, the term "amino acid side chain" or "amino acid R group" refers to a moiety attached to the α-carbon in an amino acid. For example, the amino acid side chain or R group for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid, a beta-amino acid).

As used herein, "carrier protein" for use with a structurally constrained peptide of the instant invention in a composition is understood as a protein or other substance such as a lipid that when conjugated to the constrained peptide elicit an enhanced insulin production. Examples of carrier conjugates are known in the art and could include for example a molecule which targets the singly or multiply stapled exenatide peptide or its homologues to the appropriate receptors.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody) or a substance produced by a reporter construct (e.g, β-galactosidase or luciferase). Depending on the method used for detection the amount and measurement of the change can vary. Changed as compared to a control reference sample can also include decreased binding of a ligand to a receptor, e.g., to a pancreatic GLP-1 receptor, in the presence of an antibody, antagonist, or other inhibitor. Determination of statistical significance is within the ability of those skilled in the art.

As used herein, the term "co-administration" as used herein is understood as administration of one or more agents to a subject such that the agents are present and active in the subject at the same time. Co-administration does not require a preparation of an admixture of the agents or simultaneous administration of the agents.

As used herein, the term "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Thus, a predicted nonessential amino acid residue in the exenatide polypeptide (SEQ ID NO: 1), for example, can be replaced with another amino acid residue from the same side chain family or homologues across families (e.g. asparagine for aspartic acid, glutamine for glutamic acid). Conservative changes can further include substitution of chemically homologous non-natural amino acids (i.e. a synthetic non-natural hydrophobic amino acid in place of leucine, a synthetic non-natural aromatic amino acid in place of tryptophan).

As used herein, the term "contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "detecting", "detection" and the like are understood that an assay performed for identification of a specific analyte in a sample, a product from a reporter construct in a sample, or an activity of an agent in a sample (e.g., binding inhibition, inhibition of syncytia formation, infectivity inhibition). Detection can include the determination of the level of a stapled peptide in the blood by ELISA kit or LC/MS analysis, the functional effect of the stapled peptide on a physiologic read-out such as serum glucose level, serum insulin level, or hemoglobin A1C percentage. The amount of analyte or activity detected in the sample can be within the range of detection for the particular assay, none, or below the level of detection of the assay or method.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition, e.g. type 2 diabetes.

The terms "effective amount," or "effective dose" or a "therapeutically effective amount or dose" refers to that amount of an agent to produce the intended pharmacological, therapeutic or preventive result. The pharmacologically effective amount results in the amelioration of one or more signs or symptoms of type 2 diabetes or related disorders. For example, a therapeutically effective amount preferably refers to the amount of a therapeutic agent that decreases blood glucose levels, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject. The evaluation of whether an amount is an effective amount can be done using any standardized testing known to those of ordinary skill in the art in the area of diabetes, including measuring changes in blood glucose levels, increasing levels of serum insulin, decreasing hemoglobin A1C percentage (i.e., the long term measure of glycemic status and diabetes control). More than one dose of an agent may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles). "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

Figures 2B, 3:
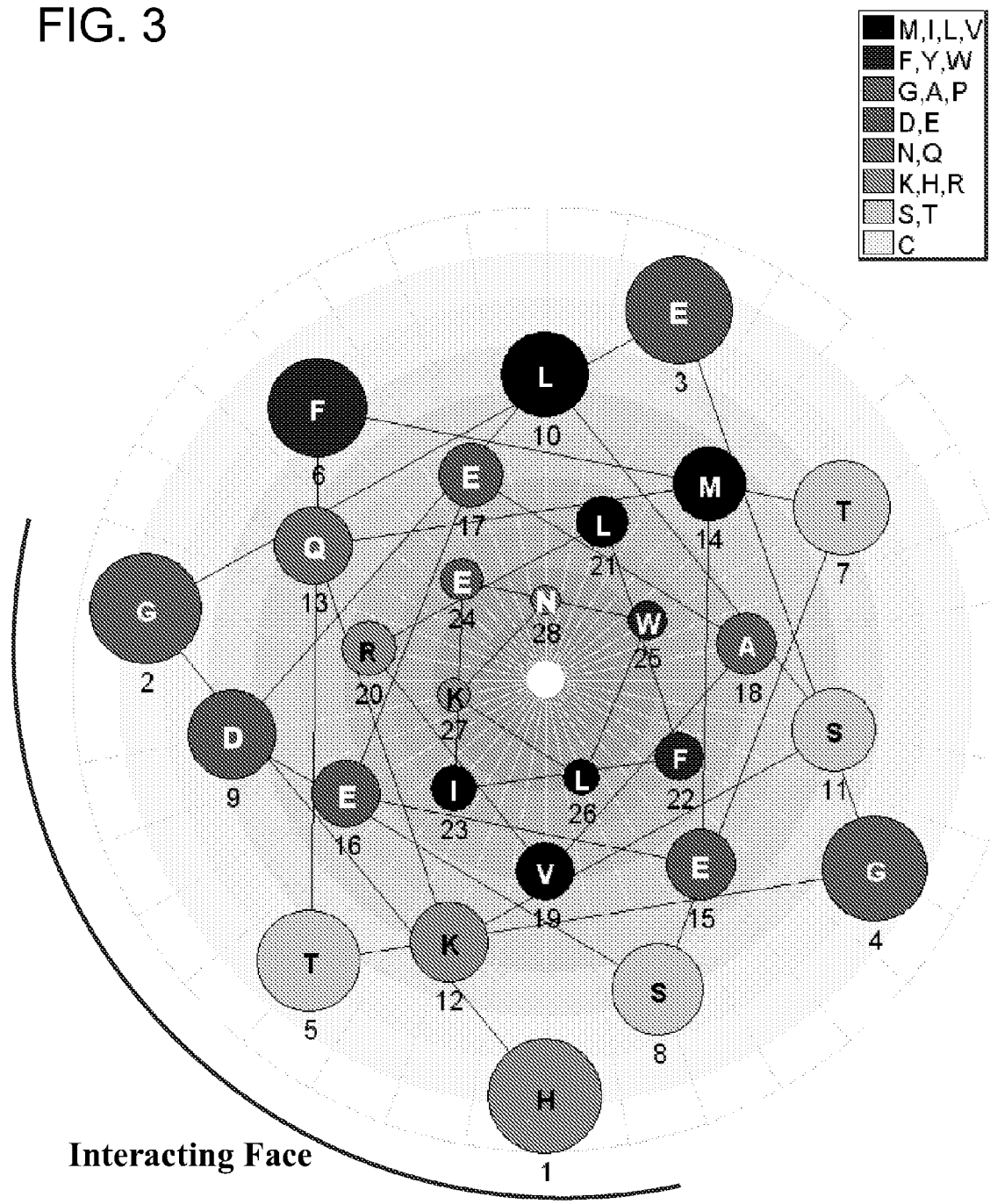
FIG. 3 shows a helical wheel depiction of the alpha-helical region of exenatide, highlighting the location of the face of the exenatide helix that interacts with the GLP-1 receptor. Substitution sites for staple insertion can be localized to the non-interacting face of the helix to enhance alpha-helical structure, receptor binding affinity, and functional activity. The particular residue positions of the non-interacting face side that may be involved in forming an attachment point of a hydrocarbon staple is not limited, and can include residues located at the N-terminus, C-terminus, or at any location between the ends of the polypeptide.
Figure 4A:
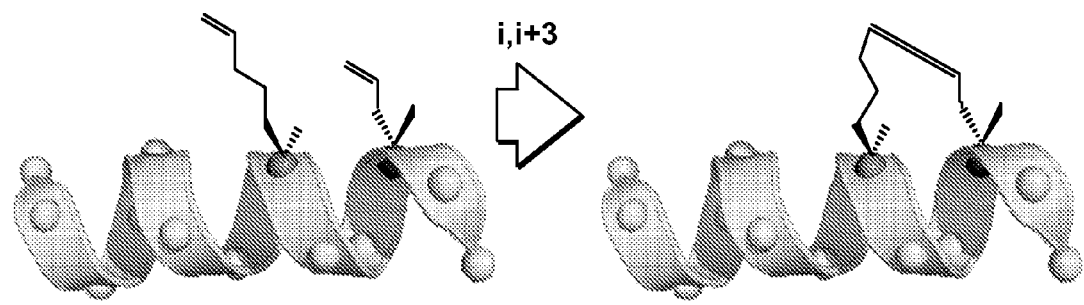
FIG. 4 shows how non-natural amino acids bearing hydrocarbon tethers (e.g., olefin tethers) can be inserted into the peptide sequence to generate singly stapled peptides. Staples can be located at (A) (i, i+3), (B) (i, i+4), and (C) (i, i+7) positions along the length of the peptide helix to generate a library of singly stapled peptides (i.e. "staple scan") to identify optimal positioning for the desired biophysical and biological properties. (D) Further illustrates staple scanning to identify the optimal staple position(s) for achieving the desired biophysical, biological, and pharmacologic properties of a polypeptide agent of interest (e.g., exenatide). Staple scanning involves the sequential evaluation of staple positions along the length of the peptide sequence template. An i, i+4 staple scan starting at the N-terminus is shown.
Figure 4B:
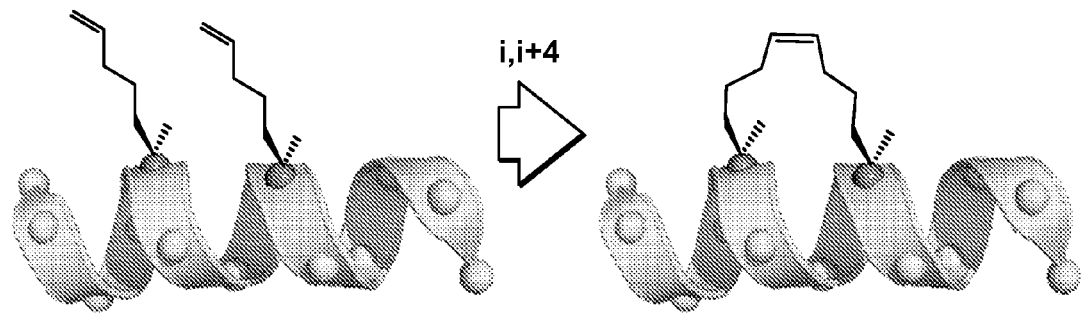
Figure 4C:
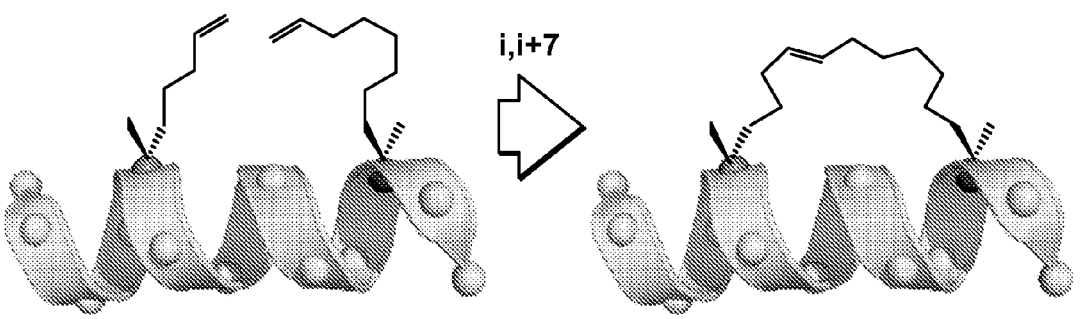
Figure 4D:
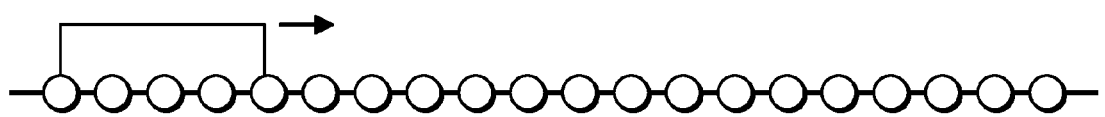

As use herein, the "face" of a helix, for example, an alpha-helix or a $3_{10}$ helix, is understood as the amino acids that are "stacked" in a helix of a protein so that when the helix is positioned vertically, the amino acids in a single face are depicted as being one on top of the other (see, e.g., FIG. 3). For example, an alpha-helix has about 3.6 amino acids per turn. Therefore, when a peptide having a sequence abcdefga'b'c'd'e'f'g' forms an alpha helix, the fourth and fifth amino acids (i+3 and i+4), i.e., amino acids d and e, will "stack" over the first amino acid (position 1+~3.6 amino acids), and the eighth amino acid, amino acid a' (i+7), will stack over amino acid a to form a face of the helix and starting a new turn with amino acid a' (see, e.g., FIG. 3). In an alpha-helix, amino acid b, the second amino acid, will "stack" with the fifth and sixth amino acids, i.e., amino acids e and f at the +3 and +4 positions, and with amino acid b' at the +7 position to form a face of the helix. Faces on helices starting with amino acid c, d, e, f, and g can be readily determined based on the above disclosure. Furthermore, a face of a helix can include two adjacent, three adjacent, or four adjacent columns of "stacked" residues.

An example of a "face" of a helix includes the "interacting face" of the helix (e.g., FIG. 3 shows the interacting face as that face of exenatide known to bind to the GLP-1-receptor). An "interacting face" amino acid residue is a residue that makes contact with the receptor, see e.g., FIGS. 2 and 3, when altered from the wild-type sequence of the polypeptide, results in abolishing or substantially abolishing the polypeptide functional activity. Substantially abolishing is understood as reducing the functional activity of an exenatide or functionally homologous peptide to less than about 50%, less than about 40%, less than about 30% of the wild-type peptide in an appropriate assay (e.g., receptor binding assay, functional assays that monitor second messenger signaling or changes in phosphorylation status of effectors downstream of receptor signaling, or assays that monitor glucose levels or glucose-stimulated insulin release in vitro or in vivo). The interacting face amino acid residues of the exenatide and exenatide-like peptides can readily be determined by methods well known in the art, such as structural determination and alanine scanning, as reported for the GLP-1 receptor and a subfragment of exenatide (amino acids 9-33) as pictured in FIG. 2. The term "interacting face" amino acid residue as used herein, includes conservative substitutions of the interacting face amino acids that do not disrupt function of the sequence. Generally, the "interacting face" amino acid residues are found at the interacting face of the alpha helix (as defined in FIGS. 2 and 3 for the core exenatide alpha-helix).

It will be apparent to those of ordinary skill in the art that some insulinotropic polypeptides (e.g., exenatide) or their functional homolog residues are less prone to substitution while others are more accepting of changes, as can be determined, for example, by "alanine or staple scanning," as described further herein. The insulinotropic polypeptides such as exenatide, GLP-1, and liraglutide, contain homologous sequences and alpha-helical domains that are readily identifiable by those possessing ordinary skill in the art by sequence based homology, structural homology and/or functional homology. Such methods are well known in the art and include bioinformatics programs based on pairwise residue correlations (e.g., ch.embnet.org/software/COILS_form.html), which have the ability to recognize coiled coils from protein sequences and model their structures (See Lupas, A., et al. Science 1991. 252(5009); p. 1162-1164).

As used herein, the term "hydrocarbon stapling", refers to a process for stably cross-linking a polypeptide having at least two modified amino acids that helps to conformationally bestow the native secondary structure of that polypeptide. Hydrocarbon stapling promotes or maintains a helical secondary structure in a peptide predisposed to have an helical secondary structure, e.g., alpha-helical secondary structure, to attain or maintain its native alpha-helical conformation. This secondary structure increases resistance of the polypeptide to proteolytic cleavage and heat, and also may increase hydrophobicity. Alternative nomenclature may be used to refer to "hydrocarbon stapling," including "hydrocarbon tethering or crosslinking," "molecular tethering," "intraresidue stapling, tethering, or crosslinking" "intrapeptidyl stapling, tethering, or crosslinking" and the like.

Hydrocarbon stapling promotes and maintains an alpha-helical secondary structure in peptides that thermodynamically favor an alpha-helical structure. As noted, this fortification of the polypeptide's secondary structure increases resistance of the polypeptide to proteolytic cleavage (e.g., by chymotrypsin or other proteases of the gastrointestinal tract) and heat, and also may increase the hydrophobicity of the polypeptide. Accordingly, the hydrocarbon stapled (and consequently, structurally constrained and fortified) polypeptides of the invention as described herein have improved biological activity relative to a corresponding non-hydrocarbon stapled (not structurally constrained) polypeptide, including extended half-life, enhanced alpha-helicity, improved thermal stability and protease resistance, increased functional activity and pharmacologic properties, and improved bioavailability when administered by any route.

Figure 5B:
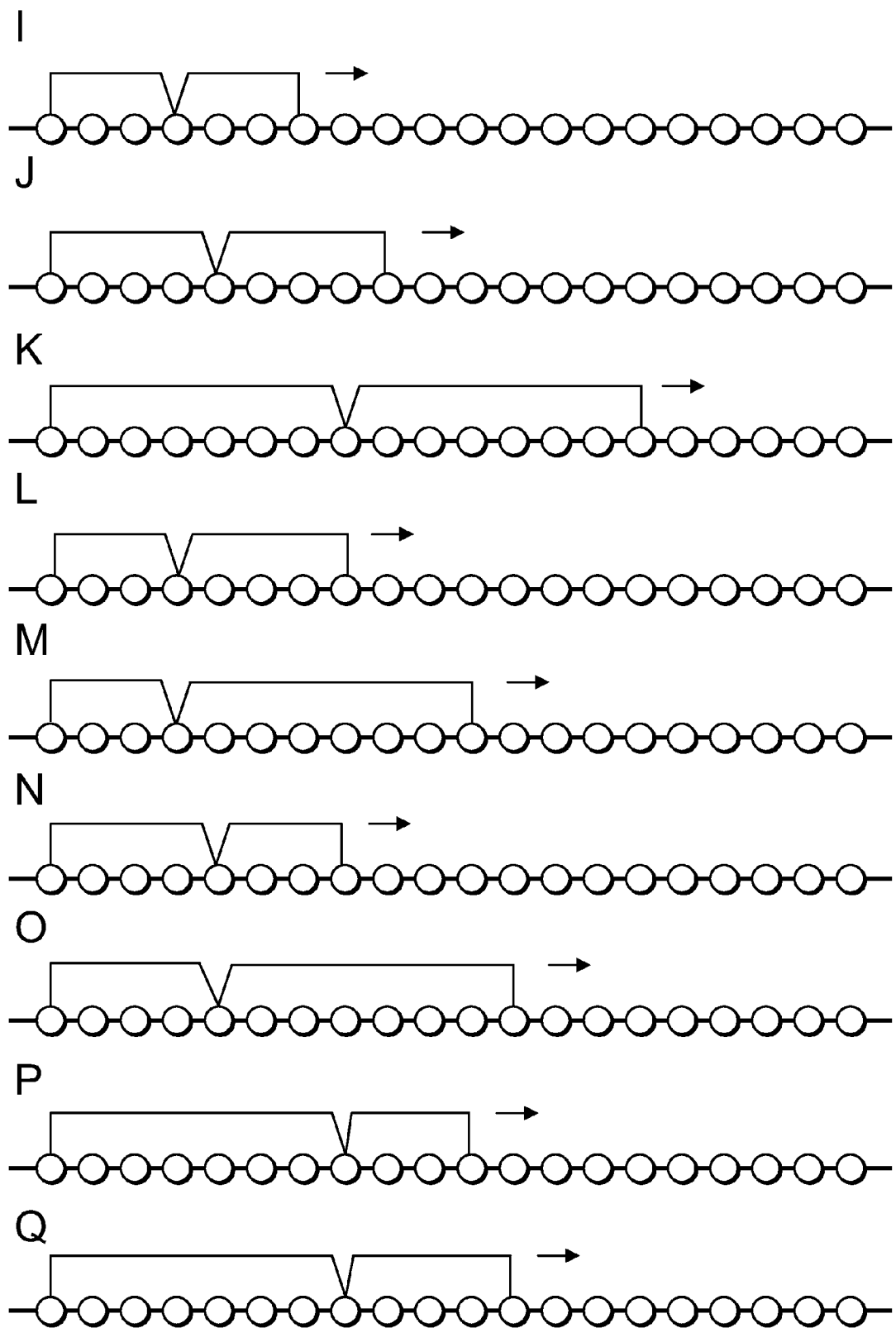
FIG. 5B shows further examples of structurally-stabilized insulinotropic peptides using sequentially installed staples such that the N- and C-terminal staples conjoin at a central non-natural amino acid bearing two olefinic side changes in the $\alpha$, $\alpha$ position. Configurations include sequential i, i+3 (I), i+4 (J), and i, i+7 staples (K), and combinations thereof, such as tandem i, i+3/i, i+4 (L), i, i+3/i, i+7 (M), i, i+4/i, i+3 (N), i, i+4/i, i+7 (O), i, i+7/i, i+3 (P), and i, i+7/i, i+4 (O) staples. As described above in FIG. 5A, the optimal staple positioning to achieve the desired biophysical, biological, and pharmacologic properties can be identified by staple scanning, which involves the sequential placement of discrete tandem staples (I-Q) along the length of the peptide sequence template, as represented by the arrows.

The hydrocarbon stapled polypeptides can include one or more tethers (linkages) between two non-natural amino acids, which tether(s) significantly enhances the helical secondary structure of the polypeptide. Generally, to promote a helical structure, the tether extends across the length of one or two helical turns (i.e., about 3-3.6 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , and the amino acid X is independently selected for each position, cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) is also contemplated. The use of multiple cross-links is effective at stabilizing and optimizing the peptide, especially with increasing peptide length, as is the case for some lengthy peptides such as insulinotropic exenatide and exantide-like peptides. Thus, the invention encompasses the incorporation of more than one crosslink within the polypeptide sequence. The use of multiple crosslinks is effective at stabilizing and optimizing the peptide, especially with increasing peptide length. The invention also encompasses the incorporation of one or more crosslinks within a polypeptide sequence, where the crosslinks are formed in a "stitched" configuration, i.e., wherein two sequentially-occurring staples (or crosslinks) arise from a common origin residue (e.g., as depicted in FIG. 5B).

As used herein, the term "staple scan" or "staple scanning" refers involves the sequential evaluation of staple positions along the length of the peptide sequence template. In one embodiment, staple scanning may be achieved by synthesis of a library of stapled peptides whereby the location of the i and i+3; i and i+4; and i and i+7 single and multiple staple stitches (which may be in a stitched configuration) are positioned sequentially down the length of the peptide sequence, and sampling all possible positions to identify desired or optimal properties and activities for the stapled or stitched constructs.

Methods for forming intramolecular tethers, e.g., hydrocarbon staple, can be found, for example, in U.S. Publication No. 2006/0014675A1, 200610008848A1, 2004/0171809A1 and U.S. Pat. Nos. 7,723,469, 7,192,713, and 7,084,244, each of which are incorporated herein by reference. Intramolecular tethers can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptide's is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at (www.ncbi.nih.gov/BLAST). The default parameters for comparing two sequences (e.g., "Blast"-ing two sequences against each other), by BLASTN (for nucleotide sequences) are reward for match=1, penalty for mismatch=-2, open gap=5, extension gap=2. When using BLASTP for protein sequences, the default parameters are reward for match=0, penalty for mismatch=0, open gap=11, and extension gap=1. Additional, computer programs for determining identity are known in the art.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

As used herein, "kits" are understood to contain at least one non-standard laboratory reagent for use in the methods of the invention. For example, a kit can include at least one of, preferably at least two of at least one peptide for modification, one or more aldehyde molecules for modification of peptides, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blisterpacks, or other suitable container forms known in the art. Such containers can be made of plastic, glass, laminated paper, metal foil, or other materials suitable for holding reagents.

A "non-essential" amino acid residue is a residue that can be altered from the wild-type sequence of a polypeptide without abolishing or substantially altering its functional activity and/or secondary structure (alpha-helical structure).

"Obtaining" is understood herein as manufacturing, purchasing, or otherwise coming into possession of.

As used herein, "operably linked" is understood as joined, preferably by a covalent linkage, e.g., joining an amino-terminus of one peptide to a carboxy terminus of another peptide, in a manner that the two or more components that are operably linked either retain their original activity, or gain an activity upon joining such that the activity of the operably linked portions can be assayed and have detectable activity using at least one of the methods provided in the examples.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, subcutaneous, buccal, sublingual, inhaled, intramuscular, intraperotineal, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

As used herein, the terms "peptide", "peptide compound" and "peptidic structure" are intended to include peptides comprised of naturally-occurring L-amino acids, as well as peptide derivatives, peptide analogues and peptide mimetics of the naturally-occurring L-amino acid structures. The terms "peptide analogue", "peptide derivative" and "peptidomimetic" as used herein are intended to include molecules which mimic the chemical structure of a peptide and retain the functional properties of the peptide (e.g., the ability to bind GLP-1-receptor). Approaches to designing peptide analogues, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) J. Mol. Recognition. 3:55;

Morgan, B. A. and Gainor, J. A. (1989) Ann. Rep. Med. Chem. 24:243; and Freidinger, R. M. (1989) Trends Pharmacol. Sci. 10:270.

A "polypeptide" as used herein is understood as two or more independently selected natural or non-natural amino acids joined by a covalent bond (e.g., a peptide bond). A polypeptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments). Examples of the polypeptides of the invention include the hydrophobic stapled insulinotropic polypeptides described herein, and any fragments, analogues, or mimetics thereof.

As used herein, "prevention" is understood as to limit, reduce the rate or degree of onset, or inhibit the development of at least one sign or symptom of a disease or condition. Prevention can require the administration of more than one dose of an agent or therapeutic.

A "sample" as used herein refers to a biological material that is isolated from its environment (e.g., blood or tissue from an animal, cells, or conditioned media from tissue culture) and is suspected of containing, or known to contain an analyte, such as a virus, an antibody, or a product from a reporter construct, or, as in this invention, measurable levels of the delivered stapled peptide or blood levels of a functional read-out analyte such as insulin and/or glucose. A sample can also be a partially purified fraction of a tissue or bodily fluid. A reference sample can be a "normal" sample, from a donor not having the disease or condition fluid, or from a normal tissue in a subject having the disease or condition (e.g., non-infected tissue vs. a infected tissue). A reference sample can also be from an untreated donor or cell culture not treated with an active agent (e.g., no treatment or administration of vehicle only). A reference sample can also be taken at a "zero time point" prior to contacting the cell or subject with the agent to be tested.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection.

The term "stable" or "stabilized", as used herein with reference to a polypeptide, refers to polypeptides which have been hydrocarbon-stapled to promote and/or maintain helical structure and/or improve protease resistance and/or improve acid stability and/or improve thermal stability and/or improve pharmacologic properties. Stabilized polypeptides are a type of structurally constrained polypeptides. Polypeptides may be singly, doubly, triply, or multiply stapled with the same or different hydrocarbon staple, in accordance with the methods described herein.

As used herein, "structurally constrained polypeptides" (or "structurally fortified") and the like are understood to include modified polypeptides having any (i.e., at least one) chemical modification, e.g., mutation of the original or native sequence with a natural or non-natural amino acid; chemical modification to incorporate a molecular tether; chemical modification to promote the formation of a disulfide bridge; etc. such that the structurally constrained peptide adopts a more limited number of structures than the unmodified peptide. A structurally constrained polypeptide can include 1, 2, 3, 4, 5, 6, 7, 8, 9, 10, 11, 12, or more mutations as compared to the native, wild-type sequence. For example, molecular tethers can include hydrocarbon staples to promote the formation of stable helical structures, especially alpha-helical and $3_{10}$ structures, or kinks depending on the positions of the ends of the tethers and the lengths of the tethers. Natural or non-natural amino acids can be employed to promote kinks (e.g. bends in the structure as defined by the variable angles between the two adjoining structures) or other preferred conformations. For example, the natural amino acid proline can induce a kink in a peptide due to the structure of the amino acid R group and the lack of a hydrogen-bond donor. Non-natural amino acids, particularly those having large and/or charged R groups, or N-methylated amides, N-substituted glycines, cyclic alpha,alpha-disubstitution, cyclic N,N-disubstitution, and beta-amino acids can promote specific, desired confirmations. It is understood that a population of "structurally constrained" peptides in solution may not all have the desired confirmation all of the time. Instead, in a population of structurally constrained peptides in solution, the desired confirmation is present at least about 30%, 40%, 50%, 60%, 70%, 80%, 90%, 100%, or more of the time than the native or original peptide sequence in solution prior to chemical modification. The structure of a population of peptides in solution can be determined by various methods known to those of skill in the art including, but not limited to, circular dichroism and NMR spectroscopy. Xray crystallography can be applied to determine the structure of a constrained peptide when packed in the form of a crystal.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

An agent, antibody, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to a non-specific compounds, or a pool of non-specific compounds. Specifically binds can be used in relation to binding one of two or more related compounds that have physically related structures. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient having an abnormal glucose homeostasis disorder, e.g., type 2 diabetes or at risk of developing type 2 diabetes.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as type 2 diabetes is within the ability of those in the art.

Subjects suffering from, and suspected of suffering from, a specific disease, condition, or syndrome are not necessarily two distinct groups.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents. In certain embodiments, orally-deliverable formulations can be prepared based on known methods, including those described in *Remington's Pharmaceutical Sciences* (Mack Pub. Co., Easton, Pa., 1985), among other known treatises on pharmaceutical formulations.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease, e.g., type 2 diabetes, may be an increase of about 10%, 20%, 50%, 100%, 150%, 200%, or more.

Should they appear, the following chemical entities are defined.

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive, i.e., 1, 2, 3, 4, 5, 6, 7, 8, 9, 10, 11, 12, 13, 14, 15, 16, 17, 18, 19, or 20) carbon atoms in it. The term "alkylene" refers to a divalent alkyl (i.e., —R—).

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

Ranges provided herein are understood to be shorthand for all of the values within the range. This includes all individual sequences when a range of SEQ ID NOs: is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. The symbol

" "

when used as part of a molecular structure refers to a single bond or a trans or cis double bond.

Any compositions or methods provided herein can be combined with one or more of any of the other compositions and methods provided herein.

Insulinotropic Polypeptides

Another aspect of the invention provides the insulinotropic polypeptides of the invention, which can be modified with 1, 2, 3, 4, 5, 6, 7, 8, 9, 10 or more hydrocarbon staples at any location(s) along the amino sequence of the inventive polypeptides in accordance with the methods outlined herein. The invention is not limited to any particular insulinotropic polypeptide, of a naturally occurring or synthetic source, and may including any known or yet-to-be identified polypeptide having insulinotropic properties, including exendin-4, exenatide, Gastric Inhibitory Polypeptide Preprotein (GIPP), Gastric Inhibitory Peptide (GIP), Glucagon-like Peptide-1 Precursor (GLP-1P), Glucagon-like Peptide-1 (GLP-1), Glucagon-like Peptide-2 (GLP-2), fragments of GLP-1, liraglutide, taspoglutide, albiglutide and LY2189265, all of which are exemplary insulinotropic polypeptides that can be used as templates in various embodiments of the invention for structural fortification by hydrocarbon stapling (see FIG. 1). The insulinotropic polypeptides can also include any homolog, analog, derivative, functional fragment or mimetic of any of those polypeptides indicated above.

The alpha helix of any of the insulinotropic polypeptides of the invention, e.g., exenatide, can be stabilized with at least one hydrocarbon staple using methods for hydrocarbon stapling described herein or in accordance with the teachings of the methods of U.S. Publication No. 2006/0014675A1, 2006/0008848A1, 2004/0171809A1 and U.S. Pat. Nos. 7,723,469, 7,192,713, and 7,084,244, each of which are incorporated herein by reference. In other embodiments, more than one, including at least 2, 3, or even 4 or even up to 12 or more hydrocarbon staples can be used to stabilize the exenatide of the invention. Hydrocarbon staples suitable for use with any of the modified polypeptides are described herein and in U.S. Publication No. 2005/0250680 or in U.S. Pat. No. 7,723,469 ("Stabilized alpha helical peptides and uses thereof"), each of which are incorporated by reference in their entireties. Hydrocarbon stapling allows a polypeptide, predisposed to have a helical secondary structure, to maintain its native helical conformation and increase its stability and efficacy. In one embodiment, the modified polypeptide has at least 10%, 20%, 30%, 35%, 40%, 45%, 50%, 60%, 70%, 80%, or 90% or more helicity in an aqueous solution as determined by circular dichroism. Assays for determining circular dichroism are known in the art and described herein.

In a particular embodiment, an insulinotropic polypeptide, e.g., exenatide, of the invention can include one hydrocarbon staple near the N-terminus. In another particular embodiment, an insulinotropic polypeptide, e.g., exenatide, of the invention can include one hydrocarbon staple near the C-terminus. In another particular embodiment, the exenatide of the invention can include a hydrocarbon staple in the middle of the sequence and at any position between the N- and C-terminii. In yet another embodiment, the exenatide of the invention can include one hydrocarbon staple near the C-terminus and another hydrocarbon staple near the N-terminus. In yet another embodiment, the exenatide of the invention can include one hydrocarbon staple near the C-terminus and another hydrocarbon staple in the middle of the sequence, or one hydrocarbon stapled near the N-terminus and another in the middle of the peptide sequence.

In yet another embodiment, the insulinotropic polypeptides of the invention may be sequentially truncated from either the N-terminus or the C-terminus, or in an alternating fashion from the N- and C-terminii with hydrocarbon staples being inserted into the foreshortened variants.

Figure 7B:
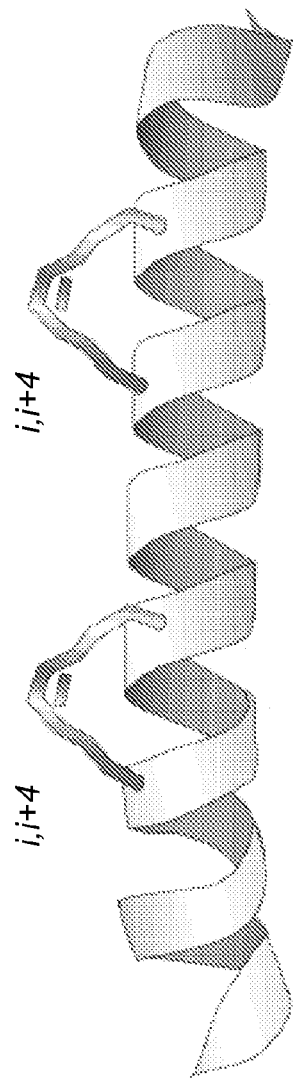
FIG. 7 (A) Compositions of Stabilized Alpha-Helices ("SAH") of Exenatide (SAH-Ex) and GLP-1 (SAH-GLP1). A mutant construct of exenatide (Met14NorLeu) was used as the template for the construction of singly and doubly stapled SAH-Ex peptides. (B) Exemplary singly and doubly stapled SAH-Ex peptides employed in biophysical, biological, and pharmacologic studies. X, crosslinking non-natural amino acid; B, norleucine.
Figure 8A:
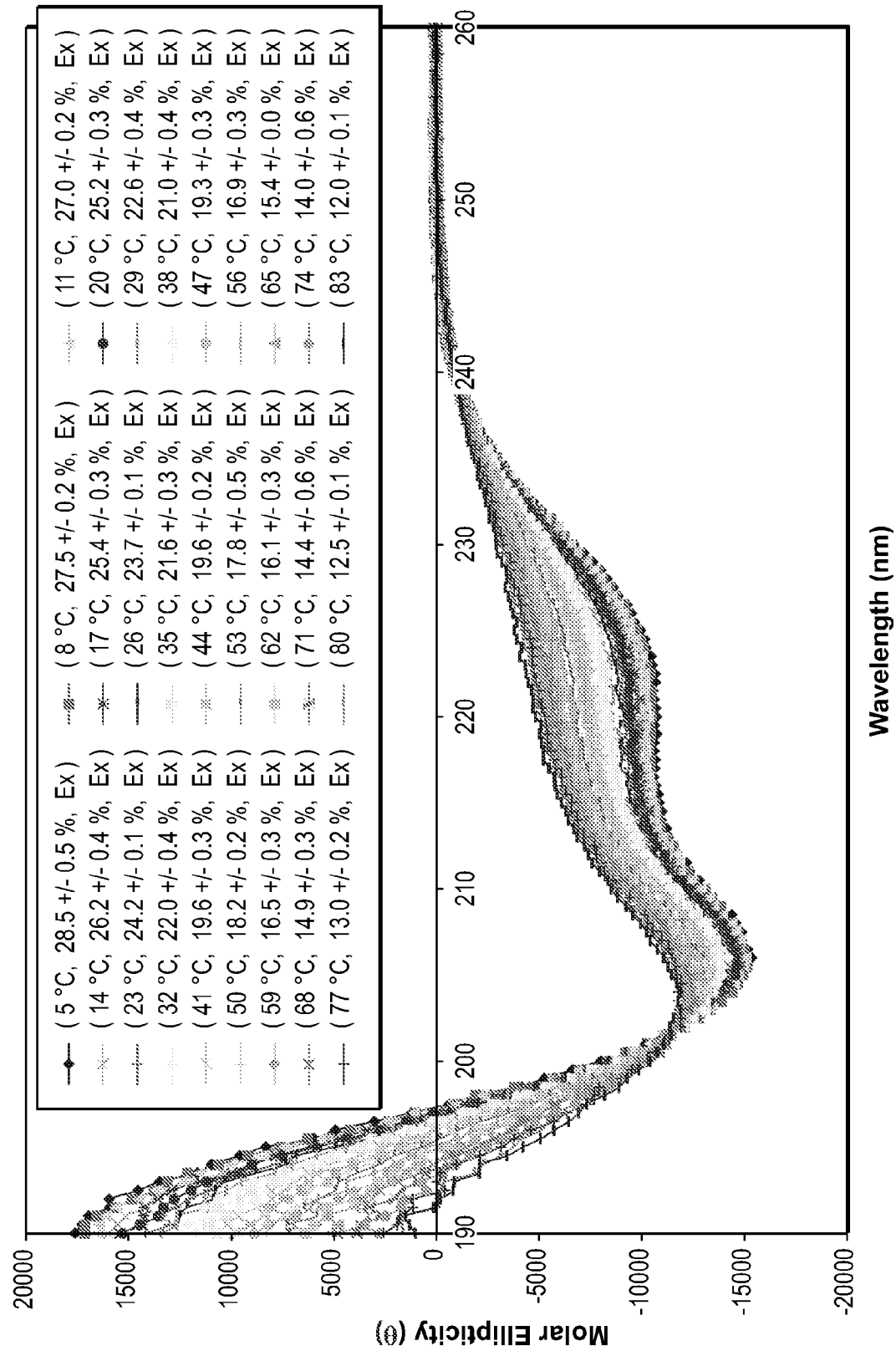
FIG. 8 provides a circular dichroism spectra of the template (A) and SAH-Ex (B-D) polypeptides across a broad temperature range, demonstrating the enhanced alpha-helicity of singly and doubly stapled SAH-Ex peptides. (E) Provides temperature melt curves for the template and SAH-Ex peptides demonstrating the enhanced thermal stability of singly and doubly stapled SAH-Ex peptides. Specifically, (A)-(D) shows the circular dichroism spectra of Ex(Met14NorLeu), SAH-Ex(A), SAH-Ex(B), and SAH-Ex(A,B), highlighting the increased alpha-helicity of the singly and doubly stapled peptides across a broad temperature range (5° C.-83° C.). (E) shows a circular dichroism temperature melt plot for Ex(Met14NorLeu), SAH-Ex(A), SAH-Ex(B), and SAH-Ex (A,B), demonstrating the enhanced thermal stability of the singly and doubly stapled peptides compared to the corresponding unstapled template peptide.
Figure 8B:
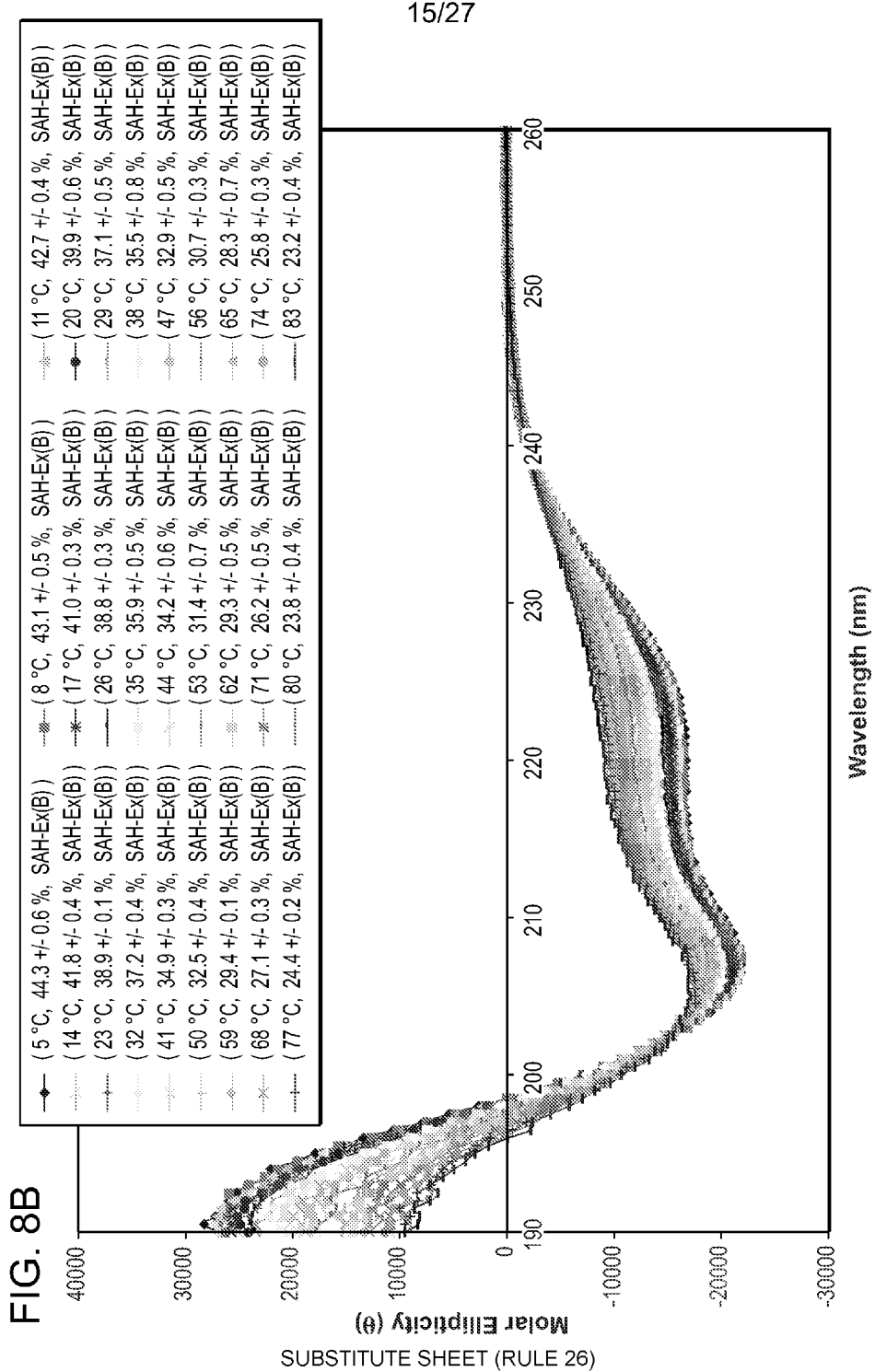
Figure 8C:
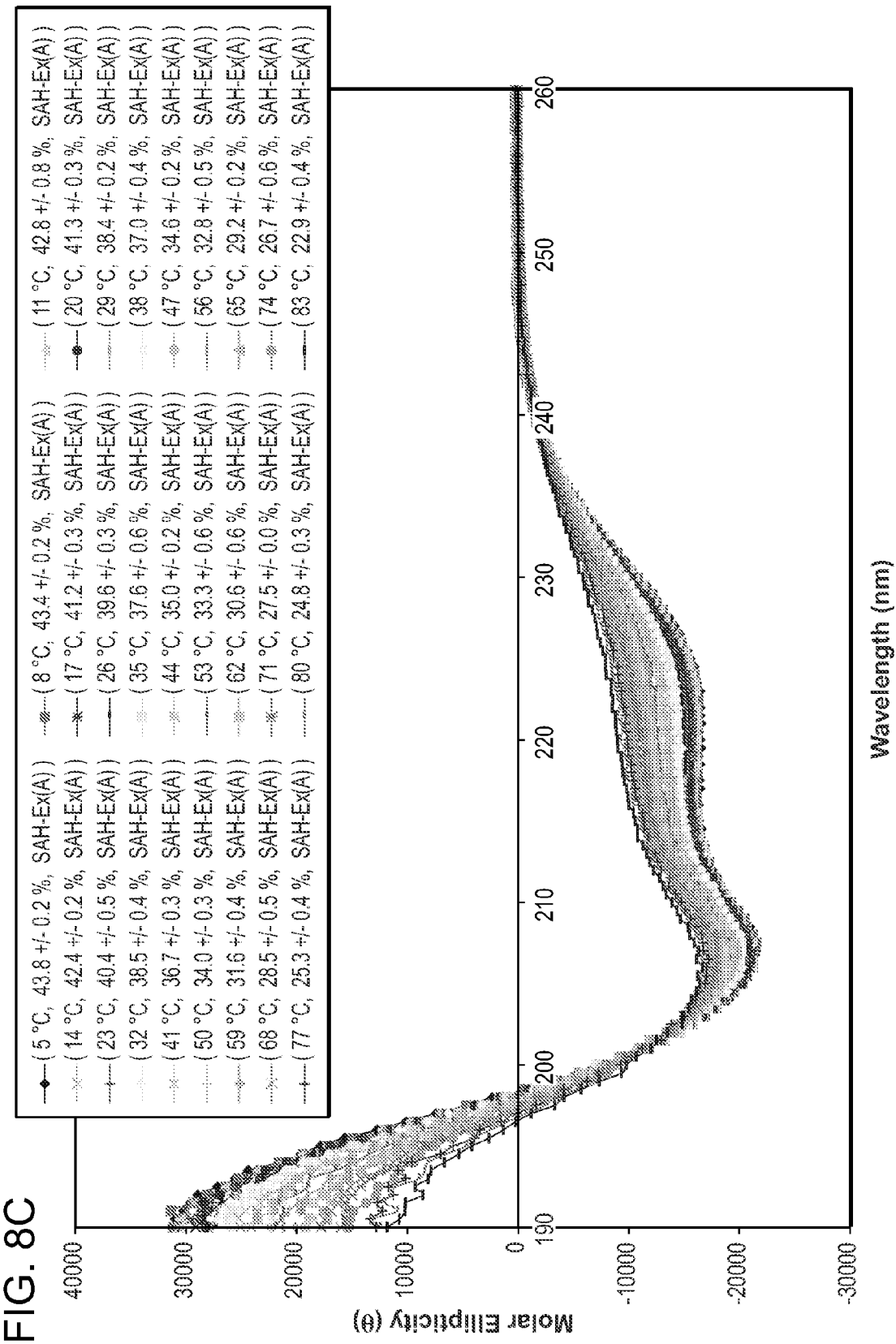
Figure 8D:
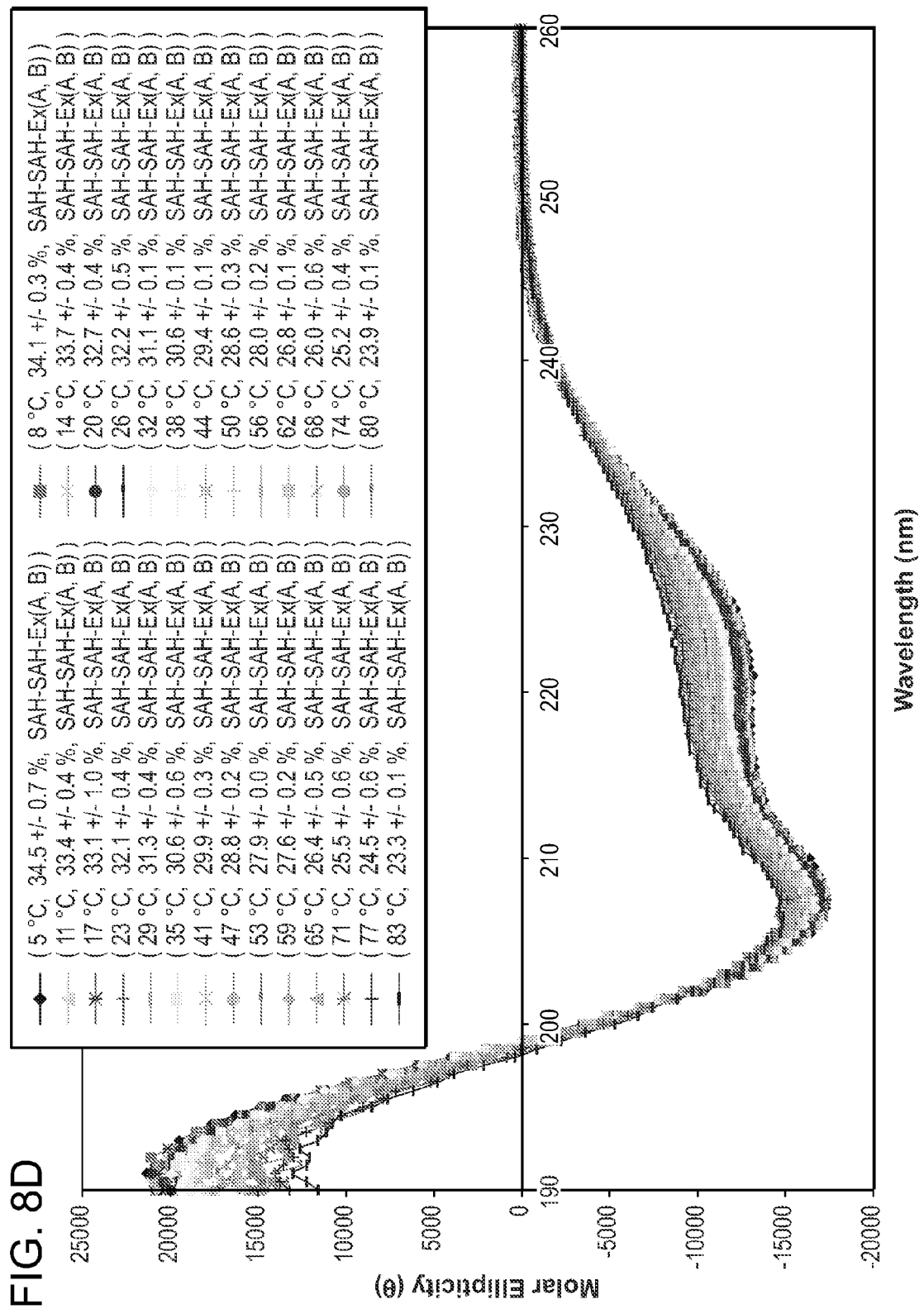
Figure 8E:
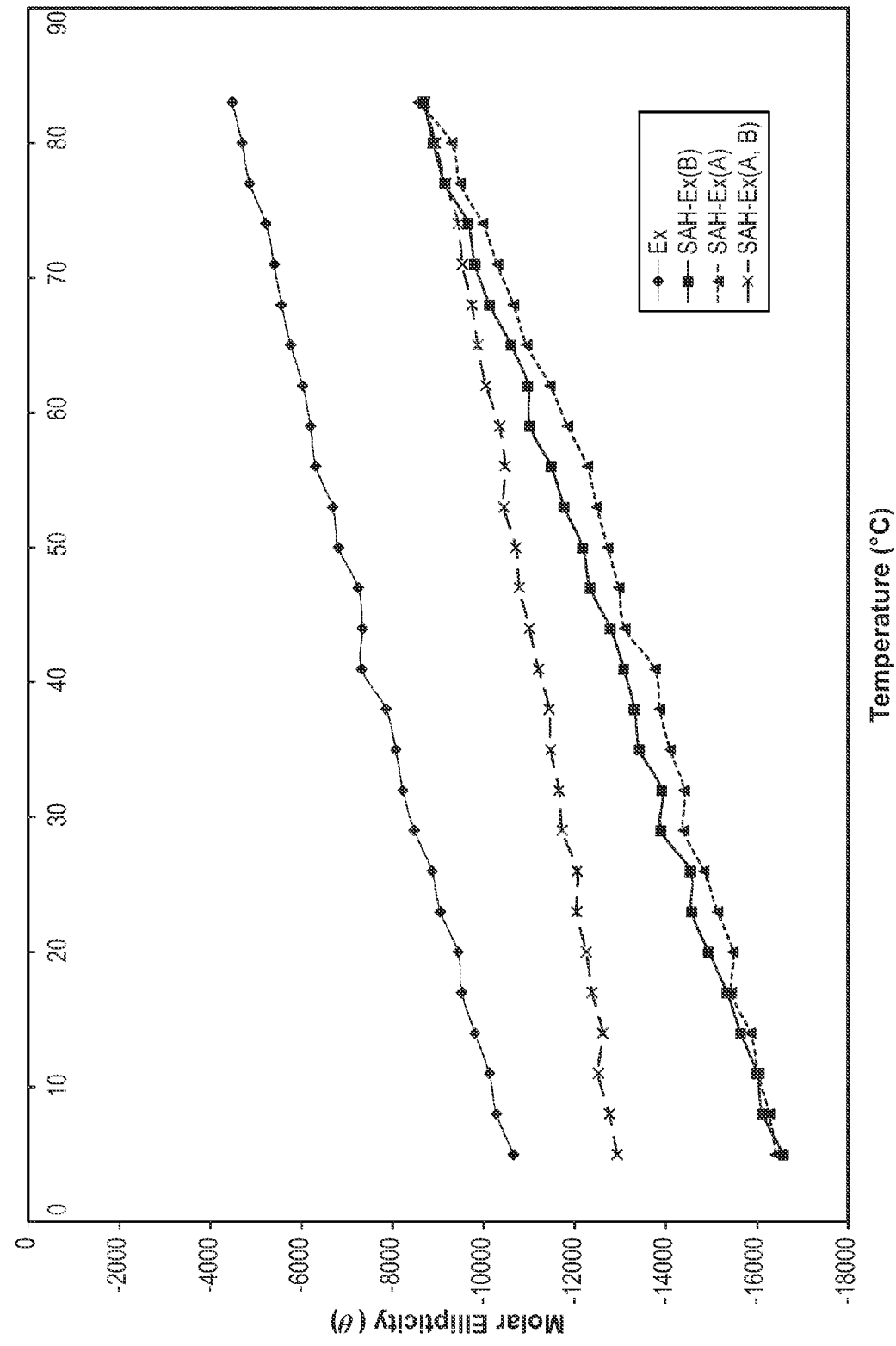

Exemplary stapled polypeptides of the invention are shown in FIG. 7.

The hydrocarbon stapled polypeptides include a tether (linkage) between two amino acids, which tether significantly enhances the helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, any of the amino acid residues of the modified polypeptides of the invention may be tethered (e.g., cross-linked) in conformity with the above. Suitable tethers are described herein and in U.S. Patent Publication No. 2005/0250680 and U.S. Pat. No. 7,723,469 (both of which are incorporated herein by reference). It is understood that tethers such as hydrocarbon staples can be positioned at other intervals to promote helical variants (e.g. with different pitches, angles, or residues and fractions thereof per turn) or structures other than helices.

In a further embodiment, the hydrocarbon staple(s) is positioned so as to link a first amino acid (i) and a second amino acid (i+3) which is 3 amino acids downstream of the first amino acid. In another embodiment, the hydrocarbon staple links a first amino acid (i) and a second amino acid (i+4) which is 4 amino acids downstream of the first amino acid. In yet another embodiment, the hydrocarbon staple links a first amino acid (i) and a second amino acid (i+7) which is 7 amino acids downstream of the first amino acid.

Mutations, Truncations, and Extensions of Insulinotropic Polypeptides

The invention contemplates insulinotropic peptides (e.g., exenatide) having conserved and non-conserved amino acid substitutions. Conserved amino acid substitutions consist of replacing one or more amino acids with amino acids of similar charge, size, and/or hydrophobicity characteristics, such as, for example, a glutamic acid (E) to aspartic acid (D), aspartic acid (D) to asparagine (N), and glutamic acid (E) to glutamine (Q) amino acid substitution. Non-conserved substitutions consist of replacing one or more amino acids with amino acids possessing dissimilar charge, size, and/or hydrophobicity characteristics, such as, for example, a glutamic acid (E) to valine (V) substitution. Substitutions can include the use of conserved or non-conserved non-natural amino acids.

Amino acid insertions may consist of single amino acid residues or stretches of residues. The insertions may be made at the carboxy or amino terminal end of the full-length or truncated exenatide peptides, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into full-length or truncated insulinotropic polypeptides (e.g., exenatide), as long as such insertions result in modified peptides which may still exhibit at least about 50%, or 60%, or 70%, or 80%, or 90%, or 95%, or 99% or higher the activity of a comparable starting polypeptide (e.g., modified exenatide of SEQ ID NO: 1). Such changes preferably also result in exenatide variants that remain orally bioavailable and/or retain prolonged stability in the blood and tissues.

Deletions of full-length or truncated exenatide peptides are also within the scope of the invention. Such deletions consist of the removal of one or more amino acids from the exenatide peptides; or exenatide variants, with the lower limit length of the resulting peptide sequence being 4, 5, or 6 amino acids. Such deletions may involve a single contiguous or greater than one discrete portion of the peptide sequences. One or more such deletions may be introduced into full-length or truncated insulinotropic peptides (e.g., exenatide), as long as such deletions result in peptides which may still exhibit at least about 50%, or 60%, or 70%, or 80%, or 90%, or 95%, or 99% or higher the activity of a comparable starting polypeptide (e.g., modified exenatide of SEQ ID NO: 1). and which are preferably orally bioavailable and/or retain prolonged stability in the blood and tissues.

Stabilization of Insulinotropic Polypeptides (e.g., Exenatide)

The modified insulinotropic polypeptides (e.g., exenatide) of the present invention are structurally constrained (e.g., stabilized, stapled) helical and/or include one or more amino acid sequence modifications as compared to the native (i.e., wild type or otherwise naturally occurring) sequence to incorporate natural and/or non-natural amino acids to limit the structural flexibility of the peptide as compared to the native sequence, which can lose bioactive shape when taken out of physiologic context. Preferably, the insulinotropic polypeptides of the invention include at least one molecular tether such as a hydrocarbon staple. Hydrocarbon stapling is described in U.S. Patent Publication No. 2005/0250680 or U.S. Pat. No. 7,723,469, which are incorporated herein by reference in their entirety, as well as Walensky et al. Science, 2004, 305: 1466-70; Walensky et al. Mol. Cell. 2006, Oct. 20; 24(2):199-210; Bernal et al. J Am Chem. Soc. 2007 Apr. 25; 129(16):5298; Danial et al Nat Med 2008, 2008 February; 14(2):144-53. Epub 2008 Jan. 27; Gavathiotis et al Nature 2008, Oct. 23; 455(7216):1047-9; Stewart et al. Nature Chem Bio 2010 Jun. 20 (electronically), as well as in U.S. Publication No. 2006/0014675A1, 2006/0008848A1, 2004/0171809A1 and U.S. Pat. Nos. 7,192,713, and 7,084,244, each of which are incorporated herein by reference, all of which are incorporated herein by reference.

The peptide α-helix participates in critically important protein interactions by presenting specific amino acid residues in an ordered and precise arrangement over a relatively large contact surface area (Chittenden, T., et al., *Embo Journal*, 1995. 14(22): p. 5589-5596; Kussie, P. H., et al. *Science*, 1996. 274(5289): p. 948-953; Ellenberger, T. E., et al., *Cell*, 1992. 71(7): p. 1223-1237). Alpha-helical domains and other protein structural features are frequently stabilized by scaffold sequences in the remainder of the protein, which facilitate the formation and/or maintenance of a helical structure, e.g., an α-helical structure. When taken out of context, α-helical peptide motifs can unfold, leading to loss of biological activity. Critical challenges is developing α-helical peptides include promoting and/or maintaining their natural α-helical structure and preparing peptides that can resist proteolytic, acid and thermal degradation, and thereby remain intact in vivo.

For example a structurally constrained peptide of the invention can include an alpha-helical domain of an exenatide polypeptide. In some instances, the structurally constrained peptide is constrained with a hydrocarbon tether at the N-terminus. In some instances, the structurally constrained peptide is constrained with a hydrocarbon tether at the C-terminus. In other instances, the structurally constrained peptide is constrained with a hydrocarbon tether within the middle of the peptide sequence. In still further instances, the structurally constrained peptide is constrained with more than one hydrocarbon tether, e.g., wherein at least one or both of the tethers is at or near a terminus of the peptide (i.e., beginning at 1, 2, 3, 4, 5, 6, 7, 8, 9, 10, 11, 12, 13, 14, or 15 residues from the N- or C-terminus of the peptide). In a particular embodiment, the exenatide peptide comprises a tether at or near both the N- and C-terminii (i.e., beginning at 1, 2, 3, 4, 5, 6, 7, 8, 9, 10, 11, 12, 13, 14, or 15 residues from the N- or C-terminus of the peptide). These particular positions for hydrocarbon stapling are not meant to be limiting in any way as placement of the hydrocarbon staple (multiple staples) can be at any location (or combination of locations) along the length of a given insulinotropic polypeptide. Such positions can be determined and optimized empirically and without undue experimentation utilizing the staple scanning methods described and shown in the figures of this specification.

The hydrocarbon stapled polypeptides include a tether (linkage) between two amino acids, which tether significantly enhances the helical secondary structure of the polypeptide. Generally, the tether extends across the length of one or two helical turns (i.e., about 3-3.6 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) has also been achieved, compounding the benefits of individual stapled adducts (e.g. improved helicity and activity; improved helicity and thermal stability; improved helicity and acid stability; improved helicity and pharmacologic properties). Thus, the invention encompasses the incorporation of more than one crosslink within the polypeptide sequence to either further stabilize the sequence or facilitate the structural stabilization, proteolytic resistance, thermal stability, acid stability, pharmacologic properties, and biological activity enhancement of longer polypeptide stretches. The invention also contemplates that a pair of sequentially-occurring staples or tethers may be formed in a "stitched" configuration, i.e., wherein the end of a first-occurring tether originates from the same residue as the beginning of a second sequentially-occurring staple, e.g., as exemplified in FIG. 5B.

In some embodiments of the invention, the tethers, e.g., hydrocarbon staples are used to stabilize structures other than helices. In such cases, the ends of the tethers can be placed at intervals other than at i, i+3, i+4, and i+7. For example, a molecular tether can be used to stabilize the kink region of a peptide domain to produce a curved surface rather than a flat continuous face as with a helix. The amino acid sequence and the placement of the ends of the tether will determine the number of amino acids spanned by the tether. Such considerations are well understood by those of skill in the art.

In one embodiment, the modified polypeptides of the invention have the formula (I),

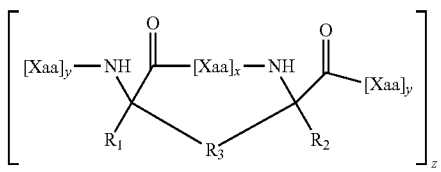

wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

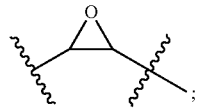 [SMILES: *C1OC1*]

$R_6$ is H, alkyl, or a therapeutic agent;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid. The modified polypeptides may includes an amino acid sequence which forms an alpha-helix and is 30% or more identical to, or contain at least 7 contiguous amino acids from an amino acid sequence of SEQ ID NO:1-4, wherein X is any amino acid and further identifies the amino acid residues which are linked by a hydrocarbon staple, and B is methionine or norleucine.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl).

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C'_{11}$ alkenyl.

In some instances, $R_3$ is a straight chain alkyl, alkenyl, or alkynyl.

In some instances $R_3$ is —$CH_2$—$CH_2$—$CH_2$—CH=CH—$CH_2$—$CH_2$—$CH_2$—.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

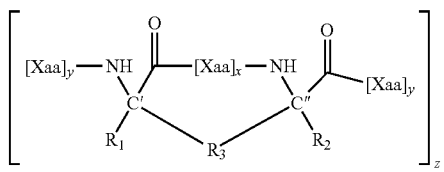

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4—K—R_4]_n$; and $R_4$ is a straight chain alkyl, alkenyl, or alkynyl.

In some embodiments the modified polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more contiguous amino acids of an insulinotropic polypeptide. Each $[Xaa]_y$ is a peptide that can independently comprise at least 5, 6, 7, 8, 9, 10, 11, 12, 13, 14, 15, 16, 17, 18, 19, 20, 25 or more contiguous amino acids of a insulinotropic polypeptide, e.g., the sequences of FIG. 1.

The modified polypeptide can comprise 3, 4, 5, 6, 7, 8, 9, 10, 11, 12, 13, 14, 15, 16, 17, 18, 19, 20, 25, 30, 35, 40, 45, 50 contiguous amino acids of an insulinotropic polypeptide, e.g., the sequences of FIG. 1, wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as

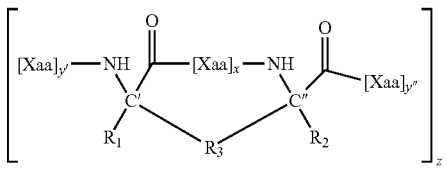

$[Xaa]_y'$, and $[Xaa]_y''$ can each comprise contiguous polypeptide sequences from the same or different heptad repeat or heptad repeat like domains.

The invention features cross-linked polypeptides comprising 10 (11, 12, 13, 14, 15, 16, 17, 18, 19, 20, 21, 22, 23, 24, 25, 30, 35, 40, 45, 50 or more) contiguous amino acids of an insulinotropic polypeptide, e.g., the sequences of FIG. 1, wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another embodiment, the modified polypeptides of the invention have the formula (II),

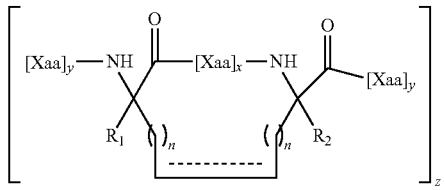

wherein
each $R_1$ and $R_2$ are independently H, alkyl, alkenyl, alkynyl, arylalkyl, cycloalkylalkyl; heteroarylalkyl; or heterocyclylalkyl;
each n is independently an integer from 1-15;
x is 2, 3, or 6
each y is independently an integer from 0-100;
z is an integer from 1-10 (e.g., 1, 2, 3, 4, 5, 6, 7, 8, 9, 10);
each Xaa is independently an amino acid.

The modified polypeptide forms an alpha-helix and can have an amino acid sequence which forms an alpha-helix and is 30% or more identical to, or contain at least 7 contiguous amino acids from an amino acid sequence of SEQ ID NOs: 2, 15-38 (exenatide) and 39-62 (GLP1(7-37)) wherein X is any amino acid and further identifies the amino acid residues which are linked by a hydrocarbon staple, and B is methionine or norleucine. The modified polypeptides may include an amino acid sequence that forms an alpha-helix and is 30% or more identical to, or contain at least 3, preferably at least 7 contiguous amino acids from an amino acid sequence, or at least two amino acids from a face of a helix formed by a peptide having the sequence of SEQ ID NOs: 2, 15-38 (exenatide) and 39-62 (GLP1(7-37)) wherein X is any amino acid and further identifies the amino acid residues which are linked by a hydrocarbon staple, and B is methionine or norleucine.

In still another embodiment, the modified polypeptides of the invention have the formula (III),

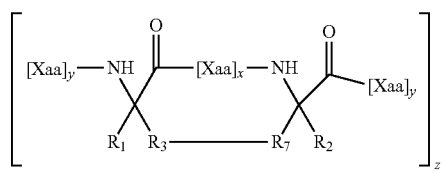

wherein;
each $R_1$ and $R_2$ are independently H, alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$ or a naturally occurring amino acid side chain; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K is O, S, SO, $SO_2$, CO, $CO_2$, $CONR_6$, or

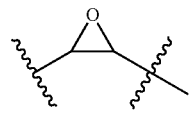 [SMILES: *C1OC1*]

$R_6$ is H, alkyl, or a therapeutic agent;
$R_7$ is alkyl, alkenyl, alkynyl; $[R_4—K—R_4]_n$ or an naturally occurring amino acid side chain; each of which is substituted with 0-6 $R_5$;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid.

The modified polypeptides may include an amino acid sequence that forms an alpha-helix and is 30% or more identical to, or contain at least 7 contiguous amino acids from an amino acid sequence, or at least two amino acids from a face of a helix formed by a peptide having the sequence of SEQ ID NOs: 2, 15-38 (exenatide) and 39-62 (GLP1(7-37)), wherein X is any amino acid and further identifies the amino acid residues which are linked by a hydrocarbon staple, and B is methionine or norleucine.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary structure, whereas, in some instances, it is desirable to provide less constraint on the secondary structure, and thus a longer tether may be desired. It is further understood that the insertion of a tether at a site or in an amino acid sequence when the amino acid sequence has no tendency to form a helix will not result in helix formation.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids to promote and/or maintain the structures other than alpha helices.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The specific method of synthesis of the peptides is not a limitation of the invention.

Synthesis of the Polypeptides of the Invention

The peptides of this invention can be made by chemical synthesis methods, which are well known to the skilled artisan and described herein. See, for example, Fields et al., Chapter 3 in *Synthetic Peptides: A User's Guide*, ed. Grant, W. H. Freeman & Co., New York, N.Y., 1992, p. 77. Hence, peptides can be synthesized using the automated Merrifield techniques of solid phase synthesis with the alpha-$NH_2$ protected by either t-Boc or F-moc chemistry using side chain protected amino acids on, for example, an Applied Biosystems Peptide Synthesizer Model 430A or 431 or the AAPPTEC multichannel synthesizer APEX 396.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides can also be made by conjoining individual synthetic peptides using native chemical ligation. Alternatively, longer synthetic peptides can be synthesized by well known recombinant DNA techniques. Such techniques are provided in well-known standard manuals with detailed protocols. To construct a coding sequence encoding a peptide of this invention, the amino acid sequence is reverse translated to obtain a nucleic acid sequence encoding the amino acid sequence, preferably with codons that are optimum for the organism in which the gene is to be expressed. Next, a coding sequence is made, typically by synthesizing oligonucleotides which encode the peptide and any regulatory elements, if necessary. The coding sequence is inserted in a suitable cloning vector and transfected into a host cell. Furthermore, the host cell is engineered so as to be able to incorporate the non-natural amino acids for the hydrocarbon staple. The peptide is then expressed under suitable conditions appropriate for the selected expression system and host. See Liu et al. *Proc. Nat. Acad. Sci.* (USA), 94:10092-10097 (1997). The peptide is purified and characterized by standard methods.

The peptides can be made in a high-throughput, combinatorial fashion, e.g., using a high-throughput polychannel combinatorial synthesizer such as that available from Advanced Chemtech/APPTTEC.

Assaying Activity of the Insulinotropic Polypeptides of the Invention

Described herein, are methods for evaluating the ability of a structurally constrained insulinotropic polypeptide of the invention (e.g., exenatide) to enhance the production of insulin, either in vitro, in vivo, or preferably both. Specifically, such assays are described below and in the Examples. Additional assays for evaluating the insulin-enhancing activity of exenatide are well known to those with ordinary skill in the art. In addition, described herein, are methods for evaluating other aspects and properties of the insulinotropic polypeptides of the invention (e.g., exenatide), including their improved bioavailability when delivered orally, and other benefits of the polypeptides of the invention, including, but are not limited to, their extended half-life, their enhanced alpha-helicity, their improved thermal stability and their protease resistance, and their increased functional activity and pharmacologic properties, improved bioavailability when administered by any route. Many of these properties are described and demonstrated in the Examples; however, it is noted that one or ordinary skill in the art will be able to ascertain without undue experimentation the improved properties imparted on the insulinotropic polypeptides of the invention using known methods and assays. For example, assays can include protease resistance assays, plasma stability assays, pharmacokinetics assays, GLP-1-receptor binding assays, GLP-1-receptor second messenger signaling assays, glucose-stimulated insulin release cellular assays, in vivo monitoring of serum glucose and insulin levels in response to insulinotropic peptide treatment, and general ELISA or antibody-based methods for measuring quantities of insulin, glucagon or other glucoregulatory component in the blood, all of which will be understood in the context of the herein Examples, as well as based on the knowledge possessed by one of ordinary skill in the art. All of such assays and measurements can be performed without undue experimentation.

In a particular example, insulinotropic activity can be measured by detection of insulin in a sample. The present invention concerns modified insulinotropic polypeptides that exceeds or equals the insulinotropic activity of the non-modified insulinotropic polypeptides. The insulinotropic property of an agent may be determined by providing that agent to animal cells, or injecting that agent into animals and monitoring the release of immunoreactive insulin (IRI) into the media or circulatory system of the animal, respectively. The presence of IRI is detected through the use of a radioimmunoassay which can specifically detect insulin.

Although any radioimmunoassay capable of detecting the presence of IRI may be employed, one specific method is to use a modification of the assay method of Albano, J. D. M., et al., (Acta Endocrinol. 70:487-509 (1972)). In this modification, a phosphate/albumin buffer with a pH of 7.4 is employed. The incubation is prepared with the consecutive condition of 500 microliters of phosphate buffer, 50 microliters of perfusate sample or rat insulin standard in perfusate, 100 microliters of anti-insulin antiserum (Wellcome Laboratories; 1:40,000 dilution), and 100 microliters of [$^{125}$I] insulin, giving a total volume of 750 microliters in a 10×75-mm disposable glass tube. After incubation for 2-3 days at 4° C., free insulin is separated from antibody-bound insulin by charcoal separation. The assay sensitivity is generally 1-2 microliters U/ml. In order to measure the release of IRI into the cell culture medium of cells grown in tissue culture, one preferably incorporates radioactive label into proinsulin. Although any radioactive label capable of labeling a polypeptide can be used, it is preferable to use 3 H leucine in order to obtain labeling of proinsulin. Labeling can be done for any period of time sufficient to permit the formation of a detectably labeled pool of proinsulin molecules; however, it is preferable to incubate cells in the presence of radioactive label for a 60-minute time period. Although any cell line capable of expressing insulin can be used for determining whether a compound has an insulinotropic effect, it is preferable to use rat insulinoma cells, and especially RIN-38 rat insulinoma cells. Such cells can be grown in any suitable medium; however, it is preferable to use DME medium containing 0.1% BSA and 25 mM glucose.

The insulinotropic property of a hydrocarbon stapled polypeptide of the invention may also be determined by pancreatic infusion. The in situ isolated perfused rat pancreas preparation is a modification of the method of Penhos, J. C., et al. (Diabetes 18:733-738 (1969)). In accordance with such a method, fasted rats (preferably male Charles River strain albino rats), weighing 350-600 g, are anesthetized with an intraperitoneal injection of Amytal Sodium (Eli Lilly and Co., 160 ng/kg). Renal, adrenal, gastric, and lower colonic blood vessels are ligated. The entire intestine is resected except for about four cm of duodenum and the descending colon and rectum. Therefore, only a small part of the intestine is perfused, thus minimizing possible interference by enteric substances with insulinotropic immunoreactivity. The perfusate can be a modified Krebs-Ringer bicarbonate buffer with 4% dextran T70 and 0.2% bovine serum albumin (fraction V), and can be bubbled with 95% $O_2$ and 5% $CO_2$. A nonpulsatile flow, four-channel roller-bearing pump (Buchler polystatic, Buchler Instruments Division, Nuclear-Chicago Corp.) can be used, and a switch from one perfusate source to another can be accomplished by switching a three-way stopcock. The manner in which perfusion is performed, modified, and analyzed can follow the methods of Weir, G. C., et al., (J. Clin. Investigat. 54:1403-1412 (1974)), which are hereby incorporated by reference.

Pharmaceutical Compositions and Routes of Administration

One or more structurally constrained insulinotropic polypeptides of the instant invention can be used in a pharmaceutical composition for the prevention and/or treatment of type 2 diabetes and related disorders. Combinations of pharmaceutical agents are frequently used for the treatment of complex or dangerous diseases, such as diabetes. Treatment and prevention method provided herein can be performed using a combination of the structurally constrained insulinotropic polypeptides, which can be selected and combined to prevent the development of resistance, or can be selected and combined depending on the status and nature of the disorder in the subject. A pharmaceutical composition of the instant invention can include 2, 3, 4, 5, 6, 7, 8, 9, 10, 11, 12, 13, 14, 15, or more structurally constrained insulinotropic polypeptides. The structurally constrained peptides can also be combined with other agents, e.g., known treatments or therapies for treating diabetes.

As used herein, the compounds of this invention are defined to include pharmaceutically acceptable derivatives thereof. A "pharmaceutically acceptable derivative" means any pharmaceutically acceptable salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system, pancreas), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_{4+}$ salts. This invention also envisions the quaternization of any basic nitrogen-containing groups of the compounds disclosed herein. Water or oil-soluble or dispersible products may be obtained by such quaternization.

The compounds of the invention can, for example, be administered by injection, intravenously, intraarterially, subdermally, intraperitoneally, intramuscularly, or subcutaneously; or orally, buccally, nasally, transmucosally, intravaginally, cervically, topically, in an ophthalmic preparation, or by inhalation, with a dosage ranging from about 0.001 to about 100 mg/kg of body weight, or according to the requirements of the particular drug and more preferably from 0.5-10 mg/kg of body weight. The methods herein contemplate administration of an effective amount of compound or compound composition to achieve the desired or stated effect.

In a preferred composition, the insulinotropic polypeptides of the invention are formulated for oral delivery. Any suitable pharmaceutically acceptable excipients, carriers, solvents, stabilizers, etc. can be used for obtaining an oral formulation of the exenatide peptides of the invention. Oral delivery may be by any suitable means, including by tablet, pill, suspension, quick-release strips, etc.

The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the invention or a pharmaceutically acceptable salt thereof; an additional agent including for example, one or more therapeutic agents for the prevention and/or treatment of diabetes, including, but not limited to, insulin, sulfonylureas (tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), and gliclazide (Diamicron)), meglitinides (repaglinide (Prandin), nateglinide (Starlix)), Biguanides (metformin, phenformin, buformin), Thiazolidinediones, Alpha-glucosidase inhibitors, DPP-4 inhibitors, non-stapled Incretin mimetics, and Amylin analogues.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tween® or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, may also be advantageously used to enhance delivery of compounds of the formulae described herein.

The pharmaceutical compositions of this invention may be administered enterally for example by oral administration, parenterally, by inhalation spray, topically, rectally, nasally, buccally, vaginally or via an implanted reservoir, preferably by oral or vaginal administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases, or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional, and intracranial injection or infusion techniques.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of the invention may be administered topically or intravaginally. The pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. In still another embodiment, the pharmaceutical composition is formulated as a vaginal ring. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention. In one embodiment, the compound of the invention is administered vaginally as a prophylactic treatment for a sexually transmitted disease.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Effective dosages of the peptides or antibodies targeted hereto of the invention to be administered may be determined through procedures well known to those in the art which address such parameters as biological half-life, bioavailability, and toxicity.

A therapeutically effective dose refers to that amount of the compound or antibody sufficient to result in amelioration of symptoms or a prolongation of survival in a patient.

Methods of Treatment

The present invention provides for both prophylactic and therapeutic methods of treating a subject at risk of (or susceptible to) a disorder or having a disorder associated with abnormal or aberrant glucose homeostasis, including, for example, insulin-dependent diabetes mellitus (type 1 diabetes) and noninsulin-dependent diabetes mellitus (type 2 diabetes). As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

The polypeptides of the present invention may also be employed in combination with other pharmaceutical agents useful in the treatment of diabetes, impaired fasting glucose, impaired glucose tolerance, hyperglycemia, and obesity. Suitable agents include insulin secretagogues, insulin sensitizers, and metformin HCl.

The present invention includes methods for the treatment of diabetes and related diseases and conditions. One such method comprises the step of administering to a subject in need thereof, a therapeutically effective amount of one or more hydrocarbon stapled insulinotropic polypeptides of the invention.

Polypeptides of the invention may be used in methods of the invention to treat diseases, such as diabetes, including type 2 diabetes. Such methods may also delay the onset of diabetes and diabetic complications. Other diseases and conditions that may be treated or prevented using polypeptides of the invention in methods of the invention include: Maturity-Onset Diabetes of the Young (MODY) (Herman, et al., Diabetes 43:40 (1994)), Latent Autoimmune Diabetes Adult (LADA) (Zimmet, et al., Diabetes Med. 11:299 (1994)), impaired glucose tolerance (IGT) (Expert Committee on Classification of Diabetes Mellitus, Diabetes Care 22 (Supp. 1) S5 (1999)), impaired fasting glucose (IFG) (Charles, et al., Diabetes 40:796 (1991)), gestational diabetes (Metzger, Diabetes, 40:197 (1991), and metabolic syndrome X.

Polypeptides of the invention may also be used in methods of the invention to treat secondary causes of diabetes (Expert Committee on Classification of Diabetes Mellitus, Diabetes Care 22 (Supp. 1), S5 (1999)). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenyloin, thyroid hormone, .beta.-adrenergic agents, .alpha.-interferon and drugs used to treat HIV infection.

Polypeptides of this invention may also be useful for the treatment of bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The polypeptides of this invention may also be useful for treating physiological disorders related to, for example, regulation of insulin sensitivity, inflammatory response, plasma triglycerides, HDL, LDL, and cholesterol levels and the like.

The methods and polypeptides of the present invention may be used alone or in combination with additional therapies and/or compounds known to those skilled in the art in the treatment of diabetes and related disorders. Alternatively, the methods and polypeptides described herein may be used, partially or completely, in combination therapy.

Polypeptides of the invention may also be administered in combination with other known therapies for the treatment of diabetes, including PPAR agonists, sulfonylurea drugs, non-sulfonylurea secretagogues, alpha-glucosidase inhibitors, insulin sensitizers, insulin secretagogues, hepatic glucose output lowering compounds, insulin and anti-obesity drugs. Such therapies may be administered prior to, concurrently with or following administration of the compound of the invention. Insulin includes both long and short acting forms and formulations of insulin. PPAR agonist may include agonists of any of the PPAR subunits or combinations thereof. For example, PPAR agonist may include agonists of PPAR-alpha, PPAR-gamma, PPAR-delta or any combination of two or three of the subunits of PPAR. Such PPAR agonists include, for example, rosiglitazone and pioglitazone. Sulfonylurea drugs include, for example, glyburide, glimepiride, chlorpropamide, and glipizide. Alpha-glucosidase inhibitors that may be useful in treating diabetes when administered with a compound of the invention include acarbose, miglitol and voglibose. Insulin sensitizers that may be useful in treating diabetes when administered with a compound of formula (I) include thiozolidinediones and non-thiozolidinediones. Hepatic glucose output lowering compounds that may be useful in treating diabetes when administered with a compound of the invention include metformin, such as GLUCOPHAGE™ and GLUCOPHAGE XR™ Insulin secretagogues that may be useful in treating diabetes when administered with a compound of the invention include sulfonylurea and non-sulfonylurea drugs: GLP-1, GIP, PAC/VPAC receptor agonists, secretin, nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin. In one embodiment of the invention, polypeptides of the invention are used in combination with insulin secretagogues to increase the sensitivity of pancreatic beta cells to the insulin secretagogue.

Polypeptides of the invention may also be used in methods of the invention in combination with anti-obesity drugs. Anti-obesity drugs include beta-3 agonists, CB-1 antagonists, appetite suppressants, such as, for example, sibutramine (MERIDIA™), and lipase inhibitors, such as, for example, orlistat (XENICAL™).

Polypeptides of the invention may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Polypeptides of the invention may also be used in combination with anti-hypertensive drugs, such as, for example, β-blockers and ACE inhibitors.

Such co-therapies may be administered in any combination of two or more drugs (e.g., a compound of the invention in combination with an insulin sensitizer and an anti-obesity drug). Such co-therapies may be administered in the form of pharmaceutical compositions, as described above.

Kits

The present invention also encompasses a finished packaged and labeled pharmaceutical product or laboratory reagent. This article of manufacture includes the appropriate instructions for use in an appropriate vessel or container such as a glass vial or other container that is hermetically sealed. A pharmaceutical product may contain, for example, a compound of the invention in a unit dosage form in a first container, and in a second container, sterile water or adjuvant for injection. Alternatively, the unit dosage form may be a solid suitable for oral, transdermal, intranasal, intravaginal, cervical ring, or topical delivery.

In a specific embodiment, the unit dosage form is suitable for intravenous, intramuscular, intraperiteneal, intranasal, oral, intravaginal, cervical, topical or subcutaneous delivery. Thus, the invention encompasses solutions, solids, foams, gels, preferably sterile, suitable for each delivery route.

In another specific embodiment, the unit dosage form is suitable for oral administration. Thus, the invention encompasses solutions, solids, foams, gels, preferably sterile, suitable for the oral route.

As with any pharmaceutical product, the packaging material and container are designed to protect the stability of the product during storage and shipment. Further, the products of the invention include instructions for use or other informational material that advise the physician, technician, or patient on how to appropriately prevent or treat the disease or disorder in question. In other words, the article of manufacture includes instructions indicating or suggesting a dosing regimen including, but not limited to, actual doses, monitoring procedures (e.g. detection and quantitation of infection), and other monitoring information.

Specifically, the invention provides an article of manufacture including packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to prevent, manage, treat, and/or ameliorate one or more symptoms associated with a disease, or to stimulate an immune response to prevent a disease by administering specific doses and using specific dosing regimens as described herein.

The following examples are provided merely as illustrative of various aspects of the invention and shall not be construed to limit the invention in any way.

EXAMPLES

Example 1

Materials and Methods

Synthesis of Hydrocarbon Stapled Alpha Helical Polypeptides.

Figure 6A:
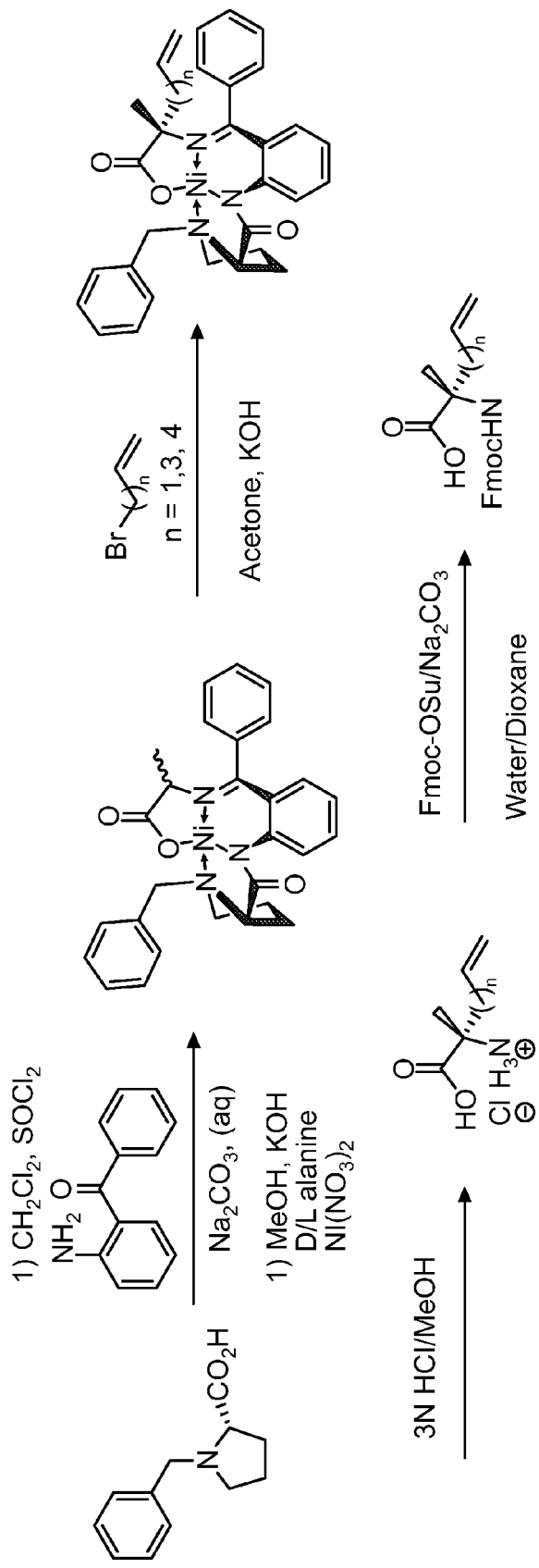
FIG. 6 shows a synthetic chemistry schema (A) for the syntheses of olefinic non-natural amino acids employed in the generation of i, i+3 staples. (B) Depicts examples of olefinic non-natural amino acids.
Figure 6B:

A combined strategy of structural analysis and chemical synthesis was applied to construct the modified, structurally constrained peptides. Asymmetric syntheses of (R)-Fmoc-(2'-pentenyl)alanine ("R5"), (S)-Fmoc-(2'-pentenyl)alanine ("S5"), (R)-Fmoc-(2'-octenyl)alanine ("R8"), (S)-Fmoc-(2'-octenyl)alanine ("R8") α,α-disubstituted amino acids were performed as previously reported (Schafmeister, C. E., J. Po, and G. L. Verdine, Journal of the American Chemical Society, 2000. 122(24): p. 5891-5892; Walensky, L. D., et al., Science, 2004. 305(5689): p. 1466-1470). Synthesis of (R) or (S) Fmoc-(2'-propenyl)alanine analogs were prepared using a new method as schematized in FIG. 6 and described below.

A solution of (R)-proline and KOH in isopropanol was prepared to which benzyl chloride was added and stirred at room temperature for 3 hr. An acidic workup allowed for isolation of a precipitate in 89% yield. This product was dissolved in ice cold methylene chloride, to which thionyl chloride and 2-aminobenzophenone was added to the reaction mixture and allowed to warm to room temperature with stirring over 10 hours. A basic workup yielded (R)-2-[N—(N'-benzylprolyl)amino]benzophenone (BPB) in 81% yield. A solution of KOH in MeOH was poured into a stirred mixture of BPB, Ni(NO$_3$)2-6H$_2$O, alanine in MeOH under inert gas at 40° C. The resulting mixture was stirred for 2 h and an acidic workup yielded Ala-Ni(II)-BPB-complex in 91% yield. (*Tetrahedron:Asymmetry* 9 (1998) 4249-4252)

The Ala-Ni(II)-BPB-complex was reacted with 3-bromo-1-propene in acetone under basic conditions to give a mixture of a Ni(II) complex of Schiff base of (R)-BPB-(R)-trans-(2'-propenyl)alanine [(R)-2] and Ni(II) complex of Schiff base of (S)-BPB-(S)-trans-(T-propenyl)-alanine [(S)-2] with ratio 6:1.

After separation with silica gel column, diastereopure (R)-2 complexes were obtained at 44% yield. The (R)-2 complexes were decomposed with 3N HCl/MeOH to afford (R)—(2'-propenyl)alanine as well as a chiral ligand which was extracted with DCM. After work up, (R)—(2'-propenyl) alanine was protected with Fmoc-OSu to give the (R)-Fmoc-(T-propenyl)alanine with 93% yield (two steps). (Tetrahedron 56 (2000) 2577-2582)

The modified polypeptide compounds were generated by replacing at least two naturally occurring amino acids with the α,α-disubstituted non-natural amino acids at discrete locations flanking either 2, 3 or 6 amino acids, namely the "i, i+3," "i, i+4" or "i, i+7" positions, respectively.

Locations for the non-natural amino acids and subsequent hydrocarbon staple(s) were carefully chosen so as not to interfere with critical GLP-1 receptor interactions or replace residues known to be critical for insulinotropic activity (FIGS. 2 and 3).

The modified polypeptides, SAH-Ex and SAH-GLP1 (FIG. 7), were generated using solid phase Fmoc chemistry and ruthenium-catalyzed olefin metathesis, followed by peptide deprotection and cleavage, purification by reverse-phase high performance liquid chromatography, and chemical characterization using LC/MS mass spectrometry and amino acid analysis.

Alternatively an established fragment-based approach can be pursued ([Bray, B. L. *Nature Reviews Drug Discovery*, 2003. 2(7): p. 587-593; MYUNG-CHOL KANG, B. B., et al., *Methods and compositions for peptide synthesis*, U.S.P.a.T. Office, Editor. Jan. 18, 2000 USA). In this strategy, the peptide is divided into 3 fragments, such that an N-terminal, central, and C-terminal portion are synthesized independently. These polypeptide fragments should be generated using solid phase Fmoc chemistry and ruthenium-catalyzed olefin metathesis on super-acid cleavable resins, which yields fully protected peptides having an Fmoc at the N-terminus, and either a C-terminal amide (for the C-terminal fragment) or a free carboxylate (for the central and N-terminal fragments). These fully protected fragments are purified by reverse-phase high performance liquid chromatography, followed by sequential deprotection, coupling, and purification, to yield the full length, fully protected polypeptides. Global deprotection, followed by reverse-phase high performance liquid chromatography will yield the final products, which can be characterized using LC/MS mass spectrometry and amino acid analysis.

Peptides were produced on an Apex 396 (Aapptec) automated peptide synthesizer using Rink amide AM LL resin (EMD Biosciences, 0.2 mmol/g resin), at 50 mmol scale. The standard Fmoc protocol employed 2×10 min deprotections in 20% piperidine/NMP followed by a pair of consecutive methanol and dimethylformamide (DMF) washes. The incorporated non-natural amino acids were treated with 4×10 min incubations in 20% piperidine/NMP to achieve complete deprotection. Amino acid coupling was performed using 0.4 M stock solutions of Fmoc-protected amino acids, 0.67 M 2-(6-chloro-1H-benzotriazole-1-yl)-1,1,3,3-tetramethylaminium hexafluorophosphate (HCTU), and 2 M N,N-diisopropyl ethylamine (DIEA), yielding 1 mL of 0.2 M active ester (4 equivalents). Coupling frequency and incubation times were 2×30 min for standard residues, 2×45 min for the olefinic non-natural amino acids, and 3×45 min for the residue following a non-natural amino acid. The olefin metathesis step is carried out by first swelling the resin with 1,2-dichloroethane followed by exposure to a 10 mM solution of bis tricyclohexylphosphine)-benzylidene ruthenium(IV) dichloride (Grubbs' first generation catalyst) in 1,2-dichloroethane (0.20 mol % on the basis of resin substitution) for 2 h. The stapling reaction is carried out twice. The resin-bound peptide is then washed with 1,2-dichloroethane three times and dried under a stream of nitrogen. The completed peptide is cleaved from the resin and deprotected by exposure to trifluoroacetic acid (TFA)-based cleavage cocktails such as TFA/triisopropyl silane (TIS)/water (95%, 2.5%, 2.5%), and precipitated with methyl-tert-butyl ether followed by lyophilization. Lyophilized SAHB peptides are purified by reverse-phase HPLC by use of a C18 column. The compounds are characterized by LC/MS, with mass spectra obtained by electrospray in positive ion mode. Quantitation is achieved by amino acid analysis on a Beckman 6300 high-performance amino acid analyzer.

Determining the Secondary Structure and Thermal Stability of the Modified Polypeptides.

The alpha-helicity of stapled modified polypeptides was compared to their unmodified counterparts by circular dichroism. CD spectra were obtained on an Aviv spectropolarimeter at 20° C. using the following standard measurement parameters: wavelength, 190-260 nm; step resolution, 0.5 nm; speed, 20 nm/sec; accumulations, 10; response, 1 sec; bandwidth, 1 nm; path length, 0.1 cm. The alpha-helical content of each peptide was calculated by dividing the mean residue ellipticity $[\Theta]222_{obs}$ by the reported $[\Theta]222_{obs}$ for a model helical peptide (Forood, B., E. J. Feliciano, and K. P. Nambiar, *PNAS*, 1993. 90(3): p. 838-842; J. Martin Scholtz, *Biopolymers*, 1991. 31(13): p. 1463-1470; Lawless, M. K., et al., *Biochemistry*, 1996. 35(42): p. 13697-13708) or using, for example, the Aviv machine using CDNN software developed by Brohm in order to deduce five different secondary structure fractions (helix, parallel and antiparallel beta-sheet, beta-turn and random coil). Protein Engineering, 1992. 5(3); p. 191-195. Thermal stability is assessed by acquiring circular dichroism spectra across a broad temperature range and determining the melting temperatures for each constrained peptide.

Optimization of the Biophysical and Biochemical Properties of the Modified Polypeptides by Evaluating Diversified Modified Peptide Libraries Synthesized in High-Throughput Fashion.

High-throughput technologies were used to optimize the modified polypeptides activities for cellular and in vivo studies. For example, an Apex 396 multichannel synthesizer (AAPPTEC; Louisville, Ky.) was used to produce polypeptide libraries for biological evaluation. The polypeptide compounds were diversified by extension, truncation, or amino acid substitution across natural and select non-natural amino acids, and differential staple localization were made to maximize desirable biophysical and biochemical properties. The libraries were generated using high-throughput solid phase Fmoc chemistry and ruthenium-catalyzed olefin metathesis and peptide deprotection and cleavage. Peptide purification was achieved by reverse phase C18 HPLC, and products characterized by LC/MS mass spectrometry and amino acid analysis.

Protease Resistance Assays

In vitro proteolytic degradation of structured peptides was measured by LC/MS (Agilent 1200) using the following parameters: 20 µL injection, 0.6 mL flow rate, 15 min run time consisting of a gradient of water (0.1% formic acid) to 20-80% acetonitrile (0.075% formic acid) over 10 min, 4 min wash to revert to starting gradient conditions, and 0.5 min post-time. The DAD signal was set to 280 nm with an 8 nm bandwidth and MSD set to scan mode with one channel at (M+2H)/2, +1 mass units and the other at (M+3H)/3, +1 mass units. Integration of each MSD signal yielded areas under the curve of $>10^8$ counts. Reaction samples were composed of 5 µL peptide in DMSO (1 mM stock) and 195 µL of buffer consisting of 50 mM phosphate buffer pH 7.4 containing 2 mM $CaCl_2$. Upon injection of the 0 hr time point sample, 2 µL of 50 ng/µL chymotrypsin (Sigma) was added and the amount of intact peptide quantitated by serial injection over time. An internal control of acetylated tryptophan carboxamide at a concentration of 100 µM was used to normalize each MSD data point. A plot of MSD area versus time yielded an exponential decay curve and half-lives were determined by non-linear regression analysis using Prism software (GraphPad). The assay was also performed using trypsin and pepsin in their appropriate buffer conditions.

Plasma Stability and Pharmacokinetics

Peptides are incubated (5-10 µg) with mouse plasma at 37° C., injected (10, 20 mg/kg) by tail vein, or administered by oral gavage to male C57/BL6 mice. Ex vivo and in vivo samples (withdrawn by retro-orbital bleed) at various time intervals (e.g. 0.5, 1, 2, 4, 8, 12 hr; n=3 per time point) are processed for quantitation by LC/MS analysis or available ELISA kits (e.g. Exendin-4 (*Heloderma suspectum*) EIA Kit Phoenix Pharmaceuticals, Inc. EK-070-94). For ex vivo serum stability studies, peptide half-lives are calculated by nonlinear regression analysis of exponential decay curves plotted using Prism software (Graphpad). In vivo plasma concentrations at the indicated time points are used to calculate plasma half-life, peak plasma levels, total plasma clearance, and apparent volume of distribution using noncompartmental analysis. The derived protease-resistance and PK profiles serve as a measure for selecting the most stable structured peptides for in vivo application.

GLP-1 Receptor Binding Assay.

Recombinant U2OS cells that stably express human GLP1 receptor fused to the N-terminus of enhanced green fluorescent protein (EGFP) are employed in a GLP-1R Redistribution Assay (Thermo Scientific), performed according to the manufacturer's instructions. The GLP-1R assay is used to screen for stapled insulinotropic polypeptide agonists that optimally trigger internalization of GLP1R. GLP-1 is used as a reference compound in the assay, and the ligands are assayed for their ability to induce GLP-1R internalization by a spot detecting image analysis algorithm. The translocation of GLP-1R-EGFP is imaged on a fluorescence microscope. The filters are set for Hoechst (350/461 nm) and GFP/FITC (488/509 nm) (wavelength for excitation and emission maxima). The translocation is analyzed on images taken with a 20× objective or higher magnification. The primary output in the GLP-1R Redistribution assay is the formation of spots in the cytoplasm. The data analysis therefore report an output that corresponds to number, area or intensity of spots in the cytoplasm.

GLP-1 Receptor Engagement Second Messenger Signaling Assays.

GLP-1R agonists have previously been shown to either prevent or ameliorate experimental diabetes and preserve β-cell mass in multiple preclinical models. Accordingly, the expression of markers important for the response to ER stress in cells treated with vehicle alone or with stapled insulinotropic polypeptides can be examined. ER stress activates signaling pathways invoked by the unfolded protein response involving phosphorylation of many signaling protein such as ATF-4, XBP-1, phospho-eIF2a Ser51 (P[Ser51]-eIF2a), and CHOP (Druker, et. al., *Cell Metabolism*, 2006 v4 p 391-406). As such, Rat INS-1 or mouse MIN6 insulinoma cells are treated with vehicle alone, thapsigargin, or tunicamycin in the absence or presence of serial dilutions of stapled insulinotropic polypeptides for up to 4 hr. Alternatively, cultures are exposed to vehicle alone or to either H89, U0126, or LY294002 for 20 min prior to and during the 4 hr treatment with thapsigargin in the absence or presence of stapled insulinotropic polypeptides. Total cell extracts are analyzed by immunoblotting for ATF-4, XBP-1, phospho-eIF2a Ser51 (P[Ser51]-eIF2a), and CHOP with respect to time.

Glucose-Stimulated Insulin Release Cellular Assay.

INS-1 cells are cultured overnight in Dulbecco's modified Eagle's medium containing 5 mM glucose and 10% fetal calf serum in the presence of diluent alone or various concentrations of stapled insulinotropic polypeptides. After preincubation in the presence of 3.3 mM glucose, cells are then incubated in the presence of either 3 or 20 mM glucose for 45 min at 37° C. The supernatant is then removed, centrifuged at 300 g for 10 min, and assayed for insulin. To assess insulin content, cells are extracted overnight in acid/ethanol mixture as described previously. The amount of insulin is then quantitated by ELISA (American Laboratory Products Company, Amin, et., al., *The Journal of Pharmacology and Experimental Therapeutics*, 2002, v303, p 82-88).

In Vivo Monitoring of Serum Glucose and Insulin Levels in Response to Insulinotropic Peptide Treatment.

Db/db mice (C57BLKS/J-Leprdb/Leprdb) lacking the leptin receptor and their non-diabetic littermates are purchased at 4 weeks of age from Jackson Laboratories (Bar Harbor, Mass., USA). They are housed, two per cage, and also fed ad libitum. The same mice are caged together for the duration of the study. After 2 days of acclimatization to our facilities, whole blood glucose concentrations, taken from a retro-orbital sinus, are determined using a Glucometer Elite (Bayer, Elkhart, Ind., USA). We administer insulinotropic polypeptides (e.g. 24 nmol/kg exendin-4 i.p. daily) to 6 diabetic and 6 non-diabetic animals thereafter (0700-0900 hours) and 10 diabetic and 10 non-diabetic animals receive NaCl i. p. This regimen is continued for 8 days. Animals are weighed daily and blood samples are taken from a retro-orbital sinus for determination of insulin and glucose concentrations. At the end of the regimen, fasting blood samples are obtained for these concentrations and whole blood containing EDTA was assayed for HbA1c (Greig, et. al., *Diabetologia*, 1999 v42, p 45-50). The identical experiment is also performed using oral gavage administration of insulinotropic polypeptides (unmodified control and stapled derivatives).

Example 2

Singly and Doubly Stapled Exenatide Peptides Demonstrate Enhanced α-Helicity Compared to the Unmodified Template Peptide (FIG. 8)

To measure the effect of hydrocarbon stapling on the α-helical structure of exenatide peptides, we analyzed exenatide (Met14NorLeu), SAH-Ex(A), SAH-Ex (B), and SAH-Ex(A, B) by circular dichroism. The unmodified exenatide template peptide was predominantly unstructured in pH 7 aqueous solution at 21° C., exhibiting less than 25% α-helicity. All stapled derivatives displayed comparatively increased α-helical content. The insertion of either one or two hydrocarbon staples consistently transformed the circular dichroism spectra from a random coil pattern with a predominant single minimum at 204 nm to an α-helical contour with double minima at 208 and 222 nm.

Example 3

Singly and Doubly Stapled Exenatide Peptides Demonstrate Enhanced Thermal Stability Compared to the Unmodified Template Peptide (FIG. 8)

To assess the resistance of SAH-Ex peptides to thermal unfolding, we performed circular dichroism studies across a 5-83° C. temperature range for all constructs. None of the peptides demonstrated classical cooperative unfolding with increasing temperature, but instead showed incremental melting as a function of temperature. All SAH-Ex peptides retained a greater degree of α-helicity across the entire temperature range. Whereas the slopes of exenatide (Met14NorLeu), SAH-Ex(A), and SAH-Ex(B) were similar, SAH-Ex(A, B) had a flatter sloped line, indicating that the α-helicity of the doubly stapled peptide helicity was least effected by increasing temperature and reflecting a robust thermal stability.

Example 4

Singly and Doubly Stapled Exenatide Peptides Demonstrate Enhanced Proteolytic Stability at Neutral and Acidic pH Compared to the Unmodified Template Peptide (FIG. 9, 10)

A major limitation of peptides as therapeutics is their susceptibility to rapid proteolytic degradation. Biologically active peptides such as exenatide and GLP-1 that are lengthy, partially or predominantly unfolded, and replete with protease sites are particularly vulnerable. One of the potential benefits of a covalent crosslinking strategy to enforce peptide α-helicity is shielding of the vulnerable amide bonds from proteolysis. Because proteases require that peptides adopt an extended conformation to hydrolyze amide bonds, the structural constraint afforded by the hydrocarbon staple can render crosslinked peptides protease-resistant. To determine if hydrocarbon stapling could protect the 39-mer exenatide peptide from proteolysis, we subjected exenatide (Met14NorLeu), and singly and doubly stapled derivatives to direct protease exposure in vitro. In the presence of 0.5 ng/μL chymotrypsin, Ex4 (25 μM) exhibited relatively rapid degradation, with a half-life of 38 minutes. In comparison, singly stapled SAH-Ex(A) and SAH-Ex(B) compounds longer half-lives of 94 and 128 minutes, respectively. The doubly stapled peptide SAH-Ex(A, B) displayed a half-life of 295 minutes, surpassing its singly stapled counterparts by up to 4-fold and the exenatide template peptide by 8-fold. Notably, double stapling itself had a stronger influence on proteolytic stability than overall peptide α-helicity, as the doubly stapled peptide had a lower percent α-helicity than the corresponding singly stapled peptides yet exhibited superior protease resistance.

Peptides have poor oral bioavailability in part due to rapid acid hydrolysis in the proximal digestive tract. The enhanced protease resistance of stapled SAH-Ex peptides at neutral pH prompted us to explore their stability under acidic conditions. Upon exposure to pepsin at 0.5 ng/μL, exenatide (Met14NorLeu exhibited rapid degradation, with a half-life of 13 minutes. Whereas N-terminal stapling did not enhance pepsin resistance in this example, stapling within the C-terminal portion of the peptide resulted in increasing the half-life to 81 minutes, representing a more than 6-fold improvement over the unmodified template peptide. As with chymotrypsin resistance at pH 7, the double-stapled peptide, SAH-Ex(A, B), exhibited striking pepsin resistance at pH 2, displaying a half-life of 172 minutes, representing a 13-fold improvement over the unmodified exenatide peptide template.

Example 5

Figure 11:
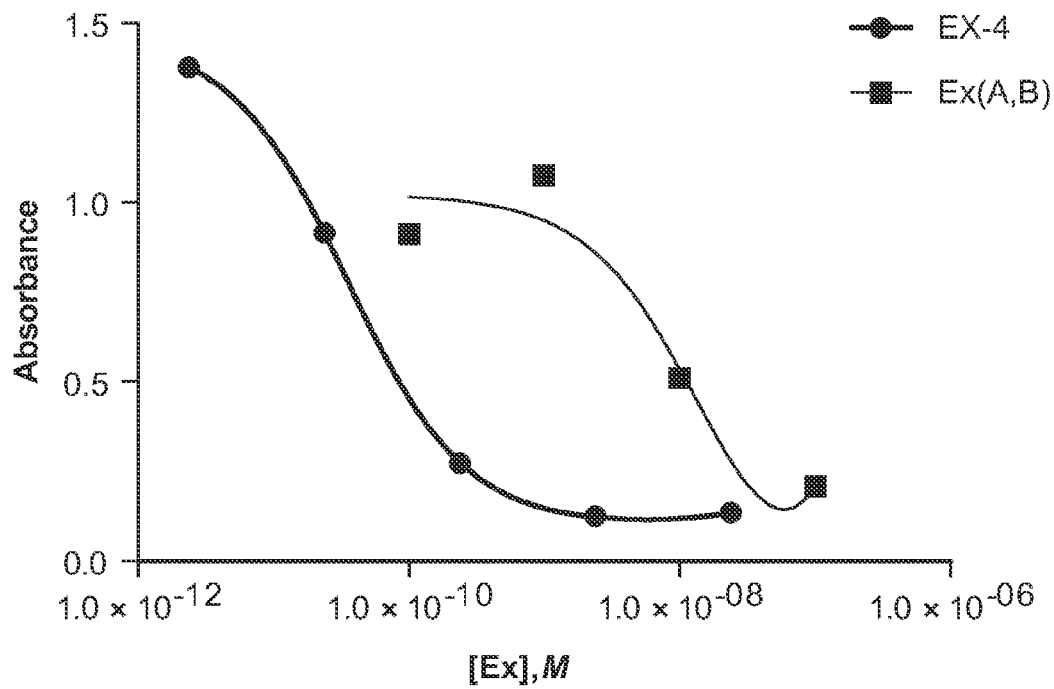
FIG. 11 illustrates the results of an ELISA-based assay for the detection of stapled SAH-Ex of the invention. Specifically, the graph demonstrates that an exenatide ELISA-based assay kit detects serially diluted unmodified Ex(Met14NorLeu) and doubly-stapled SAH-Ex(A,B) polypeptides. (Exendin-4 (*Heloderma suspectum*), EIA Kit Phoenix Pharmaceuticals, Inc. EK-070-94). As demonstrated, exenatide ELISA assay recognizes the template mutant exenatide peptide and its doubly stapled derivative, enabling the measurement of SAH-Ex levels in plasma.
Figure 12:
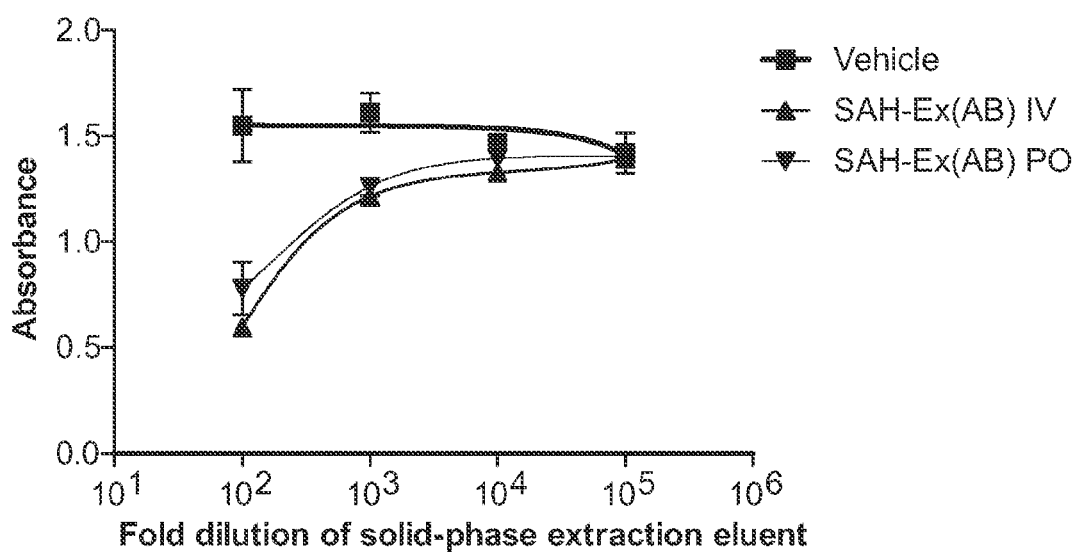
FIG. 12 demonstrates detection of full-length doubly stapled SAH-Ex peptide in the plasma of mice treated by either oral gavage or intravenous injection. Equivalent levels of full-length SAH-Ex peptide were detected for both routes of administration. Mice treated with vehicle only served as a negative control.

A Doubly Stapled Exenatide Peptide Affords Similar Serum Levels Whether Administered by Intravenous Injection or Oral Gavage Delivery (FIG. 11, 12)

The exendin-4 EIA kit (Phoenix Pharmaceuticals, Inc. EK-070-94) successfully recognized the template exenatide (Met14NorLeu) peptide and its doubly stapled derivative, enabling the measurement of SAH-Ex(A,B) levels in plasma (FIG. 11). In this competition ELISA, serially diluted exenatide peptide derivatives compete with biotinylated control exendin-4 peptide for an immobilized antibody; competition results are read-out by use of streptavidin-HRP-based detection of biotinylated peptide and effective competition is reflected by decreased absorbance due to replacement of the biotinylated-exendin-4 by SAH-Ex peptide in the immobilized antibody complex.

For in vivo detection studies, SAH-Ex(A,B) was dissolved in sterile aqueous 5% dextrose (1 mg/mL) and administered to 8-10 week old male C57BL/6 mice (Jackson Laboratory, 3 animals per treatment group) by either bolus tail vein injection (4 mg/kg, 125 mcg) or oral gavage (4 mg/kg, 125 mcg). An additional cohort of mice was treated with vehicle alone. At 30 min after treatment, blood was withdrawn by retroorbital puncture in sufficient quantity to yield ~200 μL of serum after clotting on ice and then centrifugation at 20,000 g for 1 min at 4° C. The serum samples were purified using C18 solid-phase extraction columns (Phoenix Pharmaceuticals) according to the manufacturer's protocol. The water-acetonitrile elution was lyophilized overnight and reconstituted in 0.5 mL buffer from the ELISA kit. This reconstituted solution was subsequently diluted serially by 10-fold and subjected to EIA analysis per the manufacturer's protocol. Strikingly, an equivalent amount of SAH-Ex(A,B) was detected in the plasma of mice treated with either intravenous or oral gavage dosing, highlighting the remarkable capacity of double-stapling to transform an exenatide peptide into an orally bioavailable form that is absorbed by the gastrointestinal system into the systemic circulation, a route of delivery previously unachievable for unmodified exenatide (Gedulin et al., *Int'l J Pharmaceuticals*, 356 (2008) 231-238). As a negative control, no signal was detected by EIA in serum from the vehicle-treated animals.

Example 6

Structural Determination of Stapled Insulinotropic Peptides

To define the explicit structure of stapled insulinotropic peptides bound to the GLP-1 receptor x-ray crystallography methods will be applied as described (Runge, S et al. 2008 *J Biol Chem*, 283:11340-11347). Crystallization conditions for stapled insulinotropic peptides are screened using 96-well sitting drop plates (Crystal Quick, Hampton Research) set up using a Phoenix crystallization robot. Initial conditions include HT Index Screen (Hampton Research), JSCG+ Suite (Qiagen) and Pro-Complex Suite (Qiagen). Screening around the best hit, including varying pH and salt and detergent concentrations, are performed to identify the best condition for crystal growth. Once generated, the crystals are removed, washed in the crystallization buffer, and subjected to mass spectroscopy to verify the presence of peptide within the crystal. The crystal is then soaked in cyroprotectant, flash frozen, and stored in liquid nitrogen. Suitable crystals are examined at the Argonne National Laboratory synchrotron facility. Phases are obtained by molecular replacement followed by data analysis and refinement (Phaser, Phenix, and Coots software).

An alternative and complementary approach for structural analysis employs $^1$H-NMR analysis. Spectra of stapled insulinotropic peptides in solution are acquired on a Bruker Avance DRX spectrometer at 600 MHz equipped with a z-shielded gradient and triple resonance cryoprobe. Two dimensional DQF-COSY, TOCSY, and NOESY spectra are measured in 100% $D_2O$ and 90% $H_2$/10% $D_2O$. The TOCSY datasets are acquired with mixing times of 40 and 80 ms and NOESY spectra with mixing times of 75, 100, 125 and 200 ms. NMR data sets are processed with the NMRPipe spectral analysis package and assignment of proton resonances is performed with Cara. Structure calculations are carried out with the program CYANA using the standard protocol. The final structure family is comprised of the 20 structures with the lowest target function and the best overall values for chirality and stereochemistry measured with the programs WHATCHECK and PROCHECK_NMR. Structures are displayed and analyzed using the programs PYMOL and MOLMOL.

The structural data are used to correlate stapled insulinotropic peptide structure, individually and in complex with GLP-1R, with functional activity as evaluated in the assays described herein.

Example 7

Mechanism of Proteolytic Resistance Conferred by Insertion of Hydrocarbon Staples (FIG. 13)

Figure 13A:
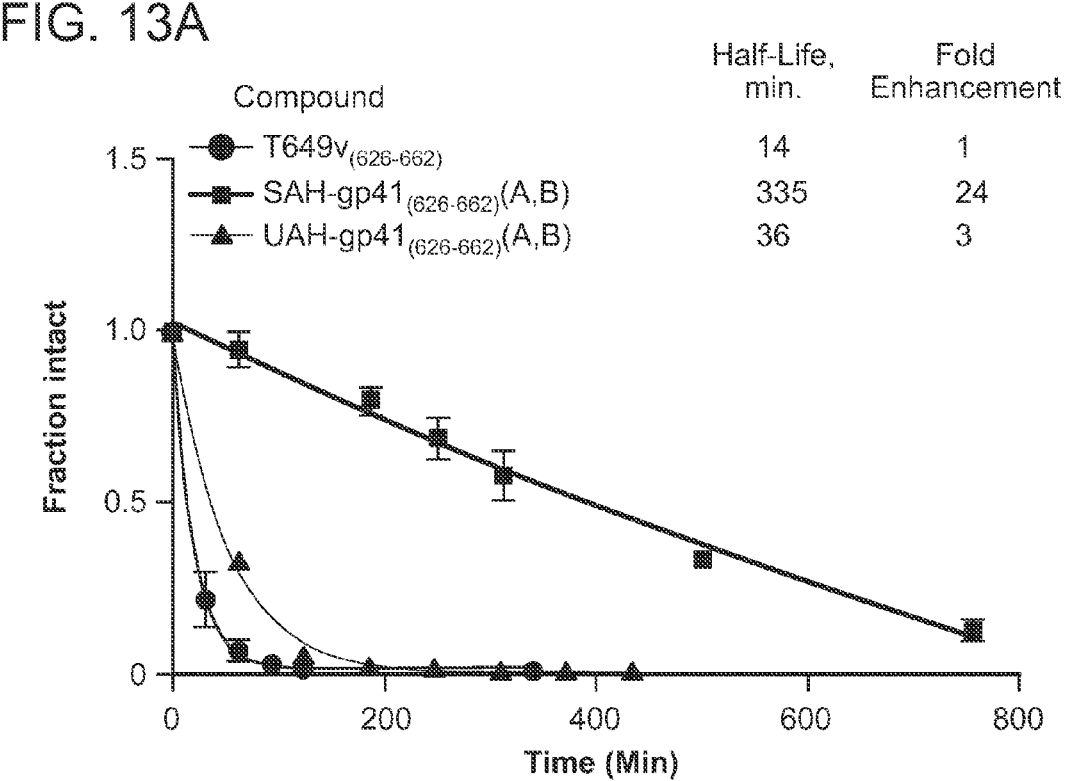
FIG. 13 demonstrates the mechanism of proteolytic resistance conferred by insertion of hydrocarbon staples. (A) Insertion of the two pairs of olefinic non-natural amino acids without crosslinking (e.g. Unstapled Alpha Helix of gp41: UAH-gp41$_{(626-662)}$(A,B)) does not confer significant protection from chymotrypsin proteolysis. However, upon olefin metathesis, the corresponding doubly stapled analog, SAH-gp41$_{(626-662)}$(A,B), exhibited an 8-fold longer half-life than UAH-gp41$_{(626-662)}$(A,B), indicating that the staples themselves are required to confer the striking protease resistance. (B) UAH- and SAH-gp41$_{(626-662)}$(A,B) displayed similar circular dichroism melting profiles, with $T_m$ values of 27° C. and 22° C., respectively. Temperature-dependent unfolding was reversible for both peptides, as evidenced by the overlapping repeat melting curves. These data demonstrate that overall alpha-helical stabilization, which is similar for the two constructs, does not account for the striking protease resistance of SAH-gp41$_{(626-662)}$(A,B). In addition, the reversibility of unfolding highlights the absence of peptide aggregation, which likewise cannot account for the striking protease resistance of SAH-gp41$_{(626-662)}$(A,B). (C) Comparative chymotrypsin degradation patterns of unmodified, singly stapled, doubly stapled, and 4-place substituted but unstapled peptides. These data demonstrate that the N-terminal staple uniquely prevented proteolytic hydrolysis of the cleavage site flanked by the staple, with no corresponding M+18 species observed by LC/MS analysis. The C-terminal staple slowed, rather than completely blocked, proteolysis at sites upstream of the staple. The 4-place substituted but unstapled derivative UAH-gp41$_{(626-662)}$(A,B) was not capable of blocking proteolysis at the position flanked by the N-terminal pair of non-natural amino acids, nor slow the rate of proteolysis as effectively as the C-terminal singly stapled peptide ($T_{1/2}$ 77 min for SAH-gp41$_{(626-662)}$(B); $T_{1/2}$ 36 min for UAH-gp41$_{(626-662)}$(A,B)). The doubly stapled peptide SAH-gp41$_{(626-662)}$(A,B) synergistically benefited from the anti-proteolysis features of both the N-terminal and C-terminal staples. (D) Comparative $^1$H NMR analysis of SAH-gp41$_{(626-662)}$(A,B) and the corresponding unmodified template peptide, T649v. The indole protons (~10.6 p.p.m) corresponding to the two N-terminal tryptophan residues of T649v are represented by two sharp peaks in T649v, consistent with fast exchange between multiple conformations. In contrast, the indole proton peaks in the $^1$H NMR spectrum of SAH-gp41$_{(626-662)}$(A,B) are broadened and split, reflective of a discretely structured N-terminus as a result of peptide stapling. Although this mechanistic dissection specifically involved doubly-stapled HIV-related polypeptides, similar anti-proteolysis and structural reinforcement results were obtained for the doubly stapled insulinotropic polypeptides of the invention (FIGS. 8-10).
Figure 13B:
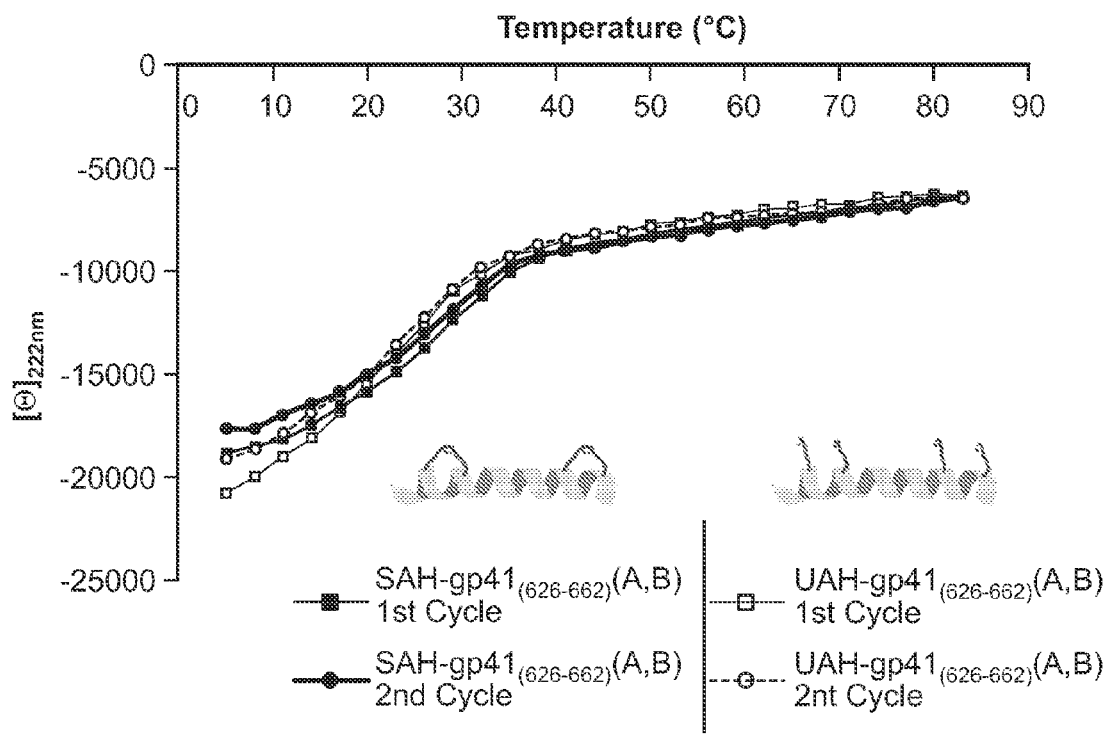
Figure 14A:
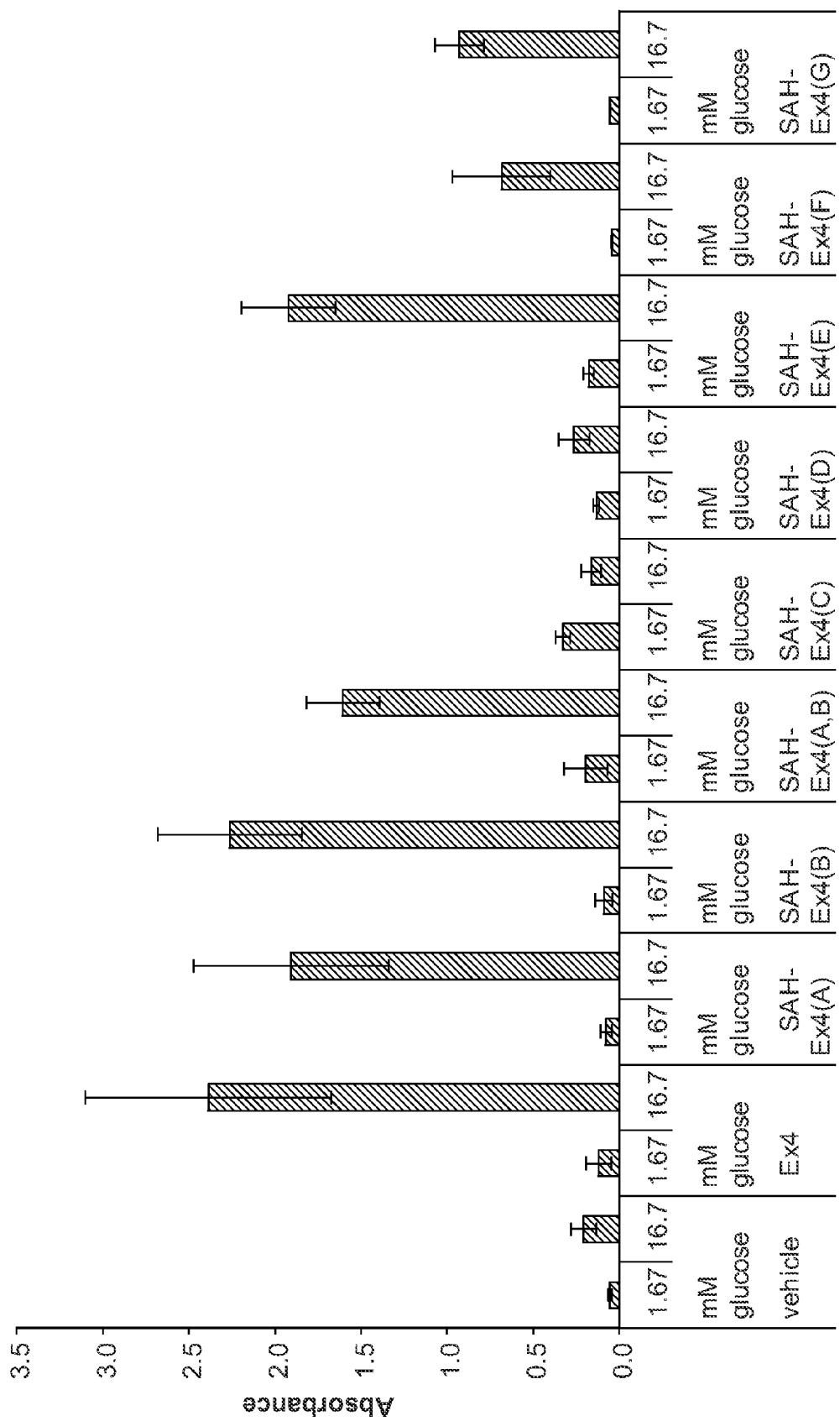
FIG. 14 demonstrates that structurally-stabilized and protease resistant SAH-Ex (A) and SAH-GLP1 (B) peptides stimulate glucose-stimulated insulin release from isolated pancreatic islets. These data highlight that hydrocarbon stapling of SAH-Ex and SAH-GLP1 peptides preserves functional activity while maximizing structural stability and protease resistance, yielding pharmacologically optimized insulin secretagogues.
Figure 14B:
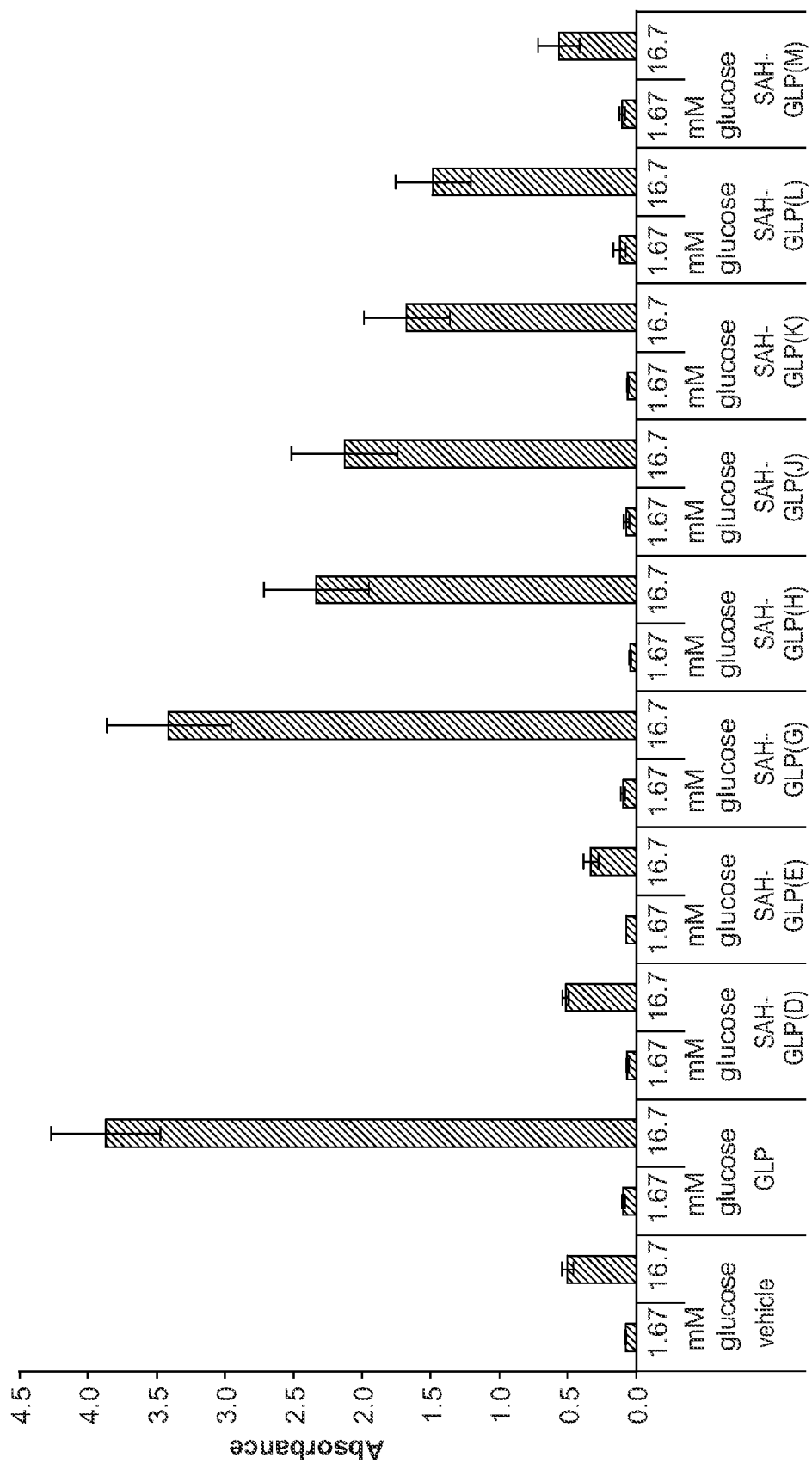

The mechanism by which hydrocarbon stapling confers protease resistance to a lengthy peptide therapeutic was explored using a gp41-derived HIV-1 fusion inhibitor peptide template. Insertion of the two pairs of olefinic non-natural amino acids without crosslinking (e.g. Unstapled Alpha Helix of gp41: UAH-gp41$_{(626-662)}$(A,B)) does not confer significant protection from chymotrypsin proteolysis. However, upon olefin metathesis, the corresponding doubly stapled analog, SAH-gp41$_{(626-662)}$(A,B), exhibited an 8-fold longer half-life than UAH-gp41$_{(626-662)}$(A,B), indicating that the staples themselves are required to confer the striking protease resistance (FIG. 13A). UAH- and SAH-gp41$_{(626-662)}$(A,B) displayed similar circular dichroism melting profiles, with $T_m$ values of 27° C. and 22° C., respectively. Temperature-dependent unfolding was reversible for both peptides, as evidenced by the overlapping repeat melting curves (FIG. 13B). These data demonstrate that overall alpha-helical stabilization, which is similar for the two constructs, does not account for the striking protease resistance of SAH-gp41$_{(626-662)}$(A, B). In addition, the reversibility of unfolding highlights the absence of peptide aggregation, which likewise cannot account for the striking protease resistance of SAH-gp41$_{(626-662)}$(A,B).

Comparative chymotrypsin degradation patterns of unmodified, singly stapled, doubly stapled, and 4-place substituted but unstapled peptides revealed that the N-terminal staple uniquely prevented proteolytic hydrolysis of the cleavage site flanked by the staple, with no corresponding M+18 species observed by LC/MS analysis (FIG. 13C). The C-terminal staple slowed, rather than completely blocked, proteolysis at sites upstream of the staple. The 4-place substituted but unstapled derivative UAH-gp41$_{(626-662)}$(A,B) was not capable of blocking proteolysis at the position flanked by the N-terminal pair of non-natural amino acids, nor slow the rate of proteolysis as effectively as the C-terminal singly stapled peptide ($T_{1/2}$ 77 min for SAH-gp41$_{(626-662)}$(B); $T_{1/2}$ 36 min for UAH-gp41$_{(626-662)}$(A,B)). The doubly stapled peptide SAH-gp41$_{(626-662)}$(A,B) synergistically benefited from the anti-proteolysis features of both the N-terminal and C-terminal staples.

Comparative $^1$H NMR analysis of SAH-gp41$_{(626-662)}$(A, B) and the corresponding unmodified template peptide, T649v revealed that the indole protons (~10.6 p.p.m) corresponding to the two N-terminal tryptophan residues of T649v are represented by two sharp peaks in T649v, consistent with fast exchange between multiple conformations (FIG. 13D). In contrast, the indole proton peaks in the $^1$H NMR spectrum of SAH-gp41$_{(626-662)}$(A,B) are broadened and split, reflective of a discretely structured N-terminus as a result of peptide stapling. Taken together, these data indicate that the proteolytic advantage conferred by peptide double-stapling does not derive from mutagenesis of protease cleavage sites, maximizing α-helicity alone, 4-place non-natural amino substitution, or peptide aggregation. Instead, we determined that the striking protease resistance of doubly-stapled peptides is conferred by a combination of (1) decreased rate of proteolysis due to induction of α-helical structure and (2) complete blockade of peptidase cleavage at sites localized within or immediately adjacent to the (i, i+4)-crosslinked segment.

Example 8

Structurally-Stabilized and Protease Resistant SAH-Ex and SAH-GLP Peptides Enhance Glucose-Stimulated Insulin Release (GSIS)

Stock solutions of SAH-Ex and SAH-GLP peptides were generated by dissolving the lyophilized powders in deionized water at 100 μM. The following treatment solutions were made for batch GSIS assays: 1.67 mM glucose, 16.7 mM glucose, 1.67 mM glucose+10 nM peptide, 16.7 mM glucose+10 nM peptide all in 1×KRB buffer, 2 mM CaCl$_2$, 0.05% BSA. Islets isolated from wild-type mouse pancreas were washed 3 times with KRB buffer and 5 islets per experimental tube were incubated in KRB buffer containing 1.67 mM glucose for 30 min at 37° C. Islets were then pelleted and the buffer replaced with the treatment solutions listed above. Each experimental condition was examined in replicates of n=8. After 1 hour incubation at 37° C., islets were pelleted and the supernatants collected for glucose stimulated insulin release measurement. The pellets are solubilized to assess intracellular insulin content to normalize for cell number. Insulin was measured by ELISA using mouse insulin as a standard (Insulin ELISA Kit, cat. 80-INSMS-E01, ALPCO). For the insulin ELISA plots, there is a small increase in the amount of insulin released in response to escalation of the glucose dose from 1.67 mM to 16.7 mM. However, in response to the insulin secretagogoues Ex4 and GLP1, and select SAH analogues, there is a substantial increase in GSIS. These data highlight that hydrocarbon stapling, which improves the structural stability, protease resistance, and pharmacologic properties of Ex4 and GLP1, also preserves the key functional GSIS activity of incretins.

ADDITIONAL REFERENCES

Walensky, L. D., Kung, A. L., Escher, I., Malia, T. J., Barbuto, S., et al. (2004) Activation of apoptosis in vivo by a hydrocarbon-stapled BH3 helix. Science, 305(5689), 1466-1470.

Bird, G. H., Bernal, F., Pitter, K., and Walensky, L. D. (2008) Synthesis and biophysical characterization of stabilized alpha-helices of BCL-2 domains. Methods Enzymol, 446, 369-386.

Gavathiotis, E., Suzuki, M., Davis, M. L., Pitter, K., Bird, G. H., et al. (2008) BAX activation is initiated at a novel interaction site. Nature, 455, 1076-1081.

INCORPORATION BY REFERENCE

All patents, patent applications, GenBank/PDB numbers, and published references cited herein are hereby incorporated by reference in their entirety as if they were incorporated individually. While this invention has been particularly shown and described with references to preferred embodiments thereof, it will be understood by those skilled in the art that various changes in form and details may be made therein without departing from the scope of the invention encompassed by the appended claims.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A cross-linked polypeptide comprising an alpha helix and one or more hydrocarbon staples, wherein each hydrocarbon staple stabilizes the alpha helix of the cross-linked polypeptide, and wherein the cross-linked polypeptide comprises a functional exenatide or a functional glucagon-like peptide-1 (GLP-1) polypeptide.

2. The cross-linked polypeptide of claim 1, wherein the polypeptide is exenatide.

3. The cross-linked polypeptide of claim 1, wherein the number of hydrocarbons is between 1 and 10.

4. The cross-linked polypeptide of claim 1, wherein the hydrocarbon staple stabilizes the N-terminal half of the polypeptide.

5. The cross-linked polypeptide of claim 1, wherein the hydrocarbon staple stabilizes the C-terminal half of the polypeptide.

6. The cross-linked polypeptide of claim 1, comprising at least one hydrocarbon staple within the C-terminal half of the polypeptide and at least one hydrocarbon staple within the N-terminal half of the polypeptide.

7. The cross-linked polypeptide of claim 1, wherein the exenatide comprises any one of the amino acid sequences of SEQ ID NOs: 2 or 15-38.

8. The cross-linked polypeptide of claim 1, wherein the GLP-1 polypeptide comprises any one the amino acid sequences SEQ ID NOs: 7-9 or 39-62.

9. The cross-linked polypeptide of claim 1, comprising a first hydrocarbon staple located at position (i, i+3), or (i, i+4) or (i, i+7) relative to the residue positions of the alpha helix of the polypeptide.

10. The cross-linked polypeptide of claim 1, comprising a first hydrocarbon staple located at position (i, i+3), or (i, i+4) or (i, i+7) relative to the residue positions of the alpha helix of the polypeptide, and a second hydrocarbon staple located at position (i, i+3), or (i, i+4) or (i, i+7) relative to the residue positions of the alpha helix of the polypeptide, with the proviso that the first and second hydrocarbon staple are not located at identical positions.

11. The cross-linked polypeptide of claim 1, wherein the cross-linked polypeptide possesses a half-life that is at least 2-fold greater than the half-life of a non-cross-linked counterpart polypeptide.

12. The cross-linked polypeptide of claim 1, comprising at least two hydrocarbon staples which are sequentially arranged and in a stitched configuration whereby the end of the first hydrocarbon staple and the beginning of the second hydrocarbon staple originate at a common residue in the polypeptide.

13. The cross-linked polypeptide of claim 1, wherein the cross-linked polypeptide possesses a resistance to chymotrypsin in vitro that is at least 2-fold greater than the resistance to chymotrypsin in vitro of a non-cross-linked counterpart polypeptide.

14. The cross-linked polypeptide of claim 1, wherein the cross-linked polypeptide possesses a resistance to pepsin in vitro that is at least 6-fold greater than the resistance to pepsin in vitro of a non-cross-linked counterpart polypeptide.

15. The cross-linked polypeptide of claim 1, wherein the cross-linked polypeptide possesses a resistance to a serum protease in vivo that is at least 2-fold greater than the resistance to the serum protease in vivo of non-cross-linked counterpart polypeptide.

16. A pharmaceutical composition comprising a cross-linked polypeptide of claim 1 and one or more pharmaceutically acceptable excipients.

17. The pharmaceutical composition of claim 16, wherein the cross-linked polypeptide is exenatide having the amino acid sequence of SEQ ID NO: 2.

18. A method for treating diabetes comprising administering a therapeutically effective amount of a cross-linked polypeptide of claim 1.

19. The method of claim 18, wherein the cross-linked polypeptide is exenatide.

20. A method for treating diabetes comprising administering a therapeutically effective amount of a pharmaceutical composition of claim 16.

21. The method of claim 20, wherein the cross-linked polypeptide is exenatide.

* * * * *